US007666991B2

(12) United States Patent
Mrsny

(10) Patent No.: US 7,666,991 B2
(45) Date of Patent: Feb. 23, 2010

(54) COMPOSITIONS FOR NEEDLELESS DELIVERY OF ANTIBODIES

(75) Inventor: Randall J. Mrsny, Los Altos, CA (US)

(73) Assignee: Trinity Biosystems, Inc., Menlo Park, CA (US)

( * ) Notice: Subject to any disclaimer, the term of this patent is extended or adjusted under 35 U.S.C. 154(b) by 134 days.

(21) Appl. No.: 11/635,230

(22) Filed: Dec. 5, 2006

(65) Prior Publication Data
US 2007/0141070 A1   Jun. 21, 2007

Related U.S. Application Data

(60) Provisional application No. 60/742,592, filed on Dec. 5, 2005.

(51) Int. Cl.
*C07K 14/00* (2006.01)
*A61K 38/16* (2006.01)

(52) U.S. Cl. .................................... 530/350; 514/12
(58) Field of Classification Search ................ None
See application file for complete search history.

(56) References Cited

U.S. PATENT DOCUMENTS

| | | | |
|---|---|---|---|
| 4,677,070 A * | 6/1987 | Larrick et al. ............... | 435/340 |
| 5,328,984 A | 7/1994 | Pastan et al. | |
| 5,374,620 A | 12/1994 | Clark et al. | |
| 5,458,878 A | 10/1995 | Pastan et al. | |
| 5,512,658 A | 4/1996 | Pastan et al. | |
| 5,541,287 A | 7/1996 | Yau et al. | |
| 5,602,095 A | 2/1997 | Pastan et al. | |
| 5,668,255 A | 9/1997 | Murphy | |
| 5,696,077 A | 12/1997 | Johnson et al. | |
| 5,696,237 A | 12/1997 | FitzGerald et al. | |
| 5,854,044 A | 12/1998 | Pastan et al. | |
| 5,863,745 A | 1/1999 | FitzGerald et al. | |
| 5,965,406 A | 10/1999 | Murphy | |
| 6,022,950 A | 2/2000 | Murphy | |
| 6,022,966 A | 2/2000 | Gustavson et al. | |
| 6,051,405 A | 4/2000 | FitzGerald et al. | |
| 6,072,041 A | 6/2000 | Davis et al. | |
| 6,086,900 A | 7/2000 | Draper | |
| 6,251,392 B1 | 6/2001 | Hein et al. | |
| 6,391,280 B1 | 5/2002 | Hiatt et al. | |
| 6,440,419 B1 | 8/2002 | Hein et al. | |
| 6,485,726 B1 | 11/2002 | Blumberg et al. | |
| 6,488,926 B1 | 12/2002 | Khan et al. | |
| 6,673,574 B2 | 1/2004 | Stern et al. | |
| 2002/0106370 A1 | 8/2002 | Cardy | |
| 2003/0054012 A1 | 3/2003 | Fitzgerald et al. | |
| 2004/0001801 A1 | 1/2004 | Madison et al. | |
| 2004/0071731 A1 | 4/2004 | Fitzgerald | |
| 2004/0209330 A1 | 10/2004 | Xu et al. | |
| 2004/0228831 A1 | 11/2004 | Belinka et al. | |
| 2005/0079171 A1 | 4/2005 | Fitzgerald et al. | |
| 2006/0104993 A1 | 5/2006 | Mrsny | |
| 2006/0110409 A1 | 5/2006 | Shone et al. | |
| 2006/0153798 A1 | 7/2006 | Mrsny | |
| 2007/0003578 A1 | 1/2007 | Fitzgerald | |
| 2007/0141070 A1 | 6/2007 | Mrsny | |
| 2007/0148131 A1 | 6/2007 | Mrsny | |
| 2009/0092660 A1 | 4/2009 | Mrsny | |

FOREIGN PATENT DOCUMENTS

| | | |
|---|---|---|
| WO | WO 86/06635 | 11/1986 |
| WO | WO 95/07297 | 3/1995 |
| WO | WO 98/20135 | 5/1998 |
| WO | WO 98/42876 | 10/1998 |
| WO | WO 00/46246 | 8/2000 |
| WO | WO 01/30392 | 5/2001 |
| WO | WO 01/31020 | 5/2001 |
| WO | WO 03/084470 | 10/2003 |
| WO | WO 2004/043484 | 5/2004 |
| WO | WO 2006/044205 | 4/2006 |

OTHER PUBLICATIONS

ISA/US PCT International Search Report dated Jul. 8, 2008, for International Application No. PCT/US2006/46510, filed Dec. 5, 2006.
U.S. Appl. No. 09/462,682, filed Apr. 28, 2000, Fitzgerald.
U.S. Appl. No. 10/110,880, filed Apr. 16, 2002, Fitzgerald et al.
U.S. Appl. No. 11/664,786, filed Apr. 3, 2007, Mrsny.
U.S. Appl. No. 11/664,787, filed Apr. 3, 2007, Mrsny.
U.S.P.T.O. Non-Final Office Action, dated Sep. 20, 2007, in U.S. Appl. No. 11/244,349, filed Oct. 4, 2005.
U.S.P.T.O. Non-Final Office Action, dated Jul. 22, 2008, in U.S. Appl. No. 11/244,349, filed Oct. 4, 2005.
U.S.P.T.O. Non-Final Office Action, dated Mar. 14, 2006, in U.S. Appl. No. 10/110,880, filed Apr. 16, 2002.
U.S.P.T.O. Non-Final Office Action, dated Feb. 23, 2007, in U.S. Appl. No. 10/110,880, filed Apr. 16, 2002.
PCT International Search Report, dated May 11, 2006, in International Application No. PCT/US2005/35803, filed Oct. 4, 2005.
PCT International Search Report, dated Jan. 10, 2002, in International Application No. PCT/US2000/29080, filed Oct. 18, 2000.
PCT International Search Report, dated Jun. 28, 2007, in International Application No. PCT/US2006/46511, filed Dec. 5, 2006.
PCT International Search Report, dated Aug. 18, 2008, in International Application No. PCT/US2007/17795, filed Aug. 9, 2007.
PCT International Search Report, dated May 21, 2008, in International Application No. PCT/US2007/06590, filed Mar. 15, 2007.
www.cancerweb.ncl.ac.uk/cgi-bin/omd?elastase, Nov. 18, 1997, downloaded Sep. 10, 2007.

(Continued)

*Primary Examiner*—Ilia Ouspenski
(74) *Attorney, Agent, or Firm*—Jones Day

(57) ABSTRACT

The present invention relates, in part, to methods and compositions for needleless delivery of antibodies to a subject. The present invention also relates, in part, to methods for needleless delivery of fusion proteins comprising a bioactive molecule and an antibody fragment to subject. In one aspect, the methods and compositions involve administering to the subject a delivery construct comprising a carrier construct non-covalently bound to the antibody or fusion protein to be delivered, wherein the carrier construct comprises a receptor-binding domain, a transcytosis domain, and an antibody-binding domain to which the antibody or the antibody fragment of the fusion protein non-covalently binds.

22 Claims, 2 Drawing Sheets

Figure 2:
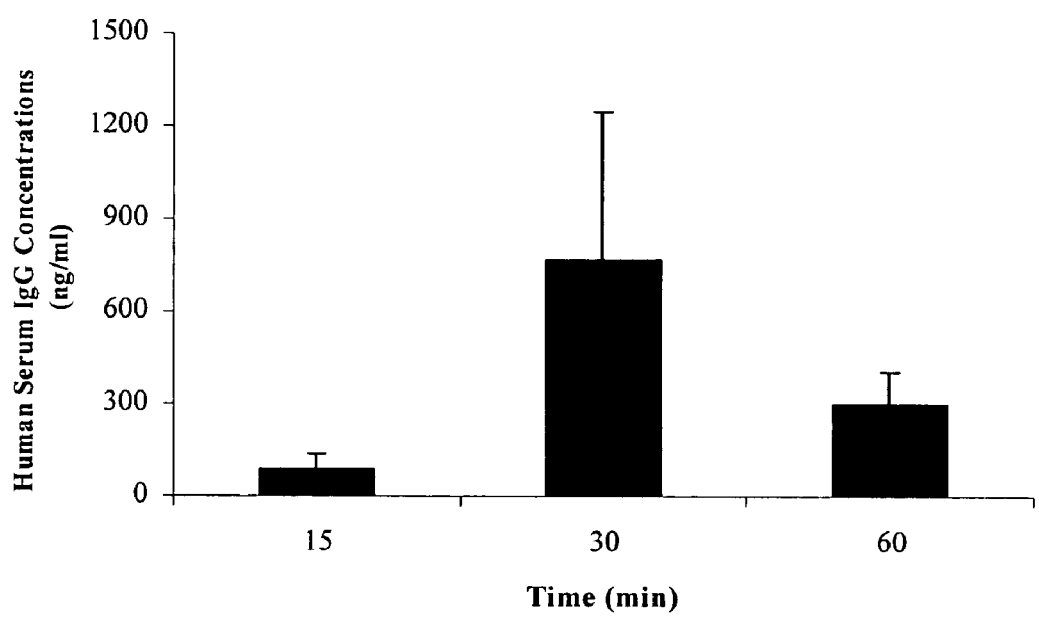

OTHER PUBLICATIONS www.cancerweb.ncl.ac.uk/cgi-bin/omd?leukocyte+elastase, Dec. 12, 1998, downloaded Sep. 10, 2007.

Allured et al., 1986, "Structure of Exotoxin A of Pseudomonas Aeruginosa at Angstrom Resolution," Proc. Natl. Acad. Sci., vol. 83:1320-1324.

Andreasen et al., 1994, "Receptor-Mediated Endocytosis of Plasminogen Activators and Activator/Inhibitor Complexes," FEBS Letters, vol. 338(3):239-245.

Backer et al., 2002, "Molecular Vehicles for Targeted Drug Delivery," Bioconjugate Chem., vol. 13:462-467.

Cavallaro et al., 1995, "Targeting Plant Toxins to the Urokinase and α-2-Macroglobulin Receptors," Semin Cancer Biol., vol. 6(5):269-278.

Cerletti, A. et al., 2000, "Endocytosis and Transcytosis of an Immunoliposome-Based Brain Drug Discovery," J. Drug Targeting, vol. 8(6):435-436.

Daugherty et al., 2000, "Epithelial Application of Pseudomonas Aeruginosa Exotoxin A Results in a Selective Targeting to Cells in the Liver, Spleen and Lymph Node," J. Controlled Release, vol. 65(1-2):297-302.

Fitzgerald et al., 1998, "Characterization of V3 Loop-Pseudonomas Exotoxin Chimeras. Candidate Vaccines for Human Immunodeficiency Virus-1," J. Biol. Chem., vol. 273(16):9951-9958.

Florence, A.T. et al., 2001, "Transcytosis of Nanoparticle and Dendrimer Delivery Systems: Evolving Vistas," Advanced Drug Delivery, vol. 40(Supp. I):569-589.

Foraker, A.B. et al., 2003, "Microfacbricated Porous Silicon Particles Enhance Paracellular Delivery of Insulin Across Intestinal Caco-2 Cell Monolayers," Pharm. Res., vol. 20(1):110-116.

Gray et al., 1984, "Cloning, Nucleotide Sequence, and Expression in Escherichia Coli of the Exotoxin A Structural Gene of Pseudomonas Aeruginosa," PNAS, vol. 81:2645-2649.

Haltner, E. et al., 1997, "Lectins and Bacterial Invasion Factors for Controlling Endo- and Transcytosis of Bioadhesive Drug Carrier Systems," European Journal of Pharmaceutics and Biopharmaceutics, vol. 44(1):3-13.

Kreuter, J. et al., 2002, Apolipoprotein-Mediated Transport of Nanoparticle-Bound Drugs Across the Blood-Brain Barrier, J. Drug. Targeting, vol. 10(4):317-325.

Herz and Strickland, 2001, "LRP: A Multifunctional Scavenger and Signaling Recpetor," J. Clin. Invest., vol. 108(6):779-784.

Kavimandan, N.J. et al., 2006, "Novel Delivery System Based on Complexation Hydrogels as Delivery Vehicles for Insulin-Transferrin Conjugates," Biomaterials, vol. 27(20):3846-3854.

Kounnas et al., 1992, "The Alpha 2-Macroglobulin Receptor/Low Density Lipoprotein Receptor-Related Protein Binds and Internalizes Pseudomonas Exotoxin A." J. Biol. Chem., vol. 267:12420-12423.

Mayer et al., 2003, "Furin Interacts with proMT1-MMP and Integrin αV at Specialized Domains of Renal Cell Plasma Membrane," J. Cell Sci., vol. 116:1763-1773.

Maziere et al., 1992, "Processing and Characterization of the Low Density Lipoprotein Receptor in the Human Colonic Carcinoma Cell Subclone HT29-18: A Potential Pathway for Delivering Therapeutic Drugs and Genes," Biosci. Rep., vol. 12(6):483-494.

Melman et al., 2001, "High Affinity Binding of Receptor-Associated Protein to Heparin and Low Density Lipoprotein Receptor-Related Protein Requires Similar Basic Amino Acid Sequence Motifs," J. Biol. Chem., vol. 276(31):29338-29346.

Mikulska et al., 2000, "Cloning and Analysis of the Gene Encoding the Human Neonatal Fc Receptor," Eur. J. Immunogenet., vol. 27(4):231-240.

Mrsny et al., 1999, "Mucosal Administration of a Chimera Composed of Pseudomonas Exotoxin and the gp 120 V3 Loop Sequence of HIV-1 Induces Both Salivary and Serum Antibody Responses," Vaccine, vol. 17(11-12):1425-1433.

Olivier, J.-C., 2005, "Drug Transport to Brain with Targeted Nanoparticles," J. Am. Soc. Exper. Neuro. Theapeutics, vol. 2:108-119.

Pastan et al., 1992, "Recombinant Toxins as Novel Therapeutic Agents," Annu. Rev. Biochem., vol. 61:331-354.

Radaev et al., 2001, "The Structure of a Human Type III Fcγ Receptor in Complex with Fc," J. Biol. Chem., vol. 276(19):16469.

Siegall et al., 1991, "Analysis of Sequences in Domain II of Pseudomonas Exotoxin A Which Mediate Translocation," Biochemistry, vol. 30:7154-7159.

Vasil et al., 1986, "Molecular Studies of Pseudomonas Exotoxin A Gene," Infect. Immunol., vol. 52:538-548.

Versluis et al., 1999, "Stable Incorporation of a Lipophilic Daunorubicin Prodrug Into Apoliproein E-Exposing Liposomes Induces Uptake of Prodrug Via Low-Density Lipoprotein Receptor In Vivo," J. Pharmacol. Experiment Therap., Vo.. 289(1):1-7.

Voulhoux et al., 2000, "Influence of Deletions Within Domain II of Exotoxin A on its Extracellular Secretion From Pseudomonas Aeruginosa," J. Bacterol., vol. 182:4051-4058.

Wu, G. et al., 2006, "Boron Containing Macromolecules and Nanovehicles as Delivery Agents for Neutron Capture Therapy," Anti-Cancer Agents in Medicinal Chemistry, vol. 6(2):167-184.

Zdanovsky et al., 1995, "Targeting Pseudomonas and Diptheria Toxins to the Alpha-2-Macroglobulin Receptor Via RAP-Toxin and PAI-Toxin Fusions," Prot. Engin,. vol. 8:123.

Office Action for U.S. Appl. No. 11/635,241, mailed Apr. 1, 2009.

U.S.P.T.O. Final Office Action, dated Feb. 4, 2009, in U.S. Appl. No. 11/244,349, filed Oct. 4, 2005.

U.S.P.T.O. Final Office Action, dated Feb. 19. 2009, in U.S. Appl. No. 10/110,880. filed Apr. 16, 2002.

Siccardi et al., "Regulation of intestinal epithelial function: a link between opportunities for macromolecular drug delivery and inflammatory bowel disease," 2004, Advanced Drug Delivery Rev., 57:219-235.

* cited by examiner

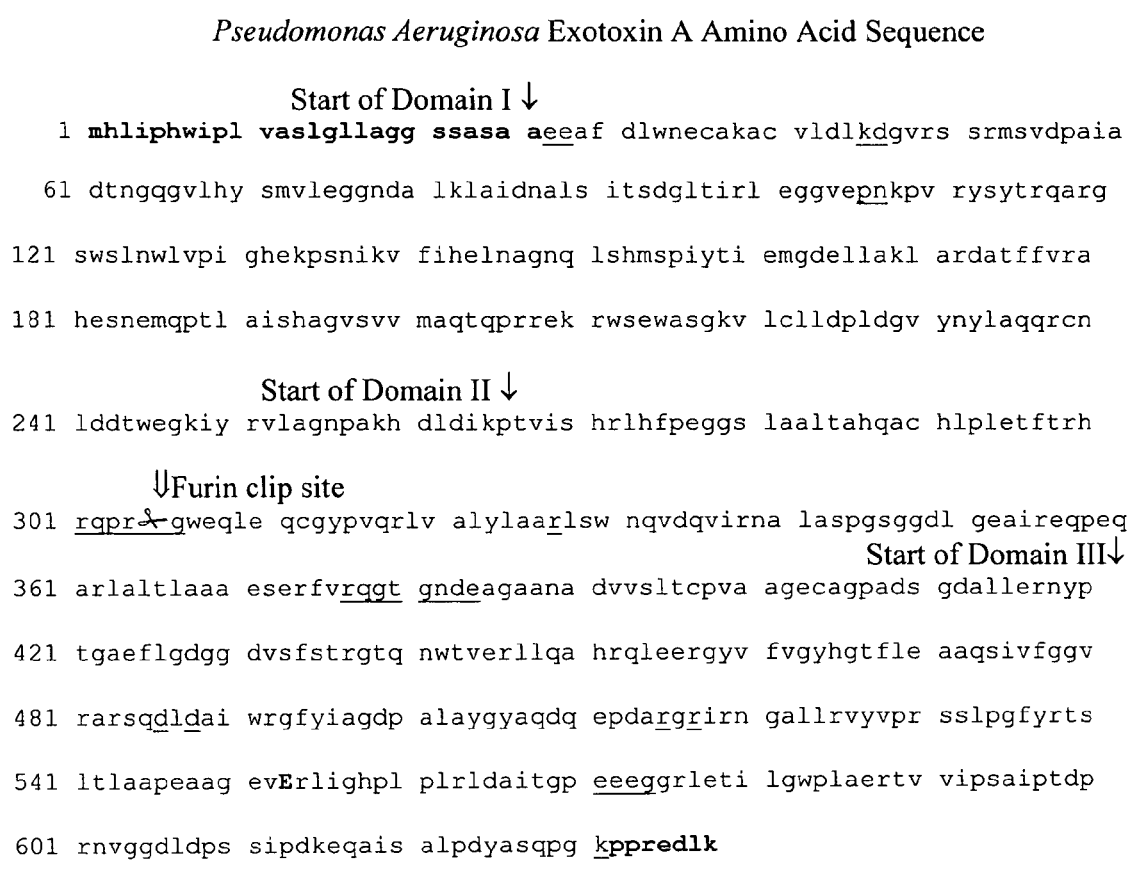

*Pseudomonas Aeruginosa* Exotoxin A Amino Acid Sequence

Start of Domain I ↓
```
  1 mhliphwipl vaslgllagg ssasa aeeaf dlwnecakac vldlkdgvrs srms

US 7,666,991 B2

COMPOSITIONS FOR NEEDLELESS DELIVERY OF ANTIBODIES

This application is entitled to and claims benefit under 35 U.S.C. §119(e) of U.S. Provisional Application No. 60/742,592, filed Dec. 5, 2005, which is hereby incorporated by reference in its entirety.

1. FIELD OF THE INVENTION

The present invention relates, in part, to methods and compositions for needleless delivery of antibodies to a subject. The present invention also relates, in part, to methods for needleless delivery of fusion proteins to subject, the fusion proteins comprising a bioactive molecule and an antibody fragment. In one aspect, the methods and compositions involve administering to the subject a delivery construct comprising a carrier construct non-covalently bound to the antibody or fusion protein to be delivered, wherein the carrier construct comprises a receptor-binding domain, a transcytosis domain, and an antibody-binding domain to which the antibody or the antibody fragment of the fusion protein non-covalently binds.

2. BACKGROUND

Advances in biochemistry and molecular biology have resulted identification and characterization of many therapeutic antibodies. Administration of antibodies can result in drastic improvements in quality of life for subjects afflicted with a wide range of ailments.

However, administration of these therapeutic antibodies remains problematic. Currently, therapeutic antibodies are typically administered by injection. Such injections require penetration of the subject's skin and tissues and are associated with pain. Further, penetration of the skin breaches one effective nonspecific mechanism of protection against infection, and thus can lead to potentially serious infection.

Accordingly, there is an unmet need for new methods and compositions that can be used to administer antibodies to subjects without breaching the skin of the subject. This and other needs are met by the methods and compositions of the present invention.

3. SUMMARY OF THE INVENTION

The present invention provides delivery constructs for the administration of an antibody of interest to a subject. In one aspect of the invention, such delivery constructs comprise a carrier construct non-covalently bound to the antibody. The present invention also provides delivery constructs for the administration of a fusion protein comprising a bioactive molecule and an antibody fragment or antibody. In one aspect of the invention, such delivery constructs comprise a carrier construct non-covalently bound to the antibody fragment or antibody of the fusion protein.

In some embodiments, the carrier constructs of the present invention comprise: (a) a receptor-binding domain, (b) a transcytosis domain, and (c) an antibody-binding domain to which the antibody or the antibody fragment of the fusion protein non-covalently binds. In certain embodiments, the carrier constructs further comprise a cleavable linker, wherein the cleavage at the cleavable linker separates the antibody-binding domain from the remainder of the carrier construct. In one embodiment, the cleavable linker is cleavable by an enzyme that exhibits greater activity at a basal-lateral membrane of a polarized epithelial cell than at an apical membrane of the polarized epithelial cell. In an alternative embodiment, the cleavable linker is cleavable by an enzyme that exhibits greater activity in the plasma of a subject than at an apical membrane of the polarized epithelial cell of the subject.

In some embodiments, the carrier construct comprises an antibody-binding domain consisting of multiple subunits. In certain embodiments, the subunits of the antibody-binding domain are separated by a linker of sufficient length to enable the subunits of the antibody-binding domain to fold so that the antibody-binding domain non-covalently and/or covalently binds to its binding partner. In other embodiments, a subunit of the antibody-binding domain is linked to the remainder of the carrier construct and the construct is incubated with one or more other subunits of the antibody-binding domain under conditions that permit the subunits to associate and form the antibody-binding domain. In these embodiments, the carrier construct that is used in accordance with the invention comprises the both or all of the subunits of the antibody-binding domain. In specific embodiments, the conditions permit the subunits of an antibody-binding domain to associate in the same manner that they do in nature. In accordance with these embodiments, the binding partner is not a subunit of the antibody-binding domain.

In certain embodiments, a carrier construct comprises two antibody-binding domains, wherein the second antibody-binding domain is separated from the remainder of the carrier construct by a cleavable linker and cleavage at the cleavable linker separates the second antibody-binding domain from the remainder of the construct. In some embodiments, a carrier construct comprises two antibody-binding domains and two cleavable linkers, wherein the first cleavable linker separates the first antibody-binding domain from the remainder of the construct and the second cleavable linker separates the second antibody-binding domain from the remainder of the construct. The first and second cleavable linkers are, in some embodiments, the same and in other embodiments, different. In a specific embodiment, the second antibody-binding domain is separated from the first macromolecule by a cleavable linker. In certain embodiments, the first antibody-binding domain is a first polypeptide and said second antibody-binding domain is a second polypeptide. In certain embodiments, the first polypeptide and the second polypeptide associate to form a multimer. In certain embodiments, the multimer is a dimer, tetramer, or octamer.

In accordance with the one aspect of the invention, the antibody-binding domain of a carrier construct non-covalently binds to an antibody or antibody fragment of interest. In some embodiments, the antibody-binding domains of the carrier construct binds to two or more antibodies or antibody fragments of interest. In certain embodiments, the ratio of antibody-binding domain to antibody or antibody fragment is 2:1, 3:1, 4:1, 5:1, or more. In specific embodiments, the antibody-binding domain of the carrier construct specifically binds to the antibody or antibody fragment of interest.

The antibody-binding domain of a carrier construct non-covalently binds to an antibody or an antibody fragment of interest. The antibody-binding domain of a carrier construct may non-covalently bind to a particular type(s), a particular class(es) and/or a particular subclass(es) of an antibody or antibody fragment. Alternatively, the antibody-binding domain of a carrier construct may non-covalently bind to an antibody specific for a particular antigen. In certain embodiments, the antibody-binding domain of a carrier construct non-covalently binds to the Fc region of an antibody or an antibody fragment. In other embodiments, the antibody-binding domain of a carrier construct non-covalently binds to the antigen-binding region of an antibody or an antibody fragment. In yet other embodiments, the antibody-binding domain non-covalently binds to the Fc region and the antigen-binding region of an antibody or an antibody fragment.

In certain embodiments, the antibody-binding domain of a carrier construct comprises Protein A, Protein G, Protein V, Protein L, an Fc receptor (FcR) or an antibody-binding fragment thereof. Non-limiting examples of Fc receptors include FcγRI, FcγRIIA, FcγRIIB, FcγRIIC, FcγRIIIAα, FcγRIIIB, FcεRIα, FcεRIξ and FcγRIIIAξ. In other embodiments, the antibody-binding domain of a carrier construct comprises an antigen to which the antibody or antibody fragment of interest binds.

Any antibody known to one of skill in the art can be non-covalently bound to a carrier construct. Non-limiting examples of antibodies that can be non-covalently bound to a carrier construct include monoclonal antibodies, polyclonal antibodies, multispecific antibodies, human antibodies, humanized antibodies, chimeric antibodies, single domain antibodies, camelised antibodies, single chain Fvs (scFv) single chain antibodies, Fab fragments, F(ab') fragments, disulfide-linked Fvs (sdFv), intrabodies, and anti-idiotypic (anti-Id) antibodies, and epitope-binding fragments of any of the above. In certain embodiments, the antibody specifically binds to an antigen associated with a pathological condition, such as, e.g., an infection, cancer, an autoimmune disorder and an inflammatory disorder. Non-limiting examples of such antigens include EGF, EGF receptor, tumor antigen CA125, tumor antigen MUC1, PEM antigen, CD44, 17-1-A, gp IIIb/IIIa, CD20, gp72, Ep-CAM, HER-2, VEGF, VEGF receptor, CD 18, IgE, nuC242, CEA, CD2, AFP, CTLA-4, $\alpha_v\beta_4$, Ep-CAM, CD52, HLA-DR 10 beta, DNA associated proteins, CD3, CD33, HLA-DR antigen, GD2-ganglioside, SK-1 antigen, IL-2, IL-2 receptor, IL-9, IL-9 receptor, LFA-3, and a viral antigen (e.g., an RSV antigen).

Any fusion protein comprising a bioactive molecule and an antibody or antibody fragment can be non-covalently bound to a carrier construct. In certain embodiments, the fusion comprises an Fc region of an antibody or a fragment thereof. Nonlimiting examples of fusion proteins are provided infra.

The receptor-binding domain of a carrier construct binds (preferably, specifically) to a cell surface receptor that is present on the apical membrane of an epithelial cell. The receptor-binding domain binds to the cell surface with sufficient affinity to allow endocytosis of the delivery construct. In a specific embodiment, the receptor-binding domain of a carrier construct binds to the α2-macroglobulin receptor, epidermal growth factor receptor, transferrin receptor, chemokine receptor, CD25, CD11B, CD11C, CD80, CD86, TNFα receptor, TOLL receptor, M-CSF receptor, GM-CSF receptor, scavenger receptor, or VEGF receptor. In certain embodiments, the receptor-binding domain of a carrier construct comprises a receptor-binding domain from *Pseudomonas* exotoxin A; cholera toxin; botulinum toxin; diptheria toxin; shiga toxin; shiga-like toxin; monoclonal antibodies; polyclonal antibodies; single-chain antibodies; TGF α; EGF; IGF-I; IGF-II; IGF-III; IL-1; IL-2; IL-3; IL-6; MIP-1a; MIP-1b; MCAF; or IL-8. In a specific embodiment, the receptor-binding domain of a carrier construct comprises Domain Ia of *Pseudomonas* exotoxin A.

The transcytosis domain of a carrier construct effects the transcytosis of macromolecules that have bound to a cell surface receptor present on the apical membrane of an epithelial cell. In certain embodiments, the transcytosis domain of a carrier construct comprises a transcytosis domain from *Pseudomonas* exotoxin A, botulinum toxin, diptheria toxin, pertussis toxin, cholera toxin, heat-labile *E. coli* enterotoxin, shiga toxin, or shiga-like toxin. In a specific embodiment, the transcytosis domain of a carrier construct comprises the *Pseudomonas* exotoxin A transcytosis domain.

In certain embodiments, the antibody-binding domain-antibody interaction or the antibody-binding domain-antibody fragment interaction has an on-rate sufficient for association and retention during uptake and transport across epithelial cells and an off-rate sufficient for release of the antibody or the fusion protein once the antibody-binding domain-antibody complex or antibody-binding domain-antibody fragment has reached the basolateral surface. In other embodiments, the antibody-binding domain-antibody interaction or antibody-binding domain-antibody fragment interaction has a similar on-rate and/or off-rate as that found in nature.

The delivery constructs of the invention may be, e.g., produced by incubating a carrier construct and an antibody of interest or a fusion protein comprising a bioactive molecule and an antibody or antibody fragment together under conditions permissible for non-covalent binding of the antibody or antibody fragment to the antibody-binding domain of the carrier construct. Optionally, the delivery constructs formed by such an incubation may be separated from unbound carrier construct and/or unbound antibody or unbound fusion protein using techniques known to one of skill in the art. The delivery constructs of the invention may also be produced by co-expressing a carrier construct and an antibody of interest or a fusion protein comprising a bioactive molecule and an antibody or antibody fragment in cells engineered to comprise a first polynucleotide comprising a first nucleotide sequence encoding the carrier construct and a second polynucleotide comprising a second nucleotide sequence encoding the antibody or the fusion protein. The delivery constructs produced by the cells may be purified. Further, the delivery constructs of the invention may be produced by co-administering to a subject a first composition and a second composition, wherein the first composition comprising a carrier construct and the second composition comprises an antibody or a fusion protein comprising an effector domain and an antibody fragment. In a preferred embodiment, the delivery constructs of the invention are not produced by happenstance in a subject. In a preferred embodiment, the delivery constructs of the invention are purified.

In another aspect, the present invention provides delivery constructs for delivering antibodies, the delivery constructs comprising: (i) a first subunit of an antibody; and (ii) a carrier construct comprising a receptor-binding domain, a transcytosis domain, and a second subunit of the antibody to which the first subunit of the antibody binds. In other words, the first and second subunits of the antibody covalently bind to each other. In accordance with this embodiment, the carrier construct and the first subunit of the antibody are incubated under conditions (e.g., mildly oxidizing conditions) that permit the subunits to associate and form the antibody. In a specific embodiment, the conditions permit the subunits of the antibody to associate in the same manner that they do in nature.

The present invention provides compositions comprising a delivery construct of the invention. In a specific embodiment, the invention provides compositions comprising a delivery construct of the invention and a pharmaceutically acceptable diluent, excipient, vehicle, or carrier. In certain embodiments, the compositions of the invention are pharmaceutical compositions.

The present invention provides methods for delivering an antibody to a subject, the methods comprising contacting an apical surface of a polarized epithelial cell of the subject with a delivery construct of the invention. The present invention also provides methods for delivering an antibody to the bloodstream of a subject, the method comprising contacting a delivery construct of the invention to an apical surface of a polarized epithelial cell of the subject, such that the antibody is delivered to the bloodstream of the subject.

The present invention provides methods for delivering a fusion protein comprising a bioactive molecule and an antibody or antibody fragment to a subject, the methods comprising contacting an apical surface of a polarized epithelial cell of the subject with a delivery construct of the invention. The present invention also provides methods for delivering a fusion protein comprising a bioactive molecule and an antibody or antibody fragment to the bloodstream of a subject, the method comprising contacting a delivery construct of the invention to an apical surface of a polarized epithelial cell of the subject, such that the fusion protein is delivered to the bloodstream of the subject.

Further, the present invention provides methods for preventing, treating, managing and ameliorating a disorder in a subject, the methods comprising administering to the subject a delivery construct of the invention.

4. BRIEF DESCRIPTION OF THE DRAWINGS

FIG. 1 presents the amino acid sequence of an exemplary PE.

FIG. 2 shows, at different time points, the concentration of human IgG present in the serum of mice administered the delivery construct comprising the Fc-binding portion of Protein G and human IgG.

5. DETAILED DESCRIPTION OF THE INVENTION

5.1. Definitions

Unless defined otherwise, all technical and scientific terms used herein have the meaning commonly understood by a person skilled in the art to which this invention belongs. As used herein, the following terms have the meanings ascribed to them unless specified otherwise.

A "ligand" is a compound that specifically binds to a target molecule. Exemplary ligands include, but are not limited to, an antibody, a cytokine, a substrate, a signaling molecule, and the like.

A "receptor" is compound that specifically binds to a ligand.

"Immunoassay" refers to a method of detecting an analyte in a sample involving contacting the sample with an antibody that specifically binds to the analyte and detecting binding between the antibody and the analyte. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. In one example, an antibody that binds a particular antigen with an affinity ($K_m$) of about 10 μM specifically binds the antigen.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc. when there is such a change in environment following transcytosis of the delivery construct across a polarized epithelial membrane.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences, 21st Ed.* 2005, Mack Publishing Co., Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

Preferred pharmaceutical carriers depend upon the intended mode of administration of the active agent. Typical modes of administration include enteral (e.g., oral, intranasal, rectal, or vaginal) or parenteral (e.g., subcutaneous, intramuscular, intravenous or intraperitoneal injection; or topical (e.g., transdermal, or transmucosal administration).

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5000 Da, up to about 2000 Da, or up to about 1000 Da.

The terms "subject" and "patient" are used interchangeably to refer a human or non-human animal, including a mammal or a primate, that is administered a delivery construct.

"*Pseudomonas* exotoxin A" or "PE" is secreted by *Pseudomonas aeruginosa* as a 67 kD protein composed of three prominent globular domains (Ia, II, and III) and one small subdomain (Ib) that connects domains II and III. See A. S. Allured et al., 1986, *Proc. Natl. Acad. Sci.* 83:1320-1324. Without intending to be bound to any particular theory or mechanism of action, domain Ia of PE is believed to mediate cell binding because domain Ia specifically binds to the low density lipoprotein receptor-related protein ("LRP"), also known as the α2-macroglobulin receptor ("α2-MR") and CD-91. See M. Z. Kounnas et al., 1992, *J. Biol. Chem.* 267:12420-23. Domain Ia spans amino acids 1-252. Domain II of PE is believed to mediate transcytosis to the interior of a cell following binding of domain Ia to the α2-MR. Domain II spans amino acids 253-364. Certain portions of this domain may be required for secretion of PE from *Pseudomonas aeruginosa* after its synthesis. See, e.g., Vouloux et al., 2000, *J. Bacterol.* 182:4051-8. Domain Ib has no known function and spans amino acids 365-399. Domain III mediates cytotoxicity of PE and includes an endoplasmic reticulum retention sequence. PE cytotoxicity is believed to result from ADP ribosylation of elongation factor 2, which inactivates protein synthesis. Domain III spans amino acids 400-613 of PE. Deleting amino acid E553 ("ΔE553") from domain III eliminates EF2 ADP ribosylation activity and detoxifies PE. PE having the mutation ΔE553 is referred to herein as "PEΔE553." Genetically modified forms of PE are described in, e.g., U.S. Pat. Nos. 5,602,095; 5,512,658 and 5,458,878 Pseudomonas exotoxin, as used herein, also includes genetically modified, allelic, and chemically inactivated forms of PE within this definition. See, e.g., Vasil et al., 1986, *Infect. Immunol.* 52:538-48. Further, reference to the various domains of PE is made herein to the reference PE sequence presented as FIG. 1. However, one or more domain from modified PE, e.g., genetically or chemically modified PE, or a portion of such domains, can also be used in the chimeric immunogens of the invention so long as the domains retain functional activity. One of skill in the art can readily identify such domains of such modified PE is based on, for example, homology to the PE sequence exemplified in FIG. 1 and test for functional activity using, for example, the assays described below.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. Exemplary levels of sequence identity include, but are not limited to, 60, 70, 80, 85, 90, 95, 98% or more sequence identity to a given sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. Exemplary levels of sequence homology include, but are not limited to, 60, 70, 80, 85, 90, 95, 98% or more sequence homology to a given sequence.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, *J. Mol. Biol.* 215:403-10 (with special reference to the published default setting, i.e., parameters w=4, t=17) and Altschul et al., 1997, *Nucleic Acids Res.*, 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. See id.

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

"Polar Amino Acid" refers to a hydrophilic amino acid having a side chain that is uncharged at physiological pH, but which has at least one bond in which the pair of electrons shared in common by two atoms is held more closely by one of the atoms. Genetically encoded polar amino acids include Asn (N), Gln (Q) Ser (S) and Thr (T).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded nonpolar amino acids include Ala (A), Gly (G), Ile (I), Leu (L), Met (M) and Val (V).

"Hydrophilic Amino Acid" refers to an amino acid exhibiting a hydrophobicity of less than zero according to the normalized consensus hydrophobicity scale of Eisenberg et al., 1984, *J. Mol. Biol.* 179:125-142. Genetically encoded hydrophilic amino acids include Arg (R), Asn (N), Asp (D), Glu (E), Gln (Q), His (H), Lys (K), Ser (S) and Thr (T).

"Hydrophobic Amino Acid" refers to an amino acid exhibiting a hydrophobicity of greater than zero according to the normalized consensus hydrophobicity scale of Eisenberg et al., 1984, *J. Mol. Biol.* 179:125-142. Genetically encoded hydrophobic amino acids include Ala (A), Gly (G), Ile (I), Leu (L), Met (M), Phe (F), Pro (P), Trp (W), Tyr (Y) and Val (V).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Asp (D) and Glu (E).

"Basic Amino Acid" refers to a hydrophilic amino acid having a side chain pK value of greater than 7. Basic amino acids typically have positively charged side chains at physiological pH due to association with a hydrogen ion. Genetically encoded basic amino acids include Arg (R), His (H) and Lys (K).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Amplification" refers to any means by which a polynucleotide sequence is copied and thus expanded into a larger number of polynucleotide molecules, e.g., by reverse transcription, polymerase chain reaction, ligase chain reaction, and the like.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids can be found in Tijssen, 1993, *Laboratory Techniques in Biochemistry and Molecular Biology-Hybridization with Nucleic Acid Probes*, part I, chapter 2, "Overview of principles of hybridization and the strategy of nucleic acid probe assays", Elsevier, NY; Sambrook et al., 2001, *Molecular Cloning: A Laboratory Manual*, Cold Spring Harbor Laboratory, 3rd ed., NY; and Ausubel et al., eds., Current Edition, *Current Protocols in Molecular Biology*, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

One example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2×(or higher) than that observed for an unrelated probe in the particular hybridization assay indicates detection of a specific hybridization.

"Peptide" refers to a compound composed of two or more amino acid residues linked via peptide bonds.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. Conventional notation is used herein to portray polypeptide sequences; the beginning of a polypeptide sequence is the amino-terminus, while the end of a polypeptide sequence is the carboxyl-terminus.

The term "protein" typically refers to large polypeptides, for example, polypeptides comprising more than about 50 amino acids. The term "protein" can also refer to dimers, trimers, and multimers that comprise more than one polypeptide.

"Conservative substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W).

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 48 minutes to 72 minutes.

In the context of the interaction between to macromolecules (e.g., an antibody and an antibody-binding domain of a carrier construct), the term "specifically binds" and analogous terms refer to the binding of a macromolecule to another macromolecule with higher affinity than to any cross-reactive antigen as determined using experimental techniques, such as immunoassays (e.g., radioimmunoassays (RIA) and enzyme-linked immunosorbent assays (ELISAs)) and BIAcore. See, e.g., Paul, ed., 1989, *Fundamental Immunology Second Edition*, Raven Press, New York at pages 332-336 for a discussion regarding antibody specificity. For example, antibody binds specifically to a particular antigen when under designated conditions, the antibody binds preferentially to the particular antigen and does not bind in a significant amount to other antigens present in a sample.

A "disorder" refers to a condition, preferably a pathological condition, in a subject.

A "purified" macromolecule (e.g., a delivery construct or carrier construct) is substantially free of cellular material or other contaminating proteins (e.g., unbound carrier construct and unbound antibody) from the cell or tissue source from which the macromolecule (e.g., a delivery construct or carrier construct) is derived. The language "substantially free of cellular material" includes preparations of a macromolecule (e.g., a delivery construct or carrier construct) in which the macromolecule (e.g., a delivery construct or carrier construct) is separated from cellular components of the cells from which it is recombinantly produced. Thus, a macromolecule (e.g., a delivery construct or carrier construct) that is substantially free of cellular material includes preparations of the macromolecule having less than about 30%, 20%, 10%, or 5% (by dry weight) of heterologous protein (also referred to herein as a "contaminating protein") and/or unbound carrier construct and unbound antibody. When the macromolecule (e.g., a delivery construct or carrier construct) is recombinantly produced, it is also preferably substantially free of culture medium, i.e., culture medium represents less than about 20%, 10%, or 5% of the volume of the macromolecule (e.g., a delivery construct or carrier construct) preparation. In a specific embodiment, a delivery construct of the invention is purified. In another specific embodiment, a carrier construct of the invention is purified. In another specific embodiment, an antibody of the invention is purified.

An "isolated" nucleic acid molecule is one which is separated from other polynucleotides which are present in the natural source of the nucleic acid molecule. Moreover, an "isolated" polynucleotide, such as a cDNA molecule, can be substantially free of other cellular material, or culture medium when produced by recombinant techniques, or substantially free of chemical precursors or other chemicals when chemically synthesized. In certain embodiments, an "isolated" polynucleotide is a nucleic acid molecule that is recombinantly expressed in a heterologous cell.

As used herein, the terms "manage," "managing," and "management" refer to the beneficial effects that a subject derives from a therapy (e.g., a prophylactic or therapeutic agent), which does not result in a cure of the disorder. In certain embodiments, a subject is administered one or more therapies (e.g., prophylactic or therapeutic agents, such as an antibody of the invention) to "manage" a disorder one or more symptoms thereof so as to prevent the progression or worsening of the disorder.

As used herein, the terms "prevent," "preventing," and "prevention" in the context of administering a therapy to a subject refer to the total or partial inhibition of the disorder, or the total or partial inhibition of the development, onset or progression of the disorder and/or a symptom thereof in a subject.

As used herein, the term "therapy" refers to any protocol, method and/or agent that can be used in the prevention, management, treatment and/or amelioration of a disorder or a symptom thereof. In certain embodiments, the terms "therapies" and "therapy" refer to a biological therapy, supportive therapy, and/or other therapies useful in the prevention, management, treatment and/or amelioration of a disorder or a symptom thereof known to one of skill in the art such as medical personnel. In a specific embodiment, a delivery construct is a therapy.

As used herein, the terms "treat," "treatment" and "treating" in the context of administration of a therapy to a subject refer to the reduction or amelioration of the progression, severity, and/or duration of a disorder or a symptom thereof.

As used herein, the term "analog" in the context of a proteinaceous agent (e.g., a peptide, polypeptide, protein or antibody) refers to a proteinaceous agent that possesses a similar or identical function as a second proteinaceous agent but does not necessarily comprise a similar or identical amino acid sequence or structure of the second proteinaceous agent. A proteinaceous agent that has a similar amino acid sequence refers to a proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 20 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure of the second proteinaceous agent. The structure of a proteinaceous agent can be determined by methods known to those skilled in the art, including but not limited to, X-ray crystallography, nuclear magnetic resonance, and crystallographic electron microscopy.

As used herein, the term "derivative" in the context of a proteinaceous agent (e.g., proteins, polypeptides, peptides, and antibodies) refers to a proteinaceous agent that comprises the amino acid sequence which has been altered by the introduction of amino acid residue substitutions, deletions, and/or additions. The term "derivative" as used herein also refers to a proteinaceous agent which has been modified, i.e., by the covalent attachment of a type of molecule to the proteinaceous agent. For example, but not by way of limitation, a derivative of a proteinaceous agent may be produced, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may also be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses an identical function(s) as the proteinaceous agent from which it was derived.

As used herein, the term "fragment" in the context of a proteinaceous agent refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of a second peptide, polypeptide, or protein. In a specific embodiment, a fragment retains one or more functions of the peptide, polypeptide or protein from which it is derived.

The term "transcytosis" and analogous terms refer to the transport of macromolecular cargo from one side of a cell (e.g., the apical side of an epithelial cell) to the other side of the cell (e.g., the basolateral side of an epithelial cell) within a membrane membrane-bounded carrier(s). See, e.g., Tuma et al., 2003, Physiol. Rev. 83: 871-932, which is incorporated herein in its entirety, for a review on transcytosis.

The term "endocytosis" and analogous terms refer to the process by which cells internalize macromolecules and fluid.

5.2. Delivery Constructs

In one embodiment, the delivery constructs of the present invention comprise an antibody non-covalently bound to a carrier construct that comprises a receptor-binding domain, a transcytosis domain and an antibody-binding domain to which the antibody non-covalently binds. In another embodiment, the delivery constructs of the present invention comprise a fusion protein comprising a bioactive molecule and an antibody or antibody fragment non-covalently bound to a carrier construct that generally comprises a receptor-binding domain, a transcytosis domain and an antibody-binding domain to which the antibody or antibody fragment of the fusion protein non-covalently binds. The non-covalent bond between the antibody or the antibody fragment of the fusion protein and antibody-binding domain of the construct may be the result of a single non-covalent bond or, preferably, multiple non-covalent bonds. Non-limiting examples of non-covalent bonds include hydrogen bonds, ionic bonds, van der Waals interactions, and hydrophobic bonds.

The present invention also provides delivery constructs for delivering antibodies, the delivery constructs comprising: (i) a first subunit of an antibody; and (ii) a carrier construct comprising a receptor-binding domain, a transcytosis domain, and a second subunit of the antibody to which the first subunit of the antibody binds. In other words, the first and second subunits of the antibody covalently bind to each other. In accordance with this embodiment, the carrier construct and the first subunit of the antibody are incubated under conditions (e.g., mildly oxidizing conditions) that permit the subunits to associate and form the antibody. In a specific embodiment, the conditions permit the subunits of the antibody to associate in the same manner that they do in nature.

5.3. Carrier Constructs

In one embodiment, the carrier constructs of the invention comprise the following structural elements, each element imparting particular functions to the carrier construct: (i) a "receptor-binding domain" that functions as a ligand for a cell surface receptor and that mediates binding of the construct to a cell, (ii) a transcytosis domain that mediates transcytosis from a lumen bordering the apical surface of a mucous membrane to the basal-lateral side of a mucous membrane, and (iii) a subunit of an antibody to which another subunit of the antibody binds. In certain embodiments, the carrier construct comprises these structural elements in the order listed above from 5' to 3'. Optionally, the carrier construct further comprises a cleavable linker that connects the antibody subunit to the remainder of the carrier construct.

In another embodiment, the carrier constructs of the invention comprise the following structural elements, each element imparting particular functions to the carrier construct: (1) a "receptor-binding domain" that functions as a ligand for a cell surface receptor and that mediates binding of the construct to a cell; (2) a "transcytosis domain" that mediates transcytosis from a lumen bordering the apical surface of a mucous membrane to the basal-lateral side of a mucous membrane; and (3) the "antibody-binding domain" to which an antibody or an antibody fragment non-covalently binds. In certain embodiments, the carrier construct comprises these structural elements in the order listed above from 5' to 3'. Optionally, the carrier construct further comprises a cleavable linker that connects the antibody-binding domain to the remainder of the carrier construct.

Generally, the carrier constructs of the present invention are polypeptides that have structural domains corresponding to domains Ia and II of PE. These structural domains perform certain functions, including, but not limited to, cell recognition and transcytosis, that correspond to the functions of the domains of PE.

In addition to the portions of the molecule that correspond to PE functional domains, the carrier constructs of this invention can further comprise an antibody-binding domain that non-covalently binds to an antibody of interest or a fusion protein comprising a bioactive molecule and an antibody or antibody fragment. The non-covalent bond between the antibody or antibody fragment and antibody-binding domain enables the carrier construct to deliver the antibody or fusion protein to a biological compartment of a subject. The antibody-binding domain can be introduced into any portion of the carrier construct that does not disrupt a cell-binding or transcytosis activity. Optionally, the antibody-binding domain is connected with the remainder of the carrier construct with a cleavable linker.

The carrier constructs of the invention offer several advantages over conventional techniques for local or systemic delivery of antibodies and fusion proteins comprising a bioactive molecule and an antibody or antibody fragment to a subject. Foremost among such advantages is the ability to deliver an antibody or a fusion protein comprising a bioactive molecule and an antibody or antibody fragment without using a needle to puncture the skin of the subject. Many subjects require repeated, regular doses of antibodies. For example, cancer patients must receive multiple injections of antibodies, such as HER-2, to treat or manage their cancer. Such subjects' quality of life would be greatly improved if the delivery of an antibody could be accomplished without injection, by avoiding pain or potential complications associated therewith.

Furthermore, many embodiments of the carrier constructs can be constructed and expressed in recombinant systems. Recombinant technology allows one to make a carrier construct having an insertion site designed for introduction of any suitable antibody-binding domain. Such insertion sites allow the skilled artisan to quickly and easily produce carrier constructs for delivery of new antibodies, should the need to do so arise.

Other advantages of the carrier constructs of the invention will be apparent to those of skill in the art.

In certain embodiments, the invention provides a carrier construct that comprises a receptor-binding domain, a transcytosis domain, an antibody-binding domain, and a cleavable linker. Cleavage at the cleavable linker separates the antibody-binding domain from the remainder of the construct. The cleavable linker is cleavable by an enzyme that is present at a basal-lateral membrane of a polarized epithelial cell of the subject or in the plasma of the subject. In certain embodiments, the enzyme that is at a basal-lateral membrane of a polarized epithelial cell exhibits higher activity on the basal-lateral side of a polarized epithelial cell than it does on the apical side of the polarized epithelial cell. In certain other embodiments, the enzyme that is in the plasma of the subject exhibits higher activity in the plasma than it does on the apical side of a polarized epithelial cell.

In certain embodiments, the carrier construct further comprises a second cleavable linker. In certain embodiments, the first and/or the second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10). In certain embodiments, the first and/or the second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10) and is cleavable by an enzyme that exhibits higher activity on the basal-lateral side of a polarized epithelial cell than it does on the apical side of the polarized epithelial cell. In certain embodiments, the first and/or the second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10) and is cleavable by an enzyme that exhibits higher activity in the plasma than it does on the apical side of a polarized epithelial cell.

In certain embodiments, the enzyme that is present at a basal-lateral membrane of a polarized epithelial cell is selected from the group consisting of Cathepsin GI, Chymotrypsin I, Elastase I, Subtilisin AI, Subtilisin AII, Thrombin I, and Urokinase I.

In certain embodiments, the receptor-binding domain is selected from the group consisting of receptor-binding domains from *Pseudomonas* exotoxin A, cholera toxin, botulinum toxin, diptheria toxin, shiga toxin, or shiga-like toxin; monoclonal antibodies; polyclonal antibodies; single-chain antibodies; TGF α; EGF; IGF-I; IGF-II; IGF-III; IL-1; IL-2; IL-3; IL-6; MIP-1a; MIP-1b; MCAF; and IL-8. In certain embodiments, the receptor-binding domain binds to a cell-surface receptor that is selected from the group consisting of α2-macroglobulin receptor, epidermal growth factor receptor, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor. In further embodiments, the receptor-binding domain of *Pseudomonas* exotoxin A is Domain Ia of *Pseudomonas* exotoxin A. In a specific embodiment, the receptor-binding domain of *Pseudomonas* exotoxin A has an amino acid sequence that is SEQ ID NO.:1.

In certain embodiments, the transcytosis domain is selected from the group consisting of transcytosis domains from *Pseudomonas* exotoxin A, botulinum toxin, diptheria toxin, pertussis toxin, cholera toxin, heat-labile *E. coli* enterotoxin, shiga toxin, and shiga-like toxin. In further embodiments, the transcytosis domain is *Pseudomonas* exotoxin A transcytosis domain. In still further embodiments, the *Pseudomonas* exotoxin A transcytosis domain has an amino acid sequence that is SEQ ID NO.:2.

In certain embodiments, the antibody-binding domain is selected from the group consisting of Protein A, Protein G, Protein V, Protein L, an Fc receptor (FcR) and antibody-binding fragments of any of the foregoing. In other embodiments, the antibody-binding domain is an antigen to which the antibody or antibody fragment of interest binds.

In some embodiments, the carrier construct comprises an antibody-binding domain consisting of multiple subunits. In certain embodiments, the subunits of the antibody-binding domain are separated by a linker of sufficient length to enable the subunits of the antibody-binding domain to fold so that the antibody-binding domain non-covalently and/or covalently binds to its binding partner. In other embodiments, a subunit of the antibody-binding domain is linked to the remainder of the carrier construct and the construct is incubated with one or more other subunits of the antibody-binding domain under conditions that permit the subunits to associate and form the antibody-binding domain. In these embodiments, the carrier construct that is used in accordance with the invention comprises the both or all of the subunits of the antibody-binding domain. In specific embodiments, the conditions permit the subunits of an antibody-binding domain to associate in the same manner that they do in nature. In accordance with these embodiments, the binding partner is not a subunit of the antibody-binding domain.

In certain embodiments, a carrier construct comprises two antibody-binding domains, wherein the second antibody-binding domain is separated from the remainder of the carrier construct by a cleavable linker and cleavage at the cleavable linker separates the second antibody-binding domain from the remainder of the construct. In some embodiments, a carrier construct comprises two antibody-binding domains and two cleavable linkers, wherein the first cleavable linker separates the first antibody-binding domain from the remainder of the construct and the second cleavable linker separates the second antibody-binding domain from the remainder of the construct. The first and second cleavable linkers are, in some embodiments, the same and in other embodiments, different. In a specific embodiment, the second antibody-binding domain is separated from the first antibody-binding domain by a cleavable linker. In certain embodiments, the first antibody-binding domain is a first polypeptide and said second antibody-binding domain is a second polypeptide. In certain embodiments, the first polypeptide and the second polypeptide associate to form a multimer. In certain embodiments, the multimer is a dimer, tetramer, or octamer. In vitro studies with polarized epithelial systems representing the gastrointestinal or pulmonary, or other human tissues comprising epithelial cells can be used to assess the capacity (including the efficiency) of linker separation. In specific embodiments, these linkers are 4-8, 4-12, 4-16, 4-20, 8-12, 8-16 or 8-20 amino acids in length for sufficient specificity of an enzyme.

5.3.1. Receptor-binding Domain

The carrier constructs of the invention generally comprise a receptor-binding domain. The receptor-binding domain can be any receptor-binding domain known to one of skill in the art without limitation to bind to a cell surface receptor that is present on the apical membrane of an epithelial cell. Preferably, the receptor-binding domain binds specifically to the cell surface receptor. The receptor-binding domain should bind to the cell surface receptor with sufficient affinity to allow endocytosis of the delivery construct.

In certain embodiments, the receptor-binding domain comprises a peptide, a polypeptide, a protein, a lipid, a carbohydrate, or a small organic molecule, or a combination thereof. Examples of each of these molecules that bind to cell surface receptors present on the apical membrane of epithelial cells are well known to those of skill in the art. Suitable peptides or polypeptides include, but are not limited to, bacterial toxin receptor-binding domains, such as the receptor-binding domains from PE, cholera toxin, botulinum toxin, diptheria toxin, shiga toxin, shiga-like toxin, etc.; antibodies, including monoclonal, polyclonal, and single-chain antibodies, or derivatives thereof, growth factors, such as EGF, IGF-I, IGF-II, IGF-III etc.; cytokines, such as IL-1, IL-2, IL-3, IL-6, etc; chemokines, such as MIP-1a, MIP-1b, MCAF, IL-8, etc.; and other ligands, such as CD4, cell adhesion molecules from the immunoglobulin superfamily, integrins, ligands specific for the IgA receptor, etc. See, e.g., Pastan et al., 1992, *Annu. Rev. Biochem.* 61:331-54; and U.S. Pat. Nos. 5,668,255, 5,696,237, 5,863,745, 5,965,406, 6,022,950, 6,051,405, 6,251,392, 6,440,419, and 6,488,926. The skilled artisan can select the appropriate receptor-binding domain based upon the expression pattern of the receptor to which the receptor-binding domain binds.

Lipids suitable for receptor-binding domains include, but are not limited to, lipids that themselves bind cell surface receptors, such as sphingosine-1-phosphate, lysophosphatidic acid, sphingosylphosphorylcholine, retinoic acid, etc.; lipoproteins such as apolipoprotein E, apolipoprotein A, etc., and glycolipids such as lipopolysaccharide, etc.; glycosphingolipids such as globotriaosylceramide and galabiosylceramide; and the like. Carbohydrates suitable for receptor-binding domains include, but are not limited to, monosaccharides, disaccharides, and polysaccharides that comprise simple sugars such as glucose, fructose, galactose, etc.; and glycoproteins such as mucins, selectins, and the like. Suitable small organic molecules for receptor-binding domains include, but are not limited to, vitamins, such as vitamin A, $B_1$, $B_2$, $B_3$, $B_6$, $B_9$, $B_{12}$, C, D, E, and K, amino acids, and other small molecules that are recognized and/or taken up by receptors present on the apical surface of epithelial cells. U.S. Pat. No. 5,807,832 provides an example of such small organic molecule receptor-binding domains, vitamin $B_{12}$.

In certain embodiments, the receptor-binding domain binds to a receptor found on an epithelial cell. In further embodiments, the receptor-binding domain can bind to a receptor found on the apical membrane of an epithelial cell. The receptor-binding domain can bind to any receptor known to be present on the apical membrane of an epithelial cell by one of skill in the art without limitation. For example, the receptor-binding domain can bind to α2-MR, EGFR, or IGFR. An example of a receptor-binding domain that can bind to α2-MR is domain Ia of PE. Accordingly, in certain embodiments, the receptor-binding domain is domain Ia of PE. In other embodiments, the receptor-binding domain is a portion of domain Ia of PE that can bind to α2-MR. Exemplary receptor-binding domains that can bind to EGFR include, but are not limited to, EGF and TGFα. Examples of receptor-binding domains that can bind to IGFR include, but are not limited to, IGF-I, IGF-II, or IGF-III. Thus, in certain embodiments, the receptor-binding domain is EGF, IGF-I, IGF-II, or IGF-III. In other embodiments, the receptor-binding domain is a portion of EGF, IGF-I, IGF-II, or IGF-III that can bind to the EGF or IGF receptor.

In certain embodiments, the receptor-binding domain binds to a receptor that is highly expressed on the apical membrane of a polarized epithelial cell but is not expressed or expressed at low levels on antigen presenting cells, such as, for example, dendritic cells. Exemplary receptor-binding domains that have this kind of expression pattern include, but are not limited to, TGFα, EGF, IGF-I, IGF-II, and IGF-III.

In certain embodiments, the delivery constructs of the invention comprise more than one domain that can function as a receptor-binding domain. For example, the delivery construct can comprise PE domain Ia in addition to another receptor-binding domain.

The receptor-binding domain can be attached to the remainder of the carrier construct by any method or means known by one of skill in the art to be useful for attaching such molecules, without limitation. In certain embodiments, the receptor-binding domain is expressed together with the remainder of the carrier construct as a fusion protein. Such embodiments are particularly useful when the receptor-binding domain and the remainder of the construct are formed from peptides or polypeptides.

In other embodiments, the receptor-binding domain is connected with the remainder of the carrier construct with a linker. In yet other embodiments, the receptor-binding domain is connected with the remainder of the carrier construct without a linker. Either of these embodiments is useful when the receptor-binding domain comprises a peptide, polypeptide, protein, lipid, carbohydrate, nucleic acid, or small organic molecule.

In certain embodiments, the linker can form a covalent bond between the receptor-binding domain and the remainder of the carrier construct. In certain embodiments, the covalent bond can be a peptide bond. In other embodiments, the linker can link the receptor-binding domain to the remainder of the construct with one or more non-covalent interactions of sufficient affinity. One of skill in the art can readily recognize linkers that interact with each other with sufficient affinity to be useful in the carrier constructs of the invention. For example, biotin can be attached to the receptor-binding domain, and streptavidin can be attached to the remainder of the carrier construct. In certain embodiments, the linker can directly link the receptor-binding domain to the remainder of the carrier construct. In other embodiments, the linker itself comprises two or more molecules that associate in order to link the receptor-binding domain to the remainder of the carrier construct. Exemplary linkers include, but are not limited to, straight or branched-chain carbon linkers, heterocyclic carbon linkers, substituted carbon linkers, unsaturated carbon linkers, aromatic carbon linkers, peptide linkers, etc.

In embodiments where a linker is used to connect the receptor-binding domain to the remainder of the carrier construct, the linkers can be attached to the receptor-binding domain and/or the remainder of the carrier construct by any means or method known by one of skill in the art without limitation. For example, the linker can be attached to the receptor-binding domain and/or the remainder of the carrier construct with an ether, ester, thioether, thioester, amide, imide, disulfide, peptide, or other suitable moiety. The skilled artisan can select the appropriate linker and method for attaching the linker based on the physical and chemical properties of the chosen receptor-binding domain and the linker. The linker can be attached to any suitable functional group on the receptor-binding domain or the remainder of the carrier construct. For example, the linker can be attached to sulfhydryl (—S), carboxylic acid (—COOH) or free amine (—NH2) groups, which are available for reaction with a suitable functional group on a linker. These groups can also be used to connect the receptor-binding domain directly connected with the remainder of the carrier construct in the absence of a linker.

Further, the receptor-binding domain and/or the remainder of the carrier construct can be derivatized in order to facilitate attachment of a linker to these moieties. For example, such derivatization can be accomplished by attaching suitable derivative such as those available from Pierce Chemical Company, Rockford, Ill. Alternatively, derivatization may involve chemical treatment of the receptor-binding domain and/or the remainder of the carrier construct. For example, glycol cleavage of the sugar moiety of a carbohydrate or glycoprotein receptor-binding domain with periodate generates free aldehyde groups. These free aldehyde groups may be reacted with free amine or hydrazine groups on the remainder of the molecule in order to connect these portions of the molecule. See, e.g., U.S. Pat. No. 4,671,958. Further, the skilled artisan can generate free sulfhydryl groups on proteins to provide a reactive moiety for making a disulfide, thioether, thioester, etc. linkage. See, e.g., U.S. Pat. No. 4,659,839.

Any of these methods for attaching a linker to a receptor-binding domain and/or the remainder of a carrier construct can also be used to connect a receptor-binding domain with the remainder of the carrier construct in the absence of a linker. In such embodiments, the receptor-binding domain is coupled with the remainder of the construct using a method suitable for the particular receptor-binding domain. Thus, any method suitable for connecting a protein, peptide, polypeptide, nucleic acid, carbohydrate, lipid, or small organic molecule to the remainder of the carrier construct known to one of skill in the art, without limitation, can be used to connect the receptor-binding domain to the remainder of the construct. In addition to the methods for attaching a linker to a receptor-binding domain or the remainder of a carrier construct, as described above, the receptor-binding domain can be connected with the remainder of the construct as described, for example, in U.S. Pat. Nos. 6,673,905; 6,585,973; 6,596,475; 5,856,090; 5,663,312; 5,391,723; 6,171,614; 5,366,958; and 5,614,503.

In certain embodiments, the receptor-binding domain is a monoclonal antibody. In some of these embodiments, the receptor-binding domain is expressed as a fusion protein that comprises an immunoglobulin heavy chain from an immunoglobulin specific for a receptor on a cell to which the chimeric immunogen is intended to bind. The light chain of the immunoglobulin then can be co-expressed with the chimeric immunogen, thereby forming a light chain-heavy chain dimer. In other embodiments, the antibody can be expressed and assembled separately from the remainder of the chimeric immunogen and chemically linked thereto.

5.3.2. Transcytosis Domain

The carrier constructs of the invention also comprise a transcytosis domain. The transcytosis domain can be any transcytosis domain known by one of skill in the art to effect transcytosis of macromolecules that have bound to a cell surface receptor present on the apical membrane of an epithelial cell. In certain embodiments, the transcytosis domain is a transcytosis domain from PE, diptheria toxin, pertussis toxin, cholera toxin, heat-labile *E. coli* enterotoxin, shiga toxin, or shiga-like toxin. See, for example, U.S. Pat. Nos. 5,965,406, and 6,022,950. In preferred embodiments, the transcytosis domain is domain II of PE.

The transcytosis domain need not, though it may, comprise the entire amino acid sequence of domain II of native PE, which spans residues 253-364 of PE. For example, the transcytosis domain can comprise a portion of PE that spans residues 280-344 of domain II of PE. The amino acids at positions 339 and 343 appear to be necessary for transcytosis. See Siegall et al., 1991, *Biochemistry* 30:7154-59. Further, conservative or nonconservative substitutions can be made to the amino acid sequence of the transcytosis domain, as long as transcytosis activity is not substantially eliminated. A representative assay that can routinely be used by one of skill in the art to determine whether a transcytosis domain has transcytosis activity is described below.

Without intending to be limited to any particular theory or mechanism of action, the transcytosis domain is believed to permit the trafficking of the delivery construct through a polarized epithelial cell after the construct binds to a receptor present on the apical surface of the polarized epithelial cell. Such trafficking through a polarized epithelial cell is referred to herein as "transcytosis." This trafficking permits the release of the delivery construct from the basal-lateral membrane of the polarized epithelial cell.

5.3.3. Antibody-Binding Domain

The carrier constructs of the invention can also comprise an antibody-binding domain. The antibody-binding domain can be any molecule known by one of skill in the art to which an antibody or antibody fragment (e.g., the Fc region of an antibody or a fragment thereof) non-covalently binds. For example, the molecule may be a peptide, a polypeptide, a protein, a nucleic acid, a carbohydrate, a lipid, a glycoprotein, synthetic organic and inorganic compounds, or any combination thereof which binds to an antibody or an antibody fragment. The antibody-binding domain may bind to an antibody of interest via a single non-covalent bond or, preferably, multiple non-covalent bonds. Non-limiting examples of non-covalent bonds include hydrogen bonds, ionic bonds, van der Waals interactions, and hydrophobic bonds.

The antibody-binding domain of a carrier construct may non-covalently bind to a particular type(s), a particular class(es) and/or a particular subclass(es) of an antibody or antibody fragment. Alternatively, the antibody-binding domain of a carrier construct may non-covalently bind to an antibody or antibody fragment specific for a particular antigen. In a specific embodiment, the antibody-binding domain specifically binds to an antibody or an antibody fragment of interest.

In certain embodiments, the antibody-binding domain is any macromolecule that non-covalently to an antibody(ies) or antibody fragment(s) of interest. In specific embodiments, the antibody-binding domain of the carrier construct specifically binds to the antibody(ies) or antibody fragment(s) of interest. In a specific embodiment, the antibody-binding domain is one that non-covalently binds to one or more of the antibodies or antibody fragments recited herein. For example, in certain embodiments, the ratio of antibody-binding domain to antibody or antibody fragment is 2:1, 3:1, 4:1 or 5:1.

In certain embodiments, the antibody-binding domain-antibody interaction or the antibody-binding domain-antibody fragment interaction has an on-rate sufficient for association and retention during uptake and transport across epithelial cells and an off-rate sufficient for release of the antibody or fusion protein once the antibody-binding domain-antibody or antibody-binding domain-antibody fragment complex has reached the basolateral surface. In other embodiments, the antibody-binding domain-antibody interaction or the antibody-binding domain-antibody fragment interaction has a similar on-rate and/or off-rate as that found in nature.

In certain embodiments, the antibody-binding domain of a carrier construct of the invention has a high association rate constant for the antibody or antibody fragment. In specific embodiments, the antibody-binding domain of a carrier construct of the invention and the antibody or antibody fragment have an association rate constant or $k_{on}$ rate of about $10^5$ $M^{-1}s^{-1}$ or more, about $5\times10^5$ $M^{-1}s^{-1}$ or more, about $10^6$ $M^{-1}s^{-1}$ or more, about $5\times10^6$ $M^{-1}S^{-1}$ or more, about $10^7$ $M^{-1}s^{-1}$ or more, about $5\times10^7 M^{-1}s^{-1}$ or more, about $10^8$ $M^{-1}s^{-1}$ or more, about $5\times10^8$ $M^{-1}s^{-1}$ or more, or about $1\times10^9$ $M^{-1}s^{-1}$ or more.

In other embodiments, the antibody-binding domain of a carrier construct of the invention and the antibody or antibody fragment have a $k_{off}$ rate of about $5\times10^{-1}$ $s^{-1}$ or less, about $10^{-1}$ $s^{-1}$ or less, about $5\times10^{-2}$ $s^{-1}$ or less, about $10^{-2}$ $s^{-1}$ or less, about $5\times10^{-3}$ $s^{-1}$ or less, about $10^{-3}$ $s^{-1}$ or less, about $5\times10^{-4}$ $s^{-1}$ or less, about $10^{-4}$ $s^{-1}$ or less, about $5\times10^{-5}$ $s^{-1}$ or less, about $10^{-5}$ $s^{-1}$ or less, about $5\times10^{-6}$ $s^{-1}$ or less, about $10^{-6}$ $s^{-1}$ or less, about $5\times10^{-7}$ $s^{-1}$ or less, about $10^{-7}s^{-1}$ or less, about $5\times10^{-8}s^{-1}$ or less, about $10^{-8}$ $s^{-1}$ or less, about $5\times10^{-9}$ $s^{-1}$ or less, about $10^{-9}$ $s^{-1}$ or less, about $5\times10^{-10}$ $s^{-1}$ or less, or about $10^{-10}$ $s^{-1}$ or less.

In certain embodiments, the antibody-binding domain of a carrier construct of the invention and the antibody or antibody fragment have an affinity constant or $K_a$ ($k_{on}/k_{off}$) of about $10^2$ $M^{-1}$ or more, about $5\times10^2$ $M^{-1}$ or more, about $10^3$ $M^{-1}$ or more, about $5\times10^3$ $M^{-1}$ or more, about $10^4 M^{-1}$ or more, about $5\times10^4$ $M^{-1}$ or more, about $10^5$ $M^{-1}$ or more, about $5\times10^5$ $M^{-1}$ or more, about $10^6$ $M^{-1}$ or more, about $5\times10^6$ $M^{-1}$ or more, about $10^7$ $M^{-1}$ or more, about $5\times10^7$ $M^{-1}$ or more, about $10^8$ $M^{-1}$ or more, about $5\times10^8$ $M^{-1}$ or more, about $10^9$ $M^{-1}$ or more, about $5\times10^9$ $M^{-1}$ or more, about $10^{10}$ $M^{-1}$ or more, about $5\times10^{10}$ $M^{-1}$ or more, about $10^{11}$ $M^{-1}$ or more, about $5\times10^{11}$ $M^{-1}$ or more, about $10^{12}$ $M^{-1}$ or more, about $5\times10^{12}$ $M^{-1}$ or more, about $10^{13}$ $M^{-1}$ or more, about $5\times10^{13}$ $M^{-1}$ or more, about $10^{14}$ $M^{-1}$ or more, about $5\times10^{14}$ $M^{-1}$ or more, about $10^{15}$ $M^{-1}$ or more, or about $5\times10^{15}$ $M^{-1}$ or more.

In certain embodiments, the antibody-binding domain of a carrier construct of the invention has a low dissociation constant for the antibody or antibody fragment. In certain embodiments, the macromolecule of a carrier construct of the invention has a high association constant. In certain embodiments, the macromolecule of a carrier construct of the invention has a dissociation constant or $K_d$ ($k_{off}/k_{on}$) for antibody about $5\times10^{-1}$ M or less, about $10^{-1}$ M or less, about $5\times10^{-2}$ M or less, about $10^{-2}$ M or less, about $5\times10^{-3}$ M or less, about $10^{-3}$ M or less, about $5\times10^{-4}$ M or less, about $10^{-4}$ M or less, about $5\times10^{-5}$ M or less, about $10^{-5}$ M or less, about $5\times10^{-6}$ M or less, about $10^{-6}$ M or less, about $5\times10^{-7}$ M or less, about $10^{-7}$ M or less, about $5\times10^{-8}$ M or less, about $10^{-8}$ M or less, about $5\times10^{-9}$ M or less, about $10^{-9}$ M or less, about $5\times10^{-10}$ M or less, or about $10^{-10}$ M or less.

In certain embodiments, the antibody-binding domain of a carrier construct non-covalently binds to the Fc region of an antibody. In specific embodiments, the antibody-binding domain of a carrier construct non-covalently binds to the CH2, and/or CH3 region(s) of an antibody. In other embodiments, the antibody-binding domain of a carrier construct non-covalently binds to the CH2, CH3 and hinge regions of an antibody. In yet other embodiments, the antibody-binding domain of a carrier construct non-covalently binds to the CH1 region of an antibody.

In certain embodiments, the antibody-binding domain of a carrier construct non-covalently binds to the antigen-binding region of an antibody. In specific embodiments, the anitbody-binding domain of a carrier construct binds to the variable heavy (VH) domain and/or variable light (VL) domain of an antibody. In other embodiments, the antibody-binding domain of a carrier construct binds to the VH chain and/or VL chain. In certain other embodiments, the antibody-binding domain of a carrier construct binds to the CH1 and CH2 and/or CH3 region(s) of an antibody. In yet other embodiments, the antibody-binding domain non-covalently binds to the Fc region and the antigen-binding region of an antibody.

In certain embodiments, the antibody-binding domain of a carrier construct comprises a bacterial or bacterial-derived antibody-binding protein, polypeptide or peptide. Non-limiting examples of such antibody-binding domains include Protein A, Protein G, Protein V, Protein L, LAG, Protein LG, Protein AG and antibody-binding fragments thereof. Protein A is produced by *Staphylococcus aureus*, Protein G is produced by *Streptococcus pyogenes*, Protein V is produced by *Gardnerall vaginalis* (see, e.g., U.S. Pat. No. 5,128,451 (which is hereby incorporated by reference) for a description of Protein V), Protein L is produced by *Peptostreptococcus magnus*, and ZAG is produced by *Streptococcus zooepidermicus*. Protein LG is a hybrid of Protein L and Protein G (see, e.g., Kihlberg et al., 1992, *J. Biol. Chem.* 267: 25583-25588 (which is hereby incorporated by reference) for a description of the hybrid protein). Protein AG is a hybrid of Protein A and Protein G (see, e.g., Sun et al., 1992, *J. Immunol. Methods* 152: 43-48 (which is hereby incorporated by reference) for a description of the hybrid protein). See, e.g., Goward et al., 1993, TIBS 18: 136-140, which is incorporated herein in its entirety, for a discussion about bacterial proteins that bind to cellular receptors, antibodies or antibody fragments.

In certain embodiments, an antibody-binding fragment of a bacterial protein or polypeptide is used as the antibody-binding domain of a carrier construct. For example, in some embodiments, the antibody-binding domain is the Z domain of Protein A. See, e.g., U.S. Pat. No. 6,197,927 and Braisted et al, 1996, PNAS USA 93: 5688-5692 (which are hereby incorporated by reference) for a description of such antibody-binding domains. In other embodiments, the antibody-binding domain is an analog or derivative of a bacterial antibody-binding domain.

The bacterial antibody-binding domains have different binding affinities for antibodies from different species. For example, Protein L binds to human immunoglobulin (Ig), pig Ig, chicken Ig, hamster Ig and guinea pig Ig but does not bind to bovine Ig, sheep Ig and goat Ig. Protein A binds to human Ig, rabbit Ig, hamster Ig, and bovine Ig but does not bind to chicken Ig.

Further, the bacterial antibody-binding domains have different binding affinities for different types, classes and subclasses of antibodies of a given species. For example, Protein L binds to human subclasses of IgG1, IgG2, IgG3 and IgG4 containing kappa domain. Protein L also binds to Fab, F(ab')s, scFv, and kappa fragments of human immunoglobulins. However, Protein L does not bind to Fc and lambda fragments of human immunoglobulins. Protein A binds to human IgG1, human IgG2, human IgG4, human IgM, human IgA and human IgE. However, Protein A does not bind to human IgG3, Fc fragments and kappa fragments. Protein G binds to human IgG1, human IgG2, human IgG3 and human IgG4 but does not bind to human IgM, human IgA, human IgE, human scFv, human kappa fragments and human lambda fragments.

In certain embodiments, the antibody-binding domain is a plant macromolecule that non-covalently binds to an antibody or antibody fragment, such as a plant lectin, or an antibody-binding analog, derivative or fragment thereof. In a specific embodiment, the plant antibody-binding domain is jacalin. Jaculin binds to human IgA1, human IgA2 and human IgD. See, e.g., Aucouturier et al., 1988, J. Immunol. Methods 113(2): 185-91 (which is hereby incorporated by reference) for a description of the antibody binding activity of jaculin.

In certain embodiments, the antibody-binding domain is a receptor or an analog, derivative or a fragment thereof that binds to the Fc region of an antibody. Preferably, the receptor is from or derived from the same species that is to receive the delivery construct. In a specific embodiment, the antibody-binding domain is an Fc receptor (FcR) or an analog, derivative or antibody-binding fragment thereof. Non-limiting examples of Fc receptors include FcγRI, FcγRIIA, FcγRIIB, FcγRIIC, FcγRIIIAα, FcγRIIIB, FcεRIα, FcεRIξ, FcγRII-IAξ, and FcRn. See, e.g., Ravetch et al., 1991, Annu. Rev. Immunol. 9: 457-492; Ravetech, 1994, Cell 78: 573-560; Ravetech et al., 2000, Science 290: 84-89; Gerber et al., 2001, Microbes and Infection 131-139; Ravetech, 2001, Annu. Rev. Immunol. 19: 275-290; Ghetie and Ward, 2000, Annu. Rev. Immunol. 18:739-766; U.S. Publication No. 2004/0265321; U.S. Publication No. 2005/0215767; U.S. Publication No. 2004/0185045 (which are hereby incorporated by reference) for descriptions of Fc receptors and fragments thereof.

In certain embodiments, the antibody-binding domain of a carrier construct comprises an antigen to which the antibody of interest binds. Preferably, the antigen is from or derived from the same species that is to receive the delivery construct. In some embodiments, the antigen is similar or identical to the antigen that the antibody binds to or is expected to bind to in a subject. In other embodiments, the antigen is distinct from the antigen that the antibody binds to or is expected to bind to in a subject. In specific embodiments, the antigen that the antibody binds to or is expected to bind to in a subject has a higher affinity for the antibody than the antigen that is part of the carrier construct.

One of skill in the art will appreciate that depending upon the type, class, and subclass of the antibody or antibody fragment to be non-covalently bound to an antibody-binding domain certain antibody-binding domains will be more suitable than others and the skilled artisan will select an appropriate antibody-binding domain accordingly. One of skill in the art will also appreciate that the species of the subject being administered a delivery construct of the invention will affect the antibody-binding domain chosen and thus, will select an appropriate antibody-binding domain taking into consideration the species receiving the delivery construct. To minimize an immune response to the antibody-binding domain of the carrier construct, it is preferable to choose an antibody-binding domain that is from or derived from the species receiving the delivery construct. Further, one of skill in the art will appreciate that the affinity of the antibody-binding domain for the antibody or antibody fragment will affect the amount of antibody or fusion protein comprising a bioactive molecule and an antibody fragment delivered to the subject and the skilled artisan will select an antibody-binding domain with suitable affinity for the antibody or antibody fragment to deliver an sufficient amount of the antibody or the fusion protein to the subject to have a prophylactic and/or therapeutic effect.

The antibody-binding domain can be attached to the remainder of the carrier construct by any method known by one of skill in the art, without limitation. In certain embodiments, the antibody-binding domain is expressed together with the remainder of the carrier construct as a fusion protein. In such embodiments, the antibody-binding domain may be inserted into or attached to any portion of the carrier construct, so long as the receptor-binding domain, the transcytosis domain, and antibody-binding domain retain their activities. Optionally, the antibody-binding domain is connected with the remainder of the construct with a cleavable linker, or a combination of cleavable linkers, as described below.

In native PE, the Ib loop (domain Ib) spans amino acids 365 to 399, and is structurally characterized by a disulfide bond between two cysteines at positions 372 and 379. This portion of PE is not essential for any known activity of PE, including cell binding, transcytosis, ER retention or ADP ribosylation activity. Accordingly, domain Ib can be deleted entirely, or modified to contain an antibody-binding domain.

Thus, in certain embodiments, an antibody-binding domain can be inserted into domain Ib. If desirable, the antibody-binding domain can be inserted into domain Ib wherein the cysteines at positions 372 and 379 are not cross-linked. This can be accomplished by reducing the disulfide linkage between the cysteines, by deleting the cysteines entirely from the Ib domain, by mutating the cysteines to other residues, such as, for example, serine, or by other similar techniques. Alternatively, the antibody-binding domain can be inserted into the Ib loop between the cysteines at positions 372 and 379. In such embodiments, the disulfide linkage between the cysteines can be used to constrain the antibody-binding domain if desirable. In some embodiments where the antibody-binding domain is inserted into domain Ib of PE, or into any other portion of the carrier construct, the antibody-binding domain may be flanked by cleavable linkers such that cleavage at the cleavable linkers liberates the antibody-binding domain from the remainder of the construct.

In other embodiments, the antibody-binding domain is connected with the N-terminal or C-terminal end of a polypeptide portion of the carrier construct. In such embodiments, the method of connection should be designed to avoid interference with other functions of the carrier construct, such as receptor-binding or transcytosis. In yet other embodiments, the antibody-binding domain is connected with a side chain of an amino acid of the carrier construct. The antibody-binding domain may be connected with the remainder of the carrier construct with a cleavable linker, as described below. In such embodiments, the antibody-binding domain can be connected with the remainder of the carrier construct with one or more cleavable linkers such that cleavage at the cleavable linker(s) separates the antibody-binding domain from the remainder of the delivery construct. It should be noted that, in certain embodiments, the antibody-binding domain can also comprise a short (1-20 amino acids, preferably 1-10 amino acids, and more preferably 1-5 amino acids) leader peptide in addition to the antibody-binding domain that remains attached to the antibody-binding domain following cleavage of the cleavable linker. Preferably, this leader peptide does not affect the activity or immunogenicity of the antibody-binding domain.

In embodiments where the antibody-binding domain is expressed together with another portion of the carrier construct as a fusion protein, the antibody-binding domain can be can be inserted into the carrier construct by any method known to one of skill in the art without limitation. For example, amino acids corresponding to the antibody-binding domain can be inserted directly into the carrier construct, with or without deletion of native amino acid sequences. In certain embodiments, all or part of the Ib domain of PE can be deleted and replaced with the antibody-binding domain. In certain embodiments, the cysteine residues of the Ib loop are deleted so that the antibody-binding domain remains unconstrained. In other embodiments, the cysteine residues of the Ib loop are linked with a disulfide bond and constrain the antibody-binding domain.

In certain embodiments, the antibody-binding domain is selected to not be cleavable by an enzyme present at the basal-lateral membrane of an epithelial cell. For example, the assays described in the below can be used to routinely test whether such a cleaving enzyme can cleave the antibody-binding domain. If so, the antibody-binding domain can be routinely altered to eliminate the offending amino acid sequence recognized by the cleaving enzyme. The altered antibody-binding domain can then be tested to ensure that it retains activity using methods routine in the art.

5.3.4. Cleavable Linkers

Optionally, the antibody-binding domain of a carrier construct of the invention may be connected with the remainder of the carrier construct with one or more cleavable linkers. The number of cleavable linkers present in the construct depends, at least in part, on the location of the antibody-binding domain in relation to the remainder of the carrier construct and the nature of the antibody-binding domain. When the antibody-binding domain is inserted into the carrier construct, the antibody-binding domain may be flanked by cleavable linkers, such that cleavage at both linkers separates the antibody-binding domain. The flanking cleavable linkers can be the same or different from each other. When the antibody-binding domain can be separated from the remainder of the delivery construct with cleavage at a single linker, the carrier constructs can comprise a single cleavable linker. Further, where the antibody-binding domain is, e.g., a dimer or other multimer, each subunit of the antibody-binding domain can be separated from the remainder of the carrier construct and/or the other subunits of the antibody-binding domain by cleavage at the cleavable linker.

The cleavable linkers are generally cleavable by a cleaving enzyme that is present at or near the basal-lateral membrane of an epithelial cell. By selecting the cleavable linker to be cleaved by such enzymes, the antibody-binding domain can be liberated from the remainder of the construct following transcytosis across the mucous membrane and release from the epithelial cell into the cellular matrix on the basal-lateral side of the membrane. Further, cleaving enzymes could be used that are present inside the epithelial cell, such that the cleavable linker is cleaved prior to release of the construct from the basal-lateral membrane, so long as the cleaving enzyme does not cleave the construct before the construct enters the trafficking pathway in the polarized epithelial cell that results in release of the construct and antibody-binding domain from the basal-lateral membrane of the cell.

In certain embodiments, the cleaving enzyme is a peptidase. In other embodiments, the cleaving enzyme is an RNAse. In yet other embodiments, the cleaving enzyme can cleave carbohydrates. Preferred peptidases include, but are not limited to, Cathepsin GI, Chymotrypsin I, Elastase I, Subtilisin AI, Subtilisin AII, Thrombin I, and Urokinase I. Table 1 presents these enzymes together with an amino acid sequence that is recognized and cleaved by the particular peptidase.

TABLE 1

Peptidases Present Near Basal-Lateral Mucous Membranes

| Peptidase | Amino Acid Sequence Recognized and Cleaved |
|---|---|
| Cathepsin GI | Ala-Ala-Pro-Phe (SEQ ID NO.:4) |
| Chymotrypsin I | Gly-Gly-Phe (SEQ ID NO.:5) |
| Elastase I | Ala-Ala-Pro-Val (SEQ ID NO.:6) |
| Subtilisin AI | Gly-Gly-Leu (SEQ ID NO.:7) |
| Subtilisin AII | Ala-Ala-Leu (SEQ ID NO.:8) |
| Thrombin I | Phe-Val-Arg (SEQ ID NO.:9) |
| Urokinase I | Val-Gly-Arg (SEQ ID NO.:10) |

In certain embodiments, the carrier construct can comprise more than one cleavable linker, wherein cleavage at either cleavable linker can separate the antibody-binding domain to be delivered from the carrier construct. In certain embodiments, the cleavable linker can be selected based on the sequence of the antibody-binding domain to avoid the use of cleavable linkers that comprise sequences present in the antibody-binding domain. For example, if the antibody-binding domain comprises AAL, the cleavable linker can be selected to be cleaved by an enzyme that does not recognize this sequence.

Further, the cleavable linker preferably exhibits a greater propensity for cleavage than the remainder of the carrier construct. As one skilled in the art is aware, many peptide and polypeptide sequences can be cleaved by peptidases and proteases. In certain embodiments, the cleavable linker is selected to be preferentially cleaved relative to other amino acid sequences present in the carrier construct during administration of the delivery construct. In certain embodiments, the receptor-binding domain is substantially (e.g., about 99%, about 95%, about 90%, about 85%, about 80, or about 75%) intact following delivery of the delivery construct to the bloodstream of the subject. In certain embodiments, the translocation domain is substantially (e.g., about 99%, about 95%, about 90%, about 85%, about 80, or about 75%) intact following delivery of the delivery construct to the bloodstream of the subject. In certain embodiments, the macromolecule is substantially (e.g., about 99%, about 95%, about 90%, about 85%, about 80, or about 75%) intact following delivery of the delivery construct to the bloodstream of the subject. In certain embodiments, the cleavable linker is substantially (e.g., about 99%, about 95%, about 90%, about 85%, about 80, or about 75%) cleaved following delivery of the delivery construct to the bloodstream of the subject.

In other embodiments, the cleavable linker is cleaved by a cleaving enzyme found in the plasma of the subject. Any cleaving enzyme known by one of skill in the art to be present in the plasma of the subject can be used to cleave the cleavable linker. Use of such enzymes to cleave the cleavable linkers is less preferred than use of cleaving enzymes found near the basal-lateral membrane of a polarized epithelial cell because it is believed that more efficient cleavage will occur in near the basal-lateral membrane. However, if the skilled artisan determines that cleavage mediated by a plasma enzyme is sufficiently efficient to allow cleavage of a sufficient fraction of the delivery constructs to avoid adverse effects, such plasma cleaving enzymes can be used to cleave the delivery constructs. Accordingly, in certain embodiments, the cleavable linker can be cleaved with an enzyme that is selected from the group consisting of caspase-1, caspase-3, proprotein convertase 1, proprotein convertase 2, proprotein convertase 4, proprotein convertase 4 PACE 4, prolyl oligopeptidase, endothelin cleaving enzyme, dipeptidyl-peptidase IV, signal peptidase, neprilysin, renin, and esterase. See, e.g., U.S. Pat. No. 6,673,574. Table 2 presents these enzymes together with an amino acid sequence(s) recognized by the particular peptidase. The peptidase cleaves a peptide comprising these sequences at the N-terminal side of the amino acid identified with an asterisk.

TABLE 2

Plasma Peptidases

| Peptidase | Amino Acid Sequence Recognized and Cleaved |
| --- | --- |
| Caspase-1 | Tyr-Val-Ala-Asp-Xaa* (SEQ ID NO.:11) |
| Caspase-3 | Asp-Xaa-Xaa-Asp-Xaa* (SEQ ID NO.:12) |
| Proprotein convertase 1 | Arg-(Xaa)$_n$-Arg-Xaa*; n = 0, 2, 4 or 6 (SEQ ID NO.:13) |
| Proprotein convertase 2 | Lys-(Xaa)$_n$-Arg-Xaa*; n = 0, 2, 4, or 6 (SEQ ID NO.:14) |
| Proprotein convertase 4 | Glp-Arg-Thr-Lys-Arg-Xaa* (SEQ ID NO.:15) |
| Proprotein convertase 4 PACE 4 | Arg-Val-Arg-Arg-Xaa* (SEQ ID NO.:16) Decanoyl-Arg-Val-Arg-Arg-Xaa* (SEQ ID NO.:17) |
| Prolyloligopeptidase Endothelin cleaving enzyme in combination with dipeptidyl-peptidase IV | Pro-Xaa*-Trp-Val-Pro-Xaa (SEQ ID NO.:18) |
| Signal peptidase | Trp-Val*-Ala-Xaa (SEQ ID NO.:19) |
| Neprilysin in combination with dipeptidyl-peptidase IV | Xaa-Phe*-Xaa-Xaa (SEQ ID NO.:20) Xaa-Tyr*-Xaa-Xaa (SEQ ID NO.:21) Xaa-Trp*-Xaa-Xaa (SEQ ID NO.:22) |
| Renin in combination with dipeptidyl-peptidase IV | Asp-Arg-Tyr-Ile-Pro-Phe-His-Leu*-Leu-(Val, Ala or Pro)-Tyr-(Ser, Pro, or Ala) (SEQ ID NO.:23) |

Thus, in certain more preferred embodiments, the cleavable linker can be any cleavable linker known by one of skill in the art to be cleavable by an enzyme that is present at the basal-lateral membrane of an epithelial cell. In certain embodiments, the cleavable linker comprises a peptide. In other embodiments, the cleavable linker comprises a nucleic acid, such as RNA or DNA. In still other embodiments, the cleavable linker comprises a carbohydrate, such as a disaccharide or a trisaccharide. In certain embodiments, the cleavable linker is a peptide that comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10).

Alternatively, in less preferred embodiments, the cleavable linker can be any cleavable linker known by one of skill in the art to be cleavable by an enzyme that is present in the plasma of the subject to whom the delivery construct is administered. In certain embodiments, the cleavable linker comprises a peptide. In other embodiments, the cleavable linker comprises a nucleic acid, such as RNA or DNA. In still other embodiments, the cleavable linker comprises a carbohydrate, such as a disaccharide or a trisaccharide. In certain embodiments, the cleavable linker is a peptide that comprises an amino acid sequence that is selected from the group consisting of amino acid sequences presented in Table 2.

In certain embodiments, the carrier construct comprises more than one cleavable linker. In certain embodiments, cleavage at any of the cleavable linkers will separate the antibody-binding domain from the remainder of the carrier construct. In certain embodiments, the carrier construct comprises a cleavable linker cleavable by an enzyme present at the basal-lateral side of a polarized epithelial membrane and a cleavable linkers cleavable by an enzyme that is present in the plasma of the subject to whom the delivery construct is administered.

In certain embodiments, a carrier construct comprises a cleavable linker that is cleavable by one of the following enzymes: cathespin B I, cathespin G I, cathespin G II, cathespin G III, chymotrypsin I, elastase I, elastase II, elastase III, elastase IV, elastase VIII, papain, subtilisin A I, subtilisin A II, thrombin I, thrombin II, and urokinase I. The sequences recognized by these enzymes are well-known in the art. Preferred peptidases exhibit higher activity on the basolateral side of the membrane. Particularly preferred peptidases exhibit much higher (e.g., 100%, 200%, or more increase in activity relative to the apical side) on the basolateral side. Thus, in certain embodiments, the cleavable linker is cleavable by an enzyme that exhibits 50% higher activity on the basal-lateral side of the membrane than on the apical side of the membrane. In certain embodiments, the cleavable linker is cleavable by an enzyme that exhibits 100% higher activity on the basal-lateral side of the membrane than on the apical side of the membrane. In certain embodiments, the cleavable linker is cleavable by an enzyme that exhibits 200% higher activity on the basal-lateral side of the membrane than on the apical side of the membrane. In certain embodiments, the cleavable linker is cleavable by an enzyme that exhibits 500% higher activity on the basal-lateral side of the membrane than on the apical side of the membrane. In certain embodiments, the cleavable linker is cleavable by an enzyme that exhibits 1,000% higher activity on the basal-lateral side of the membrane than on the apical side of the membrane. In certain embodiments, the cleavable linker is cleavable by an enzyme that exhibits 2,000% higher activity on the basal-lateral side of the membrane than on the apical side of the membrane. In certain embodiments, the cleavable linker is cleavable by an enzyme that exhibits 3,000% higher activity on the basal-lateral side of the membrane than on the apical side of the membrane. In certain embodiments, the cleavable linker is cleavable by an enzyme that exhibits 5,000% higher activity on the basal-lateral side of the membrane than on the apical side of the membrane. In certain embodiments, the cleavable linker is cleavable by an enzyme that exhibits 10,000% higher activity on the basal-lateral side of the membrane than on the apical side of the membrane.

Certain enzymes are present in higher concentration or exhibit greater activity in certain epithelial lineages as compared to other epithelial lineages. Thus, the assays described below can be used to test whether the particular epithelial cell lineage through which an antibody will be delivered exhibits the desired cleavage activity. In certain embodiments, the cleavage activity is present in tracheal epithelial cells, but not intestinal epithelial cells. In other embodiments, the cleavage activity is present in intestinal epithelial cells but not tracheal epithelial cells. In certain embodiments, the cleavage activity is present in intestinal epithelial cells and tracheal epithelial cells.

In certain embodiments, the cleavable linker may be cleavable by any enzyme that preferentially cleaves at the basolateral side of an epithelial membrane as compared to the apical side of the membrane. Section 5.13, below, describes an assay that can be used to assess the activity of such enzymes, while Table 3, appended to the end of this document, provides short names and accession numbers for every known human protease or peptidase. Any cleavage sequence recognized by such proteases or peptidases that preferentially cleaves a test substrate on the basolateral side of an epithelial membrane, or in the plasma, as compared to the apical side of such a membrane can also be used in the methods and compositions of the present invention. In such embodiments, one of skill in the art can readily determine the amino acid sequence recognized by such peptidases or proteases according to standard procedures known in the art or according to the known sequences recognized by the proteases and peptidases.

The examples below provide methods for identifying cleaving enzymes that are present at or near the basal-lateral membrane of a polarized epithelial cell. The skilled artisan can routinely use such methods to identify additional cleaving enzymes and the chemical structure(s) identified and cleaved by such cleaving enzymes. Carrier constructs comprising such cleavable linkers are also within the scope of the present invention, whether or not such cleaving enzymes are presented in Table 3.

In other embodiments, the cleavable linker can be a cleavable linker that is cleaved following a change in the environment of the carrier construct. For example, the cleavable linker can be a cleavable linker that is pH sensitive and is cleaved by a change in pH that is experienced when the construct is released from the basal-lateral membrane of a polarized epithelial cell. For instance, the intestinal lumen is strongly alkaline, while plasma is essentially neutral. Thus, a cleavable linker can be a moiety that is cleaved upon a shift from alkaline to neutral pH. The change in the environment of the construct that cleaves the cleavable linker can be any environmental change that that is experienced when the construct is released from the basal-lateral membrane of a polarized epithelial cell known by one of skill in the art, without limitation.

5.4. Antibodies

Any antibody known to one of skill in the art can be used in accordance with the invention. In certain embodiments, an antibody of the invention specifically binds to a tumor antigen, an antigen of a pathogen (e.g., a viral, bacterial or parasitic antigen), an antigen associated with aberrant angiogenesis, an antigen associated with an autoimmune disorder or an antigen associated with an inflammatory disorder. The invention encompasses the use of any antibody known in the art for the treatment, prevention, management and/or amelioration of an autoimmune disorder and/or inflammatory disorder, either alone or combination with one or more additional therapies. Non-limiting examples of such antibodies are presented in Table 4.

TABLE 4

| Antibody Name | Target Antigen | Product Type | Isotype | Source | Indication |
|---|---|---|---|---|---|
| 5G1.1 (Ecluizumab) | Complement (C5) | Humanized | IgG | Alexion Pharm Inc | Rheumatoid Arthritis |
| 5G1.1 (Ecluizumab) | Complement (C5) | Humanized | IgG | Alexion Pharm Inc | SLE |
| 5G1.1 (Ecluizumab) | Complement (C5) | Humanized | IgG | Alexion Pharm Inc | Nephritis |
| 5G1.1-SC (Pexelizumab) | Complement (C5) | Humanized | ScFv | Alexion Pharm Inc | Cardiopulmonary Bypass |
| 5G1.1-SC (Pexelizumab) | Complement (C5) | Humanized | ScFv | Alexion Pharm Inc | Myocardial Infarction |
| 5G1.1-SC (Pexelizumab) | Complement (C5) | Humanized | ScFv | Alexion Pharm Inc | Angioplasty |
| ABX-CBL (Gavilimomab) | CBL | Human | | Abgenix Inc | GvHD |
| ABX-CBL (Gavilimomab) | CD147 | Murine | IgG | Abgenix Inc | Allograft rejection |
| ABX-IL8 | IL-8 | Human | IgG2 | Abgenix Inc | Psoriasis |
| Antegren (Natalizumab) | VLA-4 | Humanized | IgG | Athena/Elan | Multiple Sclerosis |
| Anti-CD11a (Efalizumab) | CD11a | Humanized | IgG1 | Genentech Inc/Xoma | Psoriasis |
| Anti-CD18 | CD18 | Humanized | Fab'2 | Genentech Inc | Myocardial infarction |
| Anti-LFA1 | CD18 | Murine | Fab'2 | Pasteur-Merieux/ Immunotech | Allograft rejection |

TABLE 4-continued

| Antibody Name | Target Antigen | Product Type | Isotype | Source | Indication |
|---|---|---|---|---|---|
| Antova | CD40L | Humanized | IgG | Biogen | Allograft rejection |
| Antova | CD40L | Humanized | IgG | Biogen | SLE |
| BTI-322 | CD2 | Rat | IgG | Medimmune Inc | GvHD, Psoriasis |
| CDP571 | TNF-alpha | Humanized | IgG4 | Celltech | Crohn's |
| CDP571 | TNF-alpha | Humanized | IgG4 | Celltech | Rheumatoid Arthritis |
| CDP850 | E-selectin | Humanized | | Celltech | Psoriasis |
| Corsevin M | Fact VII | Chimeric | | Centocor | Anticoagulant |
| D2E7 (Adalimumab) | TNF-alpha | Human | | CAT/BASF | Rheumatoid Arthritis |
| Humira (Adalimumab) | TNF | Human | IgG1 | Abbott | Rheumatoid Arthritis, Psoriatic Arthritis |
| Hu23F2G (Rovelizumab) | CD11/18 | Humanized | | ICOS Pharm Inc | Multiple Sclerosis |
| Hu23F2G (Rovelizumab) | CD11/18 | Humanized | IgG | ICOS Pharm Inc | Stroke |
| IC14 | CD14 | | | ICOS Pharm Inc | Toxic shock |
| ICM3 | ICAM-3 | Humanized | | ICOS Pharm Inc | Psoriasis |
| IDEC-114 | CD80 | Primatised | | IDEC Pharm/Mitsubishi | Psoriasis |
| IDEC-131 | CD40L | Humanized | | IDEC Pharm/Eisai | SLE |
| IDEC-131 | CD40L | Humanized | | IDEC Pharm/Eisai | Multiple Sclerosis |
| IDEC-151 | CD4 | Primatised | IgG1 | IDEC Pharm/GlaxoSmithKline | Rheumatoid Arthritisth |
| IDEC-152 | CD23 | Primatised | | IDEC Pharm | Asthma/Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 | beta2-integrin | Humanized | IgG | Millennium Inc (LeukoSite Inc.) | Stroke |
| LDP-01 | beta2-integrin | Humanized | IgG | Millennium Inc (LeukoSite Inc.) | Allograft rejection |
| LDP-02 | Alpha4beta7 | Humanized | | Millennium Inc (LeukoSite Inc.) | Ulcerative Colitis |
| MAK-195F (Afelimomab) | TNF alpha | Murine | Fab'2 | Knoll Pharm, BASF | Toxic shock |
| MDX-33 | CD64 (FcR) | Human | | Medarex/Centeon | Autoimmune haematogical disorders |
| MDX-CD4 | CD4 | Human | IgG | Medarex/Eisai/Genmab | Rheumatoid Arthritis |
| MEDI-507 (Siplizumab) | CD2 | Humanized | | Medimmune Inc | Psoriasis |
| MEDI-507 (Siplizumab) | CD2 | Humanized | | Medimmune Inc | GvHD |
| OKT4A | CD4 | Humanized | IgG | Ortho Biotech | Allograft rejection |
| OrthoClone OKT4A | CD4 | Humanized | IgG | Ortho Biotech | Autoimmune disease |
| Remicade (Infliximab) | | | | Amgen | RA |
| Orthoclone/anti-CD3 OKT3 (Muromonab-CD3) | CD3 | Murine | mIgG2a | Ortho Biotech | Allograft rejection |
| ReoPro (Abciximab) | gpIIbIIIa | Chimeric | Fab | Centocor/Lilly | Complications of coronary angioplasty |

The invention encompasses the use of any antibody known in the art for the treatment, prevention, management and/or amelioration of a hyperproliferative disorder, including cancer and non-neoplastic hyperproliferative disorders, either alone or combination with one or more additional therapies. Non-limiting examples of such antibodies and combination therapies are presented in Table 5.

TABLE 5

| Company | Product | Disease | Target |
|---|---|---|---|
| Abgenix | ABX-EGF (Panitimumab) | Cancer | EGF receptor |
| AltaRex | OvaRex (Oregovemab) | ovarian cancer | Tumor antigen CA125 |
|  | BravaRex | Metastatic cancers | Tumor antigen MUC1 |
| Antisoma | Theragyn (pemtumomabytrrium-90) | ovarian cancer | PEM antigen |
|  | Therex | breast cancer | PEM antigen |
| Boehringer Ingelheim | Bivatuzumab | Head & neck cancer | CD44 |
| Centocor/J&J | Panorex (Edrecolomab) | Colorectal cancer | 17-1A |
|  | ReoPro (Abciximab) | PTCA | Gp IIIb/IIIa |
|  | ReoPro (Abciximab) | Acute MI | Gp IIIb/IIIa |
|  | ReoPro (Abciximab) | Ischemic stroke | Gp IIIb/IIIa |
| Corixa | Bexxar (Tositumomab) | NHL | CD20 |
| CRC Technology | MAb, idiotypic 105AD7 | colorectal cancer vaccine | Gp72 |
| Crucell | Anti-EpCAM (Catumaxomab) | Cancer | Ep-CAM |
| Cytoclonal | MAb, lung cancer | non-small cell lung cancer | NA |
| Genentech | Herceptin (Trastuzumab) | metastatic breast cancer | HER-2 |
|  | Herceptin (Trastuzumab) | early stage breast cancer | HER-2 |
|  | Rituxan (Rituximab) | Relapsed/refractory low-grade or follicular NHL | CD20 |
|  | Rituxan (Rituximab) | Intermediate & high-grade NHL | CD20 |
|  | Avastin (Bevacizumab) | NSCLC, metastatic, | VEGF |
|  |  | Colorectal cancer, metastatic | VEGF |
| Genentech | AMD Fab (Ranibizumab) | Age-related macular degeneration | CD18 |
|  | E-26 ($2^{nd}$ gen. IgE) (Omalizumab) | allergic asthma & rhinitis | IgE |
| IDEC | Zevalin (Rituxan + yttrium-90) (Ibritumomab tiuxetan) | Low grade of follicular, relapsed or refractory, CD20-positive, B-cell NHL and Rituximab-refractory NHL | CD20 |
| ImClone | Cetuximab + innotecan | Refractory colorectal carcinoma | EGF receptor |
|  | Cetuximab + cisplatin & radiation | newly diagnosed or recurrent head & neck cancer | EGF receptor |
|  | Cetuximab + gemcitabine | newly diagnosed metastatic pancreatic carcinoma | EGF receptor |

TABLE 5-continued

| Company | Product | Disease | Target |
|---|---|---|---|
| | Cetuximab + cisplatin + 5FU or Taxol (paclitaxel) | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metastases) | EGF receptor |
| | Cetuximab + radiation | locally advanced head & neck carcinoma | EGF receptor |
| | BEC2 + *Bacillus* Calmette Guerin | small cell lung carcinoma | mimics ganglioside GD3 |
| | BEC2 + *Bacillus* Calmette Guerin | Melanoma | mimics ganglioside GD3 |
| | IMC-1C11 | colorectal cancer with liver metasteses | VEGF-receptor |
| ImmonoGen | nuC242-DM1 | Colorectal, gastric, and pancreatic cancer | nuC242 |
| ImmunoMedics | LymphoCide (Epratuzumab) | Non-Hodgkins lymphoma | CD22 |
| | LymphoCide Y-90 (Epratuzumab Y-90)) | Non-Hodgkins lymphoma | CD22 |
| | CEA-Cide (Labetuzumab) | metastatic solid tumors | CEA |
| | CEA-Cide Y-90 (Labetuzumab) | metastatic solid tumors | CEA |
| | CEA-Scan (Tc-99m-labeled arcitumomab) | colorectal cancer (radioimaging) | CEA |
| | CEA-Scan (Tc-99m-labeled arcitumomab) | Breast cancer (radioimaging) | CEA |
| | CEA-Scan (Tc-99m-labeled arcitumomab) | lung cancer (radioimaging) | CEA |
| | CEA-Scan (Tc-99m-labeled arcitumomab) | intraoperative tumors (radioimaging) | CEA |
| | LeukoScan (Tc-99m-labeled sulesomab) | soft tissue infection (radioimaging) | CEA |
| | LymphoScan (Tc-99m-labeled bectumomab) | Lymphomas (radioimaging) | CD22 |
| | AFP-Scan (Tc-99m-labeled) | liver 7 gem-cell cancers (radioimaging) | AFP |
| Intracel | HumaRAD-HN (+ yttrium-90) | head & neck cancer | NA |
| | HumaSPECT (Votumumab) | Colorectal imaging | NA |
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |
| MedImmune | Vitaxin | Cancer | $\alpha v \beta_3$ |
| Merck KGaA | MAb 425 | Various cancers | EGF receptor |
| | IS-IL-2 | Various cancers | Ep-CAM |

TABLE 5-continued

| Company | Product | Disease | Target |
| --- | --- | --- | --- |
| Millennium | Campath (alemtuzumab) | Chronic lymphocytic leukemia | CD52 |
| NeoRx | CD20-streptavidin (+CD20-streptavidin) | Non-Hodgkins lymphoma | CD20 |
| | Avidicin (albumin + NRLU13) | Metastatic cancer | NA |
| Peregrine | Oncolym (+ iodine-131) | Non-Hodgkins lymphoma | HLA-DR 10 beta |
| | Cotara (+ iodine-131) | Unresectable malignant glioma | DNA-associated proteins |
| Pharmacia Corporation | C215 (+ staphylococcal enterotoxin) | Pancreatic cancer | NA |
| | MAb, lung/kidney cancer | lung & kidney cancer | NA |
| | nacolomab tafenatox (C242 + staphylococcal enterotoxin) | colon & pancreatic cancer | NA |
| Protein Design Labs | Nuvion (Visilizumab) | T cell malignancies | CD3 |
| | SMART M195 | AML | CD33 |
| | SMART 1D10 | NHL | HLA-DR antigen |
| Titan | CEAVac | Colorectal cancer, advanced | CEA |
| | TriGem | Metastatic melanoma & small cell lung cancer | GD2-ganglioside |
| | TriAb | metastatic breast cancer | MUC-1 |
| Trilex | CEAVac | Colorectal cancer, advanced | CEA |
| | TriGem | Metastatic melanoma & small cell lung cancer | GD2-ganglioside |
| | TriAb | metastatic breast cancer | MUC-1 |
| Viventia Biotech | NovoMAb-G2 radiolabeled | Non-Hodgkins lymphoma | NA |
| | Monopharm C | colorectal & pancreatic carcinoma | SK-1 antigen |
| | GlioMAb-H (+ gelonin toxin) | glioma, melanoma & neuroblastoma | NA |
| Xoma | Rituxan (Rituximab) | Relapsed/refractory low-grade or follicular NHL | CD20 |
| | Rituxan (Rituximab) | Intermediate & high-grade NHL | CD20 |
| | ING-1 | Adenomcarcinoma | Ep-CAM |

In certain embodiments, the antibodies used in accordance with the invention are useful for the treatment, prevention, management and/or amelioration of metastatic and/or benign tumors. In specific embodiments, the antibodies used in accordance with the invention are useful for the treatment, prevention, management and/or amelioration of breast, ovarian, prostate, bone, liver, lung, colon, pancreatic, kidney, thyroid, skin, brain and/or uterine cancer.

The invention encompasses the use of any antibody known in the art for the treatment, prevention, management and/or amelioration of a pathogen infection (e.g., a viral, bacterial or parasitic infection), either alone or in combination with additional therapies. In particular, the invention encompasses the use of any antibody known in the art for the treatment, prevention, management and/or amelioration of a viral infection, either alone or in combination with additional therapies. Non-limiting examples of antibodies to viral antigens include antibodies to antigens from adenovirdiae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), human respiratory syncytial virus and metapneumovirus (e.g., avian pneumovirus and human metapneumovirus)), picornaviridae (e.g., enterovirus, rhinovirus, hepatovirus (e.g., human hepatits A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment, the antibody specifically binds to HIV gp120, HIV nef, RSV F glycoprotein, RSV G glycoprotein, influenza virus neuraminidase, influenza virus hemagglutinin, HTLV tax, herpes simplex virus glycoprotein (e.g., gB, gC, gD, and gE) or hepatitis B surface antigen. In a specific embodiment, the antibody is Palivizumab (Synagis; MedImmune, Inc.; humanized anti-RSV F monoclonal antibody).

The invention encompasses the use of any antibody known in the art for the treatment, prevention, management and/or amelioration of a bacterial infection, either alone or in combination with additional therapies. Nonlimiting examples of antibodies to bacterial antigens include antibodies to antigens from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, Edwardsiella, *Enterobacter aerogenes, Erwinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, Staphylococcus (e.g., methicillin resistant *Staphylococcus aureus* and *Staphylococcus pyrogenes*), Streptococcus (e.g., *Streptococcus enteritidis, Streptococcus fasciae*, and *Streptococcus pneumoniae*), Vampirovibr Helicobacter family, and Vampirovibrio family.

The invention encompasses the use of any antibody known in the art for the treatment, prevention, management and/or amelioration of a fungal infection, either alone or in combination with additional therapies. Nonlimiting examples of antibodies to fungal antigens include antibodies to antigens from fungus of *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum*, *Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea*, and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii*, zygomycetes, and classes such as Zygomycetes, Ascomycetes, the Basidiomycetes, Deuteromycetes, and Oomycetes.

In certain embodiments, the antibody used in accordance with the invention exerts its effects in the subject's blood. In other embodiments, the antibody used in accordance with the invention exerts its effects in biological compartments of the subject other than the subject's blood. For example, in certain embodiments, the antibody can exert its effects in the lymphatic system. In other embodiments, the antibody can exert its effects in an organ or tissue, such as, for example, the subject's liver, heart, lungs, pancreas, kidney, brain, bone marrow, etc. In such embodiments, the antibody may or may not be present in the blood, lymph, or other biological fluid at detectable concentrations, yet may still accumulate at sufficient concentrations at its site of action to exert a biological effect.

The antibodies of the present invention include, but are not limited to, monoclonal antibodies, synthetic antibodies, polyclonal antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), and epitope-binding fragments of any of the above. In particular, antibodies of the present invention include immunoglobulin molecules and immunologically active portions of immunoglobulin molecules, i.e., molecules that contain an antigen binding site that immunospecifically binds to an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Preferably, the antibodies of the invention are IgG, more preferably, IgG1.

The antibodies of the invention may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice or other animals that express antibodies from human genes.

The antibodies of the present invention may be monospecific, bispecific, trispecific or of greater multispecificity. Multispecific antibodies may immunospecifically bind to different epitopes of a polypeptide or may immunospecifically bind to both a polypeptide as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553.

The antibodies of the invention include derivatives of the antibodies. Standard techniques known to those of skill in the art can be used to introduce mutations in the nucleotide sequence encoding an antibody to be used with the methods of the invention, including, for example, site-directed mutagenesis and PCR-mediated mutagenesis which result in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

The antibodies of the present invention include derivatives that are modified, i.e., by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, synthesis in the presence of tunicamycin, etc. Additionally, the derivative may contain one or more non-classical amino acids.

The present invention also provides antibodies of the invention that comprise a framework region known to those of skill in the art. In certain embodiments, one or more framework regions, preferably, all of the framework regions, of an antibody to be used in the compositions and methods of the invention are human. In certain other embodiments of the invention, the fragment region of an antibody of the invention is humanized. In certain embodiments, the antibody to be used with the methods of the invention is a synthetic antibody, a monoclonal antibody, an intrabody, a chimeric antibody, a human antibody, a humanized chimeric antibody, a humanized antibody, a glycosylated antibody, a multispecific antibody, a human antibody, a single-chain antibody, or a bispecific antibody.

In certain embodiments, an antibody of the invention has a high binding affinity for an antigen. In specific embodiments, an antibody of the invention has an association rate constant or $k_{on}$ rate of about $10^5$ $M^{-1}s^{-1}$ or more, about $5 \times 10^5$ $M^{-1}$ $s^{-1}$ or more, about $10^6$ $M^{-1}s^{-1}$ or more, about $5 \times 10^6$ $M^{-1}s^{-1}$ or more, about $10^7$ $M^{-1}s^{-1}$ or more, about $5 \times 10^7$ $M^{-1}s^{-1}$ or more, about $10^8$ $M^{-1}s^{-1}$ or more, about $5 \times 10^8$ $M^{-1}s^{-1}$ or more, or about $1 \times 10^9$ $M^{-1}s^{-1}$ or more.

In other embodiments, an antibody of the invention has a $k_{off}$ rate for an antigen of about $5 \times 10^{-1}$ $s^{-1}$ or less, about $10^{-1}$ $s^{-1}$ or less, about $5 \times 10^{-2}$ $s^{-1}$ or less, about $10^{-2}$ $s^{-1}$ or less, about $5 \times 10^{-3}$ $s^{-1}$ or less, about $10^{-3}$ $s^{-1}$ or less, about $5 \times 10^{-4}$ $s^{-1}$ or less, about $10^{-4}$ $s^{-1}$ or less, about $5 \times 10^{-5}$ $s^{-1}$ or less, about $10^{-5}$ $s^{-1}$ or less, about $5 \times 10^{-6}$ $s^{-1}$ or less, about $10^{-6}$ $s^{-1}$ or less, about $5 \times 10^{-7}$ $s^{-1}$ or less, about $10^{-7}$ $s^{-1}$ or less, about $5 \times 10^{-8}$ $s^{-1}$ or less, about $10^{-8}$ $s^{-1}$ or less, about $5 \times 10^{-9}$ $s^{-1}$ or less, about $10^{-9}$ $s^{-1}$ or less, about $5 \times 10^{-10}$ $s^{-1}$ or less, or about $10^{-10}$ $s^{-1}$ or less.

In certain embodiments, an antibody of the invention has an affinity constant or $K_a$ ($k_{on}/k_{off}$) for an antigen of about $10^2$ $M^{-1}$ or more, about $5 \times 10^2$ $M^{-1}$ or more, about $10^3$ $M^{-1}$ or more, about $5 \times 10^3$ $M^{-1}$ or more, about $10^4$ $M^{-1}$ or more, about $5 \times 10^4$ $M^{-1}$ or more, about $10^5$ $M^{-1}$ or more, about $5 \times 10^5$ $M^{-1}$ or more, about $10^6$ $M^{-1}$ or more, about $5 \times 10^6$ $M^{-1}$ or more, about $10^7$ $M^{-1}$ or more, about $5 \times 10^7$ $M^{-1}$ or more, about $10^8$ $M^{-1}$ or more, about $5 \times 10^8$ $M^{-1}$ or more, about $10^9$ $M^{-1}$ or more, about $5 \times 10^9$ $M^{-1}$ or more, about $10^{10}$ $M^{-1}$ or more, about $5 \times 10^{10}$ $M^{-1}$ or more, about $10^{11}$ $M^{-1}$ or more, about $5 \times 10^{11}$ $M^{-1}$ or more, about $10^{12}$ $M^{-1}$ or more, about $5 \times 10^{12}$ $M^{-1}$ or more, about $10^{13}$ $M^{-1}$ or more, about $5 \times 10^{13}$ $M^{-1}$ or more, about $10^{14}$ $M^{-1}$ or more, about $5 \times 10^{14}$ $M^{-1}$ or more, about $10^{15}$ $M^{-1}$ or more, or about $5 \times 10^{15}$ $M^{-1}$ or more.

In certain embodiments, an antibody of the invention has a low dissociation constant. In specific embodiments, the antibody-binding domain of a carrier construct of the invention has a dissociation constant or $K_d$ ($k_{off}/k_{on}$) for antibody about $5 \times 10^{-1}$ M or less, about $10^{-1}$ M or less, about $5 \times 10^{-2}$ M or less, about $10^{-2}$ M or less, about $5 \times 10^{-3}$ M or less, about $10^{-3}$ M or less, about $5 \times 10^{-4}$ M or less, about $10^{-4}$ M or less, about $5 \times 10^{-5}$ M or less, about $10^{-5}$ M or less, about $5 \times 10^{-6}$ M or less, about $10^{-6}$ M or less, about $5 \times 10^{-7}$ M or less, about $10^{-7}$ M or less, about $5 \times 10^{-8}$ M or less, about $10^{-8}$ M or less, about $5 \times 10^{-9}$ M or less, about $10^{-9}$ M or less, about $5 \times 10^{10}$ M or less, or about $10^{-10}$ M or less.

In certain embodiments, an antibody of the present invention has a median effective concentration ($EC_{50}$) of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. The median effective concentration is the concentration of antibody that neutralizes 50% of an antigen in an in vitro microneutralization assay.

5.4.1. Antibodies with Increased Half-Life

In certain embodiments of the invention, an antibody of the invention has a half-lives in a subject, preferably a human, of about 12 hours or more, about 1 day or more, about 3 days or more, about 6 days or more, about 10 days or more, about 15 days or more, about 20 days or more, about 25 days or more, about 30 days or more, about 35 days or more, about 40 days or more, about 45 days or more, about 2 months or more, about 3 months or more, about 4 months or more, or about 5 months or more. Antibodies with increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication No. WO 97/34631 and U.S. patent application Ser. No. 10/020,354, entitled "Molecules with Extended Half-Lives, Compositions and Uses Thereof", filed Dec. 12, 2001, by Johnson et al.; and U.S. Publication Nos. 2005/003700 and 2005/0064514, which are incorporated herein by reference in their entireties). Such antibodies can be tested for binding activity to antigens as well as for in vivo efficacy using methods known to those skilled in the art, for example, by immunoassays described herein.

Further, antibodies with increased in vivo half-lives can be generated by attaching to the antibodies polymer molecules such as high molecular weight polyethyleneglycol (PEG). PEG can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatized antibodies can be tested for binding activity to antigens as well as for in vivo efficacy using methods known to those skilled in the art, for example, by immunoassays described herein.

5.4.2. Antibody Conjugates

The present invention also encompasses antibodies that are conjugated or fused to one or more moieties, including but not limited to, peptides, polypeptides, proteins, fusion proteins, nucleic acid molecules, small molecules, mimetic agents, synthetic drugs, inorganic molecules, and organic molecules.

The present invention encompasses antibodies that are recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors.

The present invention further includes compositions comprising heterologous proteins, peptides or polypeptides fused or conjugated to antibody fragments. For example, the heterologous polypeptides may be fused or conjugated to a Fab fragment, Fd fragment, Fv fragment, F(ab)$_2$ fragment, a VH domain, a VL domain, a VH CDR, a VL CDR, or fragment thereof. Methods for fusing or conjugating polypeptides to antibody fragments are well-known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (said references incorporated by reference in their entireties).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment may be recombined with one or more components, motifs, sections, parts, domains, fragments, etc. of one or more heterologous molecules.

In other embodiments, antibodies of the present invention or fragments, analogs or derivatives thereof can be conjugated to a diagnostic or detectable agent. Such antibodies can be useful for monitoring or prognosing the development or progression of a disorder as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, nonradioactive paramagnetic metal ions, and molecules that are radiolabelled or conjugated to specific radioisotopes.

The present invention further encompasses antibodies that are conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), Auristatin molecules (e.g., auristatin PHE, bryostatin 1, and solastatin 10; see Woyke et al., 2002, Antimicrob. Agents Chemother. 46:3802-8; Woyke et al., 2001, Antimicrob. Agents Chemother. 45:3580-4; Mohammad et al., 2001, Anticancer Drugs 12:735-40; Wall et al., 1999, Biochem. Biophys. Res. Commun. 266:76-80; Mohammad et al., 1999, Int. J. Oncol. 15:367-72; all of which are incorporated herein by reference), hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantaijian et al., 2002, Clin Cancer Res. 8(7):2167-76), cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, procaine, tetracaine, lidocaine, propranolol, and puromycin and analogs or homologs thereof) and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459), farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305), topoisomerase inhibitors (e.g., camptothecin; irinotecan; SN-38; topotecan; 9-aminocamptothecin; GG-211 (GI 147211); DX-895 If; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin) and pharmaceutically acceptable salts, solvates, clathrates, and prodrugs thereof. See, e.g., Rothenberg, 1997, *Annals of Oncology* 8:837-855; and Moreau et al., 1998, *J. Med. Chem.* 41:1631-1640; antisense oligonucleotides (e.g., those disclosed in the U.S. Pat. Nos. 6,277,832, 5,998,596, 5,885,834, 5,734,033, and 5,618,709), immunomodulators (e.g., antibodies and cytokines), antibodies, and adenosine deaminase inhibitors (e.g., Fludarabine phosphate and 2-Chlorodeoxyadenosine).

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNFα, TNFβ, AIM I (see, International publication No. WO 97/33899), AIM II (see, International Publication No. WO 97/34911), Fas Ligand (Takahashi et al., 1994, J. Immunol., 6:1567-1574), and VEGI (see, International publication No. WO 99/23105), a thrombotic agent or an anti-angiogenic agent, e.g., angiostatin, endostatin or a component of the coagulation pathway (e.g., tissue factor); or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, fibrinopeptides A and B from the α and β chains of fibrinogen, fibrin monomer).

Moreover, an antibody can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, and $^{131}$Sm, to polypeptides. In certain embodiments, the macrocyclic chelator is 1,4,7,10-tetraazacyclododecane-N,N',N'',N'''-tetra-acetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an antibody or fragment thereof should be chosen to achieve the desired prophylactic or therapeutic effect(s) for a particular disorder in a subject. A clinician or other medical personnel should consider the following when deciding on which therapeutic moiety or drug to conjugate to an antibody or fragment thereof: the nature of the disease, the severity of the disease, and the condition of the subject.

5.5. Fusion Proteins Comprising an Antibody Fragment

Any fusion protein comprising a bioactive molecule and an antibody or antibody fragment may be used in accordance with the invention. In one embodiment, the fusion proteins comprise a bioactive molecule and an antibody. In another embodiment, fusion proteins comprising a bioactive molecule and an epitope-binding fragment (e.g., a VH chain, VH domain, VH complementarity determining region (CDR), VL chain, VL domain, VLCDR, F(ab')2, and scFv) can be used in accordance with the invention. In another embodiment, fusion proteins comprising a bioactive molecule and an Fc region of an antibody or a fragment thereof can be used in accordance with the invention. In another embodiment, fusion proteins comprising a bioactive molecule and the CH2 and/or CH3 region(s) of an antibody can be used in accordance with the invention. In another embodiment, fusion proteins comprising a bioactive molecule and the CH2 and CH3 and hinge regions of an antibody can be used in accordance with the invention. In another embodiment, fusion proteins comprising a bioactive molecule and the CH1 region of an antibody can be used in accordance with the invention. In yet another embodiment, fusion proteins comprising a CH1 and CH2 and/or CH3 regions of an antibody can be used in accordance with the invention. Preferably, the fusion proteins of the invention have a prophylactic and/or therapeutic effect.

The bioactive molecules of the fusion proteins elicit and/or reduce a biological response(s) as measured in vitro and/or in vivo. In a specific embodiment, the bioactive molecules of the fusion proteins bind to a target antigen and elicit a biological response(s). In another embodiment, the bioactive molecules bind to a target antigen and reduce or inhibit a biological response(s). The bioactive molecule can be any molecule that elicits and/or reduces a biological response(s), including, but not limited to, peptides, polypeptides, proteins, nucleic acids, polysaccharides, lipids, inorganic molecules, organic molecules and any combination thereof.

In a specific embodiment, a fusion protein comprises an extracellular domain of a cellular receptor and an antibody fragment (e.g., the Fc region of an antibody or a fragment thereof). Non-limiting examples of cellular receptors that comprise an extracellular domain that can be used to produce such fusion proteins include CTLA-4, LFA-3, TNFR, EGFR, Ephs, Ephrins, CD2, CD3, etc.

The invention encompasses the use of any of fusion protein comprising a bioactive molecule and an antibody fragment known in the art for the treatment, prevention, management and/or amelioration of an autoimmune disorder, an inflammatory disorder, a hyperproliferative disorder (e.g., cancer and non-neoplastic hyperproliferative conditions), and/or pathogen infections, either alone or in combination with additional therapies. Nonlimiting examples of fusion proteins that can be used in accordance with the invention include those presented in Table 6.

In certain embodiments of the invention, the fusion proteins of the invention have half-lives in a subject, preferably a human, of about 12 hours or more, about 1 day or more, about 3 days or more, about 6 days or more, about 10 days or more, about 15 days or more, about 20 days or more, about 25 days or more, about 30 days or more, about 35 days or more, about 40 days or more, about 45 days or more, about 2 months or more, about 3 months or more, about 4 months or more, or about 5 months or more. Fusion proteins with increased in vivo half-lives can be generated by techniques known to those of skill in the art. For example, the techniques described in Section 5.4.1, supra, with respect to antibodies, can be used to generate fusion proteins with increased in vivo half-lives.

In certain embodiments, the fusion proteins comprise a bioactive molecule, an antibody fragment and a diagnostic or detectable agent. Such fusion proteins can be useful for monitoring or prognosing the development or progression of a disorder as part of a clinical testing procedure, such as determining the efficacy of a particular therapy. Non-limiting examples of diagnostic and detectable agents which can be used are described in Section 5.4.2, supra.

In certain embodiments, the fusion proteins comprise a bioactive molecule, an antibody fragment and a therapeutic moiety or drug moiety. Such fusion proteins can be useful in delivering a therapeutic moiety or drug moiety to a target cell. Non-limiting examples of therapeutic moieties and drug moieties which can be used are described in Section 5.4.2, supra.

5.6. Methods for Delivering an Antibody or Fusion Protein

In another aspect, the invention provides methods for local or systemic delivery of an antibody or fusion protein comprising a bioactive molecule and an antibody or antibody fragment to a subject. These methods generally comprise administering a delivery construct of the invention to a mucous membrane of the subject to whom the antibody or fusion protein is delivered. The delivery construct is typically administered in the form of a pharmaceutical composition, as described below.

TABLE 6

| Product | Construct | Product Type | Isotype | Company | Indication |
|---|---|---|---|---|---|
| Enbrel (Etanercept) | TNFR extracellular domain fused to Fc region | Human | IgG1 | Amgen | Rheumatoid Arthritis, Juvenile Rheumatoid Arthritis, Psoriatic Arthritis, Ankylosing Spondylitis, Psoriasis |
| LFA3-TIP (Alefacept) | First extracellular domain of LFA-3 fused to the hinge, CH2, and CH3 domains of human IgG1 | Human | IgG1 | Biogen | Psoriasis |
| Abatacept (Orencia) | CTLA4 extracellular domain fused to heavy chain constant region of IgG1 | Human | IgG1 | Bristol Myers Squibb | Rheumtoid Arthtitis |

Thus, in certain aspects, the invention provides a method for delivering an antibody or a fusion protein comprising a bioactive molecule and an antibody or antibody fragment to a subject. The method comprises contacting an apical surface of a polarized epithelial cell of the subject with a delivery construct of the invention. In certain embodiments, the delivery construct comprises an antibody and a carrier construct comprising a receptor-binding domain, a transcytosis domain, and an antibody-binding domain to which the antibody non-covalently binds. In other embodiments, the delivery construct comprises a fusion protein comprising a bioactive molecule and an antibody or antibody fragment, and a carrier construct, wherein the carrier construct comprises a receptor-binding domain, a transcytosis domain, and an antibody-binding domain to which the antibody fragment of the fusion protein non-covalently binds.

The invention also provides methods for local or systemic delivery of an antibody or a fusion protein comprising a bioactive molecule and an antibody or antibody fragment to a subject, the methods comprising administering concurrently a carrier construct of the invention and an antibody or a fusion protein of the invention to a mucous membrane of the subject to whom the antibody or the fusion protein is delivered. In this context, the term concurrently refers to the administration of the carrier construct and the antibody or fusion protein within about 1 minute, about 2 minutes, about 5 minutes, about 10 minutes, about 15 minutes, about 30 minutes, about 60 minutes, about 90 minutes, about 2 hours, about 4 hours, about 6 hours, about 10 hours, about 12 hours or within about 24 hours of each other. In a preferred embodiment, the carrier construct and the antibody or fusion protein are administered to each other within one doctor's visit. The carrier construct and antibody or fusion protein are typically administered in the form of a pharmaceutical composition, as described below. Any method of administration known to one skill in the art can be used to administer a carrier construct and an antibody or fusion protein of the invention, see, e.g., those in Section 5.5.1, infra.

The transcytosis domain can transcytose the antibody or fusion protein to and through the basal-lateral membrane of said epithelial cell. Optionally, the carrier construct further comprises a cleavable linker. The cleavable linker can be cleaved by an enzyme that is present at a basal-lateral membrane of a polarized epithelial cell of the subject or in the plasma of the subject. Cleavage at the cleavable linker separates the antibody-binding domain from the remainder of the carrier construct, thereby delivering the a complex of the antibody-binding domain-antibody or the antibody-binding domain-fusion protein to the subject.

In certain embodiments, the enzyme that is present at or near a basal-lateral membrane of a polarized epithelial cell is selected from the group consisting of Cathepsin GI, Chymotrypsin I, Elastase I, Subtilisin AI, Subtilisin AII, Thrombin I, and Urokinase I. In certain embodiments, the cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.: 10).

In certain embodiments, the receptor-binding domain is selected from the group consisting of receptor-binding domains from *Pseudomonas* exotoxin A, cholera toxin, diptheria toxin, shiga toxin, or shiga-like toxin; monoclonal antibodies; polyclonal antibodies; single-chain antibodies; TGF α; EGF; IGF-I; IGF-II; IGF-III; IL-1; IL-2; IL-3; IL-6; MIP-1a; MIP-1b; MCAF; and IL-8. In certain embodiments, the receptor-binding domain binds to a cell surface receptor selected from the group consisting of α2-macroglobulin receptor, EGFR, IGFR, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor.

In certain embodiments, the transcytosis domain is selected from the group consisting of transcytosis domains from *Pseudomonas* exotoxin A, diptheria toxin, pertussis toxin, cholera toxin, heat-labile *E. coli* enterotoxin, shiga toxin, and shiga-like toxin.

In certain embodiments, the invention provides a method for delivering an antibody or a fusion protein comprising a bioactive molecule and an antibody or antibody fragment to the bloodstream of a subject that results in at least about 30% bioavailability of the antibody or the fusion protein, comprising administering a delivery construct comprising the antibody or the fusion protein comprising a bioactive molecule and an antibody or antibody fragment non-covalently bound to a carrier construct to the subject, thereby delivering at least about 30% of the total antibody or the total fusion protein administered to the blood of the subject in a bioavailable form of the antibody. In certain embodiments, at least about 10% of the total antibody or the total fusion protein administered is bioavailable to the subject. In certain embodiments, at least about 15% of the total antibody or the total fusion protein administered is bioavailable to the subject. In certain embodiments, at least about 20% of the total antibody or the total fusion protein administered is bioavailable to the subject. In certain embodiments, at least about 25% of the total antibody or the total fusion protein administered is bioavailable to the subject. In certain embodiments, at least about 35% of the total antibody or the total fusion protein administered is bioavailable to the subject. In certain embodiments, at least about 40% of the total antibody or the total fusion protein administered is bioavailable to the subject. In certain embodiments, at least about 45% of the total antibody or the total fusion protein administered is bioavailable to the subject. In certain embodiments, at least about 50% of the total antibody or the total fusion protein administered is bioavailable to the subject. In certain embodiments, at least about 55% of the total antibody or the total fusion protein administered is bioavailable to the subject. In certain embodiments, at least about 60% of the total antibody or the total fusion protein administered is bioavailable to the subject. In certain embodiments, at least about 65% of the total antibody or the total fusion protein administered is bioavailable to the subject. In certain embodiments, at least about 70% of the total antibody or the total fusion protein administered is bioavailable to the subject. In certain embodiments, at least about 75% of the total antibody or the total fusion protein administered is bioavailable to the subject. In certain embodiments, at least about 80% of the total antibody or the total fusion protein administered is bioavailable to the subject. In certain embodiments, at least about 85% of the total antibody or the total fusion protein administered is bioavailable to the subject. In certain embodiments, at least about 90% of the total antibody or the total fusion protein administered is bioavailable to the subject. In certain embodiments, at least about 95% of the total antibody or the total fusion protein administered is bioavailable to the subject.

In certain embodiments, the percentage of bioavailability of the antibody or fusion protein is determined by comparing the amount of antibody or fusion protein present in a subject's blood following administration of a delivery construct comprising the antibody or fusion protein to the amount of antibody or fusion protein present in a subject's blood following administration of the antibody or fusion protein through another route of administration. In certain embodiments, the other route of administration is injection, e.g., subcutaneous injection, intravenous injection, intra-arterial injection, etc. In other embodiments, the percentage of bioavailability of the antibody or fusion protein is determined by comparing the amount of antibody or fusion protein present in a subject's blood following administration of a delivery construct comprising the antibody or fusion protein to the total amount of antibody or fusion protein administered as part of the delivery construct.

In certain embodiments, peak plasma concentrations of the delivered antibody or fusion protein in the subject are achieved about 10 minutes after administration. In certain embodiments, peak plasma concentrations of the delivered antibody or fusion protein in the subject are achieved about 15 minutes after administration. In certain embodiments, peak plasma concentrations of the delivered antibody or fusion protein in the subject are achieved about 5 minutes after administration. In certain embodiments, peak plasma concentrations of the delivered antibody or fusion protein in the subject are achieved about 20 minutes after administration. In certain embodiments, peak plasma concentrations of the delivered antibody or fusion protein in the subject are achieved about 25 minutes after administration. In certain embodiments, peak plasma concentrations of the delivered antibody or fusion protein in the subject are achieved about 30 minutes after administration. In certain embodiments, peak plasma concentrations of the delivered antibody or fusion protein in the subject are achieved about 35 minutes after administration. In certain embodiments, peak plasma concentrations of the delivered antibody or fusion protein in the subject are achieved about 40 minutes after administration. In certain embodiments, peak plasma concentrations of the delivered antibody or fusion protein in the subject are achieved about 45 minutes after administration. In certain embodiments, peak plasma concentrations of the delivered antibody or fusion protein in the subject are achieved about 50 minutes after administration. In certain embodiments, peak plasma concentrations of the delivered antibody or fusion protein in the subject are achieved about 55 minutes after administration. In certain embodiments, peak plasma concentrations of the delivered antibody or fusion protein in the subject are achieved about 60 minutes after administration. In certain embodiments, peak plasma concentrations of the delivered antibody or fusion protein in the subject are achieved about 90 minutes after administration. In certain embodiments, peak plasma concentrations of the delivered antibody or fusion protein in the subject are achieved about 120 minutes after administration.

In certain embodiments, the peak plasma concentration of the delivered antibody or fusion protein is between about 0.01 ng/ml plasma and about 800 µg/ml plasma. In certain embodiments, the peak plasma concentration of the delivered antibody or fusion protein is between about 0.01 ng/ml plasma and about 200 µg/ml plasma. In certain embodiments, the peak plasma concentration of the delivered antibody or fusion protein is between about 0.01 ng/ml plasma and about 100 µg/ml plasma. In certain embodiments, the peak plasma concentration of the delivered antibody or fusion protein is between about 0.01 ng/ml plasma and about 50 µg/ml plasma. In certain embodiments, the peak plasma concentration of the delivered antibody or fusion protein is between about 1 ng/ml plasma and about 0.1 µg/ml plasma. In certain embodiments, the peak plasma concentration of the delivered antibody or fusion protein is between about 1 ng/ml plasma and about 1 µg/ml plasma. In certain embodiments, the peak plasma concentration of the delivered antibody or fusion protein is between about 1 ng/ml plasma and about 0.5 µg/ml plasma. In certain embodiments, the peak plasma concentration of the delivered antibody or fusion protein is between about 1 ng/ml plasma and about 1 µg/ml plasma. In certain embodiments, the peak plasma concentration of the delivered antibody or fusion protein is between about 10 ng/ml plasma and about 1 µg/ml plasma. In certain embodiments, the peak plasma concentration of the delivered antibody or fusion protein is between about 10 ng/ml plasma and about 0.5 µg/ml plasma.

In certain embodiments, the peak plasma concentration of the delivered antibody or fusion protein is at least about 10 µg/ml plasma. In certain embodiments, the peak plasma concentration of the delivered antibody or fusion protein is at least about 5 µg/ml plasma. In certain embodiments, the peak plasma concentration of the delivered antibody or fusion protein is at least about 1 µg/ml plasma. In certain embodiments, the peak plasma concentration of the delivered antibody or fusion protein is at least about 500 ng/ml plasma. In certain embodiments, the peak plasma concentration of the delivered antibody or fusion protein is at least about 250 ng/ml plasma. In certain embodiments, the peak plasma concentration of the delivered antibody or fusion protein is at least about 100 ng/ml plasma. In certain embodiments, the peak plasma concentration of the delivered antibody or fusion protein is at least about 50 ng/ml plasma. In certain embodiments, the peak plasma concentration of the delivered antibody or fusion protein is at least about 10 ng/ml plasma. In certain embodiments, the peak plasma concentration of the delivered antibody or fusion protein is at least about 5 ng/ml plasma. In certain embodiments, the peak plasma concentration of the delivered antibody or fusion protein is at least about 1 ng/ml plasma. In certain embodiments, the peak plasma concentration of the delivered antibody or fusion protein is at least about 0.1 ng/ml plasma.

Moreover, without intending to be bound to any particular theory or mechanism of action, it is believed that oral administration of a delivery construct can deliver a higher effective concentration of the delivered antibody or fusion protein to the liver of the subject than is observed in the subject's plasma. "Effective concentration," in this context, refers to the concentration experienced by targets of the antibody or fusion protein and can be determined by monitoring and/or quantifying downstream effects of antibody-target interactions or fusion protein-target interactions. While still not bound to any particular theory, it is believed that oral administration of the delivery construct results in absorption of the delivery construct through polarized epithelial cells of the digestive mucosa, e.g., the intestinal mucosa, followed by release of the antibody or fusion protein at the basolateral side of the mucous membrane. As one of skill in the art will recognize, the blood at the basolateral membrane of such digestive mucosa is carried from this location to the liver via the portal venous system. Thus, when the antibody or fusion protein exerts a biological activity in the liver, the antibody or fusion protein is believed to exert an effect in excess of what would be expected based on the plasma concentrations observed in the subject. Accordingly, in certain embodiments, the invention provides a method of administering an antibody or a fusion protein comprising a bioactive molecule and an antibody fragment to a subject that comprises orally administering a delivery construct comprising the antibody or fusion protein to the subject, wherein the antibody or fusion protein is delivered to the subject's liver at a higher effective concentration than observed in the subject's plasma.

In certain embodiments, the epithelial cell is selected from the group consisting of nasal epithelial cells, oral epithelial cells, intestinal epithelial cells, rectal epithelial cells, vaginal epithelial cells, and pulmonary epithelial cells.

In certain embodiments, the subject is a mammal. In further embodiments, the subject is a rodent, a lagomorph, or a primate. In yet further embodiments, the rodent is a mouse or rat. In other embodiments, the lagomorph is a rabbit. In still other embodiments, the primate is a human, monkey, or ape. In a preferred embodiment, the subject is a human.

In another aspect, the present invention provides methods for delivery an antibody or a fusion protein to a subject, said methods comprising administering to said subject an effective amount of a delivery construct of the invention, wherein the effective amount of the delivery construct achieves a serum titer of the antibody or the fusion protein of about 0.1 µg/ml to about 800 µg/ml, such as between 0.1 µg/ml and 500 µg/ml, 0.1 µg/ml and 250 µg/ml, 0.1 µg/ml and 100 µg/ml, 0.1 µg/ml and 50 µg/ml, 0.1 µg/ml and 25 µg/ml or 0.1 µg/ml and 10 µg/ml in the subject. In a specific embodiment, the invention provides methods for delivery an antibody or a fusion protein to a human subject, said methods comprising administering to said subject an effective amount of a delivery construct of the invention, wherein the effective amount of the delivery construct is the amount of the delivery construct that achieves a serum titer of the antibody or the fusion protein of about 0.1 µg/ml to about 800 µg/ml, such as between 0.1 µg/ml and 500 µg/ml, 0.1 µg/ml and 250 µg/ml, 0.1 µg/ml and 100 µg/ml, 0.1 µg/ml and 50 µg/ml, 0.1 µg/ml and 25 µg/ml or 0.1 µg/ml and 10 µg/ml in a non-human subject. In another embodiment, the invention provides methods for delivery an antibody or a fusion protein to a human subject, said methods comprising administering to said subject an effective amount of a delivery construct of the invention, wherein the effective amount of the delivery construct is the amount of the delivery construct that achieves a serum titer of the antibody or the fusion protein of about 0.1 µg/ml to about 800 µg/ml, such as between 0.1 µg/ml and 500 µg/ml, 0.1 µg/ml and 250 µg/ml, 0.1 µg/ml and 100 µg/ml, 0.1 µg/ml and 50 µg/ml, 0.1 µg/ml and 25 µg/ml or 0.1 µg/ml and 10 µg/ml in the subject.

In certain embodiments, the serum titer referenced preceding paragraph is achieved about 10 minutes after administration of the delivery construct. In certain embodiments, the serum titer referenced preceding paragraph is achieved about 15 minutes after administration of the delivery construct. In certain embodiments, the serum titer referenced preceding paragraph is achieved about 30 minutes after administration of the delivery construct. In certain embodiments, the serum titer referenced preceding paragraph is achieved about 60 minutes after administration of the delivery construct. In certain embodiments, the serum titer referenced preceding paragraph is achieved about 90 minutes after administration of the delivery construct. In certain embodiments, the serum titer referenced preceding paragraph is achieved about 120 minutes after administration of the delivery construct. In certain embodiments, the serum titer referenced preceding paragraph is achieved about 6 hours after administration of the delivery construct. In certain embodiments, the serum titer referenced preceding paragraph is achieved about 12 minutes after administration of the delivery construct. In certain embodiments, the serum titer referenced preceding paragraph is achieved about 24 minutes after administration of the delivery construct. In certain embodiments, the serum titer referenced preceding paragraph is achieved about 72 hours after administration of the delivery construct.

In another aspect, the invention provides a method for delivering an antibody or fusion protein comprising a bioactive molecule and an antibody or antibody fragment to the bloodstream of a subject that induces a lower titer of antibodies against the antibody or fusion protein than other routes of administration. Without intending to be bound by any particular theory or mechanism of action, it is believed that entry of the antibody or fusion protein through a mucous membrane, e.g., through the intestinal mucosa, causes the immune system to tolerate the antibody or fusion protein better than if the antibody or fusion protein were, for example, injected. Thus, a lower titer of antibodies against the antibody or fusion protein can be produced in the subject by delivering the antibody or fusion protein with a delivery construct of the invention through the mucosa rather than injecting the antibody or fusion protein, for example, subcutaneously, intravenously, intra-arterially, intraperitoneally, or otherwise.

Accordingly, in certain embodiments, the invention provides a method for delivering an antibody or a fusion protein comprising a bioactive molecule and an antibody or antibody fragment to the bloodstream a subject that comprises contacting a delivery construct of the invention that comprises the antibody or fusion protein to be delivered to an apical surface of a polarized epithelial cell of the subject, such that the antibody or fusion protein is administered to the bloodstream of the subject, wherein a lower titer of antibodies specific for the antibody or fusion protein is induced in the serum of the subject than is induced by subcutaneously administering the antibody or fusion protein separately from the remainder of the delivery construct to a subject.

In certain embodiments, the titer of antibodies specific for the antibody or fusion protein induced in the serum of the subject by the antibody or fusion protein delivered by the delivery construct is less than about 95% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 90% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 85% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 80% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 75% of the titer of antibodies induced by subcutaneously administering the antibody or fusion protein separately from the remainder of the delivery construct.

In certain embodiments, the titer of antibodies specific for the antibody or fusion protein induced in the serum of the subject by the antibody or fusion protein delivered by the delivery construct is less than about 70% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 65% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 60% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 55% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 55% of the titer of antibodies induced by subcutaneously administering the antibody or fusion protein separately from the remainder of the delivery construct.

In certain embodiments, the titer of antibodies specific for the antibody or fusion protein induced in the serum of the subject by the antibody or fusion protein delivered by the delivery construct is less than about 50% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 45% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 40% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 35% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 30% of the titer of antibodies induced by subcutaneously administering the antibody or fusion protein separately from the remainder of the delivery construct.

In certain embodiments, the titer of antibodies specific for the antibody or fusion protein induced in the serum of the subject by the antibody or fusion protein delivered by the delivery construct is less than about 25% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than 20% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 15% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 10% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 5% of the titer of antibodies induced by subcutaneously administering the antibody or fusion protein separately from the remainder of the delivery construct. In certain embodiments, the titer of antibodies specific for the antibody or fusion protein induced in the serum of the subject by the antibody or fusion protein delivered by the delivery construct is less than about 1% of the titer of antibodies induced by subcutaneously administering the antibody or fusion protein separately from the remainder of the delivery construct.

The present invention provides methods for preventing, treating, managing and ameliorating a disorder in a subject, the methods comprising administering to the subject a delivery construct of the invention. In accordance with the invention, a delivery construct can be administered alone or in combination with another therapy(ies). The use of the term "in combination" does not restrict the order in which therapies are administered to a subject. A first therapy (e.g., a delivery construct) can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject. Any additional therapy can be administered in any order with the other additional therapies. Non-limiting examples of therapies that can be administered in combination with an antibody of the invention include analgesic agents, anesthetic agents, antibiotics, or immunomodulatory agents or any other agent listed in the *U.S. Pharmacopoeia* and/or *Physician's Desk Reference.*

5.6.1. Methods of Administration

The delivery constructs of the invention can be administered to a subject by any method known to one of skill in the art. In certain embodiments, the delivery constructs are contacted to a mucosal membrane of the subject. For example, the mucosal membrane can be present in the eye, nose, mouth, trachea, lungs, esophagus, stomach, small intestine, large intestine, rectum, anus, sweat glands, vulva, vagina, or penis of the subject. Preferably, the mucosal membrane is a mucosal membrane present in the digestive tract of the subject, such as a mucosal membrane in the mouth, esophagus, stomach, small intestine, large intestine, or rectum of the subject.

In such embodiments, the delivery constructs are preferably administered to the subject orally. Thus, the delivery construct can be formulated to protect the delivery construct from degradation in the acid environment of the stomach, if necessary. For example, many embodiments of the delivery constructs of the invention comprise polypeptide domains with defined activities. Unless such delivery constructs are protected from acid and/or enzymatic hydrolysis in the stomach, the constructs will generally be digested before delivery of substantial amounts of the macromolecule to be delivered. Accordingly, composition formulations that protect the delivery construct from degradation can be used in administration of these delivery constructs.

5.6.2. Dosage

Generally, a pharmaceutically effective amount of the delivery construct of the invention is administered to a subject. The skilled artisan can readily determine if the dosage of the delivery construct is sufficient to deliver an effective amount of the antibody or the fusion protein comprising a bioactive molecule and an antibody fragment, as described below. In certain embodiments, between about 1 µg and about 1 g of delivery construct is administered. In other embodiments, between about 10 µg and about 500 mg of delivery construct is administered. In still other embodiments, between about 10 µg and about 100 mg of delivery construct is administered. In yet other embodiments, between about 10 µg and about 1000 µg of delivery construct is administered. In still other embodiments, between about 10 µg and about 250 µg of delivery construct is administered. In yet other embodiments, between about 10 µg and about 100 µg of delivery construct is administered. Preferably, between about 10 µg and about 50 µg of delivery construct is administered.

The volume of a composition comprising the delivery construct that is administered will generally depend on the concentration of delivery construct and the formulation of the composition. In certain embodiments, a unit dose of the delivery construct composition is between about 0.05 ml and about 1 ml, preferably about 0.5 ml. The delivery construct compositions can be prepared in dosage forms containing between 1 and 50 doses (e.g., 0.5 ml to 25 ml), more usually between 1 and 10 doses (e.g., 0.5 ml to 5 ml).

The delivery construct compositions of the invention can be administered in one dose or in multiple doses. A dose can be followed by one or more doses spaced by about 1 to about 6 hours, by about 6 to about 12 hours, by about 12 to about 24 hours, by about 1 day to about 3 days, by about 1 day to about 1 week, by about 1 week to about 2 weeks, by about 2 weeks to about 1 month, by about 4 to about 8 weeks, by about 1 to about 3 months, or by about 1 to about 6 months.

The antibodies and fusion proteins comprising antibody fragments to be delivered are generally antibodies and fusion proteins for which a large amount of knowledge regarding dosage, frequency of administration, and methods for assessing effective concentrations in subjects has accumulated. Such knowledge can be used to assess efficiency of delivery, effective concentration of the antibody or fusion protein in the subject, and frequency of administration. Thus, the knowledge of those skilled in the art can be used to determine whether, for example, the amount of antibody or fusion protein delivered to the subject is an effective amount, the dosage should be increased or decreased, the subject should be administered the delivery construct more or less frequently, and the like.

5.6.3. Determining Amounts of Antibody or Fusion Protein Delivered

The methods of the invention can be used to deliver, either locally or systemically, a pharmaceutically effective amount of an antibody or a fusion protein comprising a bioactive molecule and an antibody or antibody fragment to a subject. The skilled artisan can determine whether the methods result in delivery of such a pharmaceutically effective amount of the antibody or fusion protein. The exact methods will depend on the antibody or fusion protein that is delivered, but generally will rely on either determining the concentration of the antibody or fusion protein in the blood of the subject or in the biological compartment of the subject where the antibody or fusion protein exerts its effects. Alternatively or additionally, the effects of the antibody or fusion protein on the subject can be monitored.

Any effect of an antibody or a fusion protein comprising a bioactive molecule and an antibody or antibody fragment that is administered that is known by one of skill in the art, without limitation, can be assessed in determining whether an effective amount of the antibody or fusion protein has been administered. Exemplary effects include, but are not limited to, receptor-binding, receptor activation, downstream effects of receptor-binding, downstream effects of receptor activation, coordination of compounds, effective blood clotting, bone growth, wound healing, cellular proliferation, etc. The exact effect that is assessed will depend on the antibody or fusion protein that is delivered.

In a specific embodiment, the skilled artisan can determine whether a pharmaceutically effective amount of an antibody or a fusion protein comprising a bioactive molecule and an antibody or antibody fragment has been delivered to the subject by, for example, taking a plasma sample from the subject and determining the concentration of the antibody or fusion protein therein. One exemplary method for determining the concentration of the antibody or the fusion protein is by performing an ELISA assay, but any other suitable assay known to the skilled artisan can be used.

5.7. Diagnostic Uses of Delivery Constructs

The delivery constructs of the invention can be used for diagnostic purposes to detect, diagnose, or monitor disorders. In a specific embodiment, diagnosis comprises: a) administering (for example, orally) to a subject an effective amount of a delivery construct of the invention comprising a labeled antibody or a labeled fusion protein; b) waiting for a time interval following the administration for permitting the labeled antibody or labeled fusion protein to preferentially concentrate at sites in the subject where the antigen of interest is expressed (and for unbound labeled antibody or labeled fusion protein to be cleared to background level); c) determining background level; and d) detecting the labeled antibody or labeled fusion protein in the subject, such that detection of labeled antibody or labeled fusion protein above the background level indicates that the subject has the disorder. In accordance with this embodiment, the antibody or fusion protein is labeled with an imaging moiety which is detectable using an imaging system known to one of skill in the art. Background level can be determined by various methods including, comparing the amount of labeled antibody or labeled fusion protein detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or labeled fusion protein will then preferentially accumulate at the location of cells which contain the specific protein. In vivo tumor imaging is described in S. W. Burchiel et al., "Immunopharmacokinetics of Radiolabeled Antibodies and Their Fragments," Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody or labeled fusion protein to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disorder is carried out by repeating the method for diagnosing the disorder, for example, one month after initial diagnosis, six months after initial diagnosis, one year after initial diagnosis, etc.

Presence of the labeled antibody or fusion protein can be detected in the subject using methods known in the art for in vivo scanning. These methods depend upon the type of label used. Skilled artisans will be able to determine the appropriate method for detecting a particular label. See, Section 5.4.2, supra, for examples of labels. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the antibody or fusion protein is labeled with a radioisotope and is detected in the patient using a radiation responsive surgical instrument (Thurston et al., U.S. Pat. No. 5,441,050). In another embodiment, the antibody or fusion protein is labeled with a fluorescent compound and is detected in the patient using a fluorescence responsive scanning instrument. In another embodiment, the antibody or fusion protein is labeled with a positron emitting metal and is detected in the patient using positron emission-tomography. In yet another embodiment, the antibody or fusion protein is labeled with a paramagnetic label and is detected in a patient using magnetic resonance imaging (MRI).

5.8. Compositions Comprising Delivery Constructs

The delivery constructs of the invention can be formulated as compositions. The compositions are generally formulated appropriately for the immediate use intended for the delivery construct. For example, if the delivery construct is not to be administered immediately, the delivery construct can be formulated in a composition suitable for storage. One such composition is a lyophilized preparation of the delivery construct together with a suitable stabilizer. Alternatively, the delivery construct composition can be formulated for storage in a solution with one or more suitable stabilizers. Any such stabilizer known to one of skill in the art without limitation can be used. For example, stabilizers suitable for lyophilized preparations include, but are not limited to, sugars, salts, surfactants, proteins, chaotropic agents, lipids, and amino acids. Stabilizers suitable for liquid preparations include, but are not limited to, sugars, salts, surfactants, proteins, chaotropic agents, lipids, and amino acids. Specific stabilizers than can be used in the compositions include, but are not limited to, trehalose, serum albumin, phosphatidylcholine, lecithin, and arginine. Other compounds, compositions, and methods for stabilizing a lyophilized or liquid preparation of the delivery constructs may be found, for example, in U.S. Pat. Nos. 6,573,237, 6,525,102, 6,391,296, 6,255,284, 6,133,229, 6,007,791, 5,997,856, and 5,917,021.

Further, the delivery construct compositions of the invention can be formulated for administration to a subject. Such vaccine compositions generally comprise one or more delivery constructs of the invention and a pharmaceutically acceptable excipient, diluent, carrier, or vehicle. Any such pharmaceutically acceptable excipient, diluent, carrier, or vehicle known to one of skill in the art without limitation can be used. Examples of a suitable excipient, diluent, carrier, or vehicle can be found in *Remington's Pharmaceutical Sciences, 21st Ed.* 2005, Mack Publishing Co., Easton.

In certain embodiments, the delivery construct compositions are formulated for oral administration. In such embodiments, the compositions are formulated to protect the delivery construct from acid and/or enzymatic degradation in the stomach. Upon passage to the neutral to alkaline environment of the duodenum, the delivery construct then contacts a mucous membrane and is transported across the polarized epithelial membrane. The delivery constructs may be formulated in such compositions by any method known by one of skill in the art, without limitation.

In certain embodiments, the oral formulation comprises a delivery construct and one or more compounds that can protect the delivery construct while it is in the stomach. For example, the protective compound should be able to prevent acid and/or enzymatic hydrolysis of the delivery construct. In certain embodiments, the oral formulation comprises a delivery construct and one or more compounds that can facilitate transit of the construct from the stomach to the small intestine. In certain embodiments, the one or more compounds that can protect the delivery construct from degradation in the stomach can also facilitate transit of the construct from the stomach to the small intestine. Preferably, the oral formulation comprises one or more compounds that can protect the delivery construct from degradation in the stomach and facilitate transit of the construct from the stomach to the small intestine. For example, inclusion of sodium bicarbonate can be useful in facilitating the rapid movement of intra-gastric delivered materials from the stomach to the duodenum as described in Mrsny et al., 1999, Vaccine 17:1425-1433.

Other methods for formulating compositions so that the delivery constructs can pass through the stomach and contact polarized epithelial membranes in the small intestine include, but are not limited to, enteric-coating technologies as described in DeYoung, 1989, *Int J Pancreatol.* 5 Suppl:31-6, and the methods provided in U.S. Pat. Nos. 6,613,332, 6,174,529, 6,086,918, 5,922,680, and 5,807,832.

The carrier constructs and antibodies or fusion proteins of the invention can also be formulated as compositions. Appropriate formulations for these compositions include those described above for the delivery construct.

5.8.1. Kits Comprising Compositions

In yet another aspect, the invention provides a kit that comprises a composition of the invention. In certain embodiments, the kit further comprises instructions that direct administration of the composition to a mucous membrane of the subject to whom the composition is administered. In certain embodiments, the kit further comprises instructions that direct oral administration of the composition to the subject to whom the composition is administered.

In certain embodiments, the kit comprises a composition of the invention in more or more containers. In certain embodiments, the composition can be in a unit dosage form, e.g., a tablet, lozenge, capsule, etc. In certain embodiments, the composition can be provided in or with a device for administering the composition, such as, for example, a device configured to administer a single-unit dose of the composition, e.g., an inhaler.

5.9. Methods of Producing Delivery Constructs

The delivery constructs of the invention may be, for example, produced by incubating a carrier construct (preferably, a purified carrier construct) and an antibody of interest or a fusion protein comprising a bioactive molecule and an antibody fragment (preferably, a purified antibody or purified fusion protein) together under conditions permissible for non-covalent binding of the antibody or antibody fragment to the antibody-binding domain of the carrier construct. Optionally, the delivery constructs formed by such an incubation may be separated from unbound carrier construct and/or unbound antibody or unbound fusion protein using techniques known to one of skill in the art. For example, chromatography (e.g., affinity chromatography and ion chromatography), electrically-based methods (e.g., electrophoresis) and microwave can be used to separate the delivery construct from unbound carrier construct and/or unbound antibody or unbound fusion protein. Accordingly, in a specific embodiment, the delivery constructs are purified.

The delivery constructs of the invention may also be produced by co-expressing a carrier construct and an antibody of interest or a fusion protein comprising a bioactive molecule and an antibody or antibody fragment in cells engineered to comprise a first polynucleotide comprising a first nucleotide sequence encoding the carrier construct and a second polynucleotide comprising a second nucleotide sequence encoding the antibody or the fusion protein. Further, the delivery constructs of the invention may be produced by co-administering to a subject a first composition and a second composition, wherein the first composition comprising a carrier construct and the second composition comprises an antibody or a fusion protein comprising a bioactive molecule and an antibody or antibody fragment.

In a preferred embodiment, the delivery constructs of the invention are not produced by happenstance in a subject. In other words, the invention does not encompass delivery constructs inadvertently produced in a subject as a result of an antibody-binding domain of a carrier construct administered to the subject non-covalently binding to an antibody or an antibody fragment of a fusion protein present in the subject. In a preferred embodiment, the delivery constructs of the invention are purified.

In accordance with the invention, the delivery constructs are formed prior to administration to a subject. Alternatively, the delivery constructs are formed following co-administration of a carrier construct and an antibody or a fusion protein comprising a bioactive molecule and an antibody fragment. In accordance with this method, the carrier construct and the antibody or the fusion protein are administered simultaneously or within 1 minute, 2 minutes, 5 minutes, 10 minutes, 15 minutes, 30 minutes, 60 minutes, 2 hours 4 hours, 6 hours or within a day of each other with the intention of producing a delivery construct.

5.10. Recombinant Expression of Carrier Constructs

The carrier constructs of the invention are preferably produced recombinantly, as described below. However, the carrier constructs may also be produced by chemical synthesis using methods known to those of skill in the art.

5.10.1. Polynucleotides Encoding Carrier Constructs

In another aspect, the invention provides polynucleotides comprising a nucleotide sequence encoding the carrier constructs. These polynucleotides are useful, for example, for making the carrier constructs. In yet another aspect, the invention provides an expression system that comprises a recombinant polynucleotide sequence encoding a receptor-binding domain, a transcytosis domain, and a polylinker insertion site for a polynucleotide sequence encoding an antibody-binding domain to which an antibody or antibody fragment non-covalently binds. The polylinker insertion site can be anywhere in the polynucleotide sequence so long as the polylinker insertion does not disrupt the receptor-binding domain or the transcytosis domain. In some embodiments, the polylinker insertion site is oriented near a polynucleotide sequence that encodes a cleavable linker so that cleavage at the cleavable linker separates an antibody-binding domain encoded by a nucleic acid inserted into the polylinker insertion site from the remainder of the encoded carrier construct. Thus, in embodiments where the polylinker insertion site is at an end of the encoded construct, the polynucleotide comprises one nucleotide sequence encoding a cleavable linker between the polylinker insertion site and the remainder of the polynucleotide. In embodiments where the polylinker insertion site is not at the end of the encoded construct, the polylinker insertion site can be flanked by nucleotide sequences that each encode a cleavable linker.

In certain embodiments, the recombinant polynucleotides are based on polynucleotides encoding PE, or portions or derivatives thereof. In other embodiments, the recombinant polynucleotides are based on polynucleotides that hybridize to a polynucleotide that encodes PE under stringent hybridization conditions. A nucleotide sequence encoding PE is presented as SEQ ID NO.:3. This sequence can be used to prepare PCR primers for isolating a nucleic acid that encodes any portion of this sequence that is desired. For example, PCR can be used to isolate a nucleic acid that encodes one or more of the functional domains of PE. A nucleic acid so isolated can then be joined to nucleic acids encoding other functional domains of the carrier constructs using standard recombinant techniques.

Other in vitro methods that can be used to prepare a polynucleotide encoding PE, PE domains, or any other functional domain useful in the carrier constructs of the invention include, but are not limited to, reverse transcription, the polymerase chain reaction (PCR), the ligase chain reaction (LCR), the transcription-based amplification system (TAS), the self-sustained sequence replication system (3SR) and the QP replicase amplification system (QB). Any such technique known by one of skill in the art to be useful in construction of recombinant nucleic acids can be used. For example, a polynucleotide encoding the protein or a portion thereof can be isolated by polymerase chain reaction of cDNA using primers based on the DNA sequence of PE or a nucleotide encoding a receptor-binding domain.

Guidance for using these cloning and in vitro amplification methodologies are described in, for example, U.S. Pat. No. 4,683,195; Mullis et al., 1987, *Cold Spring Harbor Symp. Quant. Biol.* 51:263; and Erlich, ed., 1989, PCR Technology, Stockton Press, NY. Polynucleotides encoding a delivery construct or a portion thereof also can be isolated by screening genomic or cDNA libraries with probes selected from the sequences of the desired polynucleotide under stringent, moderately stringent, or highly stringent hybridization conditions.

Construction of nucleic acids encoding the carrier constructs of the invention can be facilitated by introducing an insertion site for a nucleic acid encoding the antibody-binding domain into the construct. In certain embodiments, an insertion site for the antibody-binding domain can be introduced between the nucleotides encoding the cysteine residues of domain Ib. In other embodiments, the insertion site can be introduced anywhere in the nucleic acid encoding the construct so long as the insertion does not disrupt the functional domains encoded thereby. In certain embodiments, the insertion site can be in the ER retention domain.

In more specific embodiments, a nucleotide sequence encoding a portion of the Ib domain between the cysteine-encoding residues can be removed and replaced with a nucleotide sequence that includes a cloning site cleaved by a restriction enzyme. For example, the cloning site can be recognized and cleaved by PstI. In such examples, a polynucleotide encoding an antibody-binding domain that is flanked by PstI sequences can be inserted into the vector.

Further, the polynucleotides can also encode a secretory sequence at the amino terminus of the encoded carrier construct. Such constructs are useful for producing the carrier constructs in mammalian cells as they simplify isolation of the construct.

Furthermore, the polynucleotides of the invention also encompass derivative versions of polynucleotides encoding a carrier construct. Such derivatives can be made by any method known by one of skill in the art without limitation. For example, derivatives can be made by site-specific mutagenesis, including substitution, insertion, or deletion of one, two, three, five, ten or more nucleotides, of polynucleotides encoding the delivery construct. Alternatively, derivatives can be made by random mutagenesis. One method for randomly mutagenizing a nucleic acid comprises amplifying the nucleic acid in a PCR reaction in the presence of 0.1 mM $MnCl_2$ and unbalanced nucleotide concentrations. These conditions increase the misincorporation rate of the polymerase used in the PCR reaction and result in random mutagenesis of the amplified nucleic acid.

Several site-specific mutations and deletions in chimeric molecules derived from PE have been made and characterized. For example, deletion of nucleotides encoding amino acids 1-252 of PE yields a construct referred to as "PE40." Deleting nucleotides encoding amino acids 1-279 of PE yields a construct referred to as "PE37." See U.S. Pat. No. 5,602,095. In both of these constructs, the receptor-binding domain of PE, i.e., domain Ia, has been deleted. Nucleic acids encoding a receptor-binding domain can be ligated to these constructs to produce delivery constructs that are targeted to the cell surface receptor recognized by the receptor-binding domain. Of course, these recombinant polynucleotides are particularly useful for expressing delivery constructs that have a receptor-binding domain that is not domain Ia of PE. The recombinant polynucleotides can optionally encode an amino-terminal methionine to assist in expression of the construct. In certain embodiments, the receptor-binding domain can be ligated to the 5' end of the polynucleotide encoding the transcytosis domain.

Other nucleic acids encoding mutant forms of PE that can be used as a source of nucleic acids for constructing the carrier constructs of the invention include, but are not limited to, PEΔE553 and those described in U.S. Pat. Nos. 5,602,095; 5,512,658 and 5,458,878, and in Vasil et al., 1986, *Infect. Immunol.* 52:538-48.

Accordingly, in certain embodiments, the invention provides a polynucleotide that encodes a carrier construct. The carrier construct comprises a receptor-binding domain, a transcytosis domain, an antibody-binding domain to which an antibody or antibody fragment binds. Optionally, the carrier construct further comprises a cleavable linker. Cleavage at the cleavable linker can separate the antibody-binding domain from the remainder of the construct. The cleavable linker can be cleaved by an enzyme that is present at a basal-lateral membrane of a polarized epithelial cell of the subject or in the plasma of the subject.

In certain embodiments, the polynucleotide hybridizes under stringent hybridization conditions to any polynucleotide of this invention. In further embodiments, the polynucleotide hybridizes under stringent conditions to a nucleic acid that encodes any carrier construct of the invention.

In certain embodiments, the polynucleotide encodes a carrier construct that further comprises a second cleavable linker. In certain embodiments, the first and/or second cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10). In certain embodiments, the first and/or second cleavable linker encoded by the polynucleotide is cleavable by an enzyme that is selected from the group consisting of Cathepsin GI, Chymotrypsin I, Elastase I, Subtilisin AI, Subtilisin AII, Thrombin I, and Urokinase I.

In certain embodiments, the receptor-binding domain encoded by the polynucleotide is selected from the group consisting of receptor-binding domains from *Pseudomonas* exotoxin A, cholera toxin, diptheria toxin, shiga toxin, or shiga-like toxin; monoclonal antibodies; polyclonal antibodies; single-chain antibodies; TGF α; EGF; IGF-I; IGF-II; IGF-III; IL-1; IL-2; IL-3; IL-6; MIP-1a; MIP-1b; MCAF; and IL-8. In certain embodiments, the receptor-binding domain encoded by the polynucleotide binds to a cell-surface receptor that is selected from the group consisting of α2-macroglobulin receptor, EGFR, IGFR, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor. In further embodiments, the receptor-binding domain encoded by the polynucleotide is Domain Ia of *Pseudomonas* exotoxin A. In yet further embodiments, the receptor-binding domain encoded by the polynucleotide has an amino acid sequence that is SEQ ID NO.:1.

In certain embodiments, the transcytosis domain encoded by the polynucleotide is selected from the group consisting of transcytosis domains from *Pseudomonas* exotoxin A, diptheria toxin, pertussis toxin, cholera toxin, heat-labile *E. coli* enterotoxin, shiga toxin, and shiga-like toxin. In further embodiments, the transcytosis domain is *Pseudomonas* exotoxin A transcytosis domain. In still further embodiments, the *Pseudomonas* exotoxin A transcytosis domain has an amino acid sequence that is SEQ ID NO.:2.

In other embodiments, the invention provides a polynucleotide that encodes a carrier construct that comprises a nucleic acid sequence encoding a receptor-binding domain, a nucleic acid sequence encoding a transcytosis domain, a nucleic acid sequence comprising a polylinker insertion site, and optionally a nucleic acid sequence encoding a cleavable linker. The polylinker insertion site can be oriented relative to the nucleic acid sequence encoding a cleavable linker to allow to cleavage of the cleavable linker to separate a macromolecule that is encoded by a nucleic acid inserted into the polylinker insertion site from the remainder of said delivery construct. The cleavable linker can be cleavable by an enzyme that is present at a basal-lateral membrane of a polarized epithelial cell of said subject or in the plasma of said subject.

5.10.2. Expression Vectors for Expressing Carrier Constructs

In still another aspect, the invention provides expression vectors for expressing the carrier constructs. Generally, expression vectors are recombinant polynucleotide molecules comprising expression control sequences operatively linked to a nucleotide sequence encoding a polypeptide. Expression vectors can readily be adapted for function in prokaryotes or eukaryotes by inclusion of appropriate promoters, replication sequences, selectable markers, etc. to result in stable transcription and translation of mRNA. Techniques for construction of expression vectors and expression of genes in cells comprising the expression vectors are well known in the art. See, e.g., Sambrook et al., 2001, *Molecular Cloning—A Laboratory Manual,* 3$^{rd}$ edition, Cold Spring Harbor Laboratory, Cold Spring Harbor, N.Y., and Ausubel et al., eds., Current Edition, *Current Protocols in Molecular Biology*, Greene Publishing Associates and Wiley Interscience, NY.

Useful promoters for use in expression vectors include, but are not limited to, a metallothionein promoter, a constitutive adenovirus major late promoter, a dexamethasone-inducible MMTV promoter, a SV40 promoter, a MRP pol III promoter, a constitutive MPSV promoter, a tetracycline-inducible CMV promoter (such as the human immediate-early CMV promoter), and a constitutive CMV promoter. See Section 5.8 and 5.9, infra, for examples of other types of promoters.

The expression vectors should contain expression and replication signals compatible with the cell in which the carrier constructs are expressed. Expression vectors useful for expressing carrier constructs include viral vectors such as retroviruses, adenoviruses and adenoassociated viruses, plasmid vectors, cosmids, and the like. Viral and plasmid vectors are preferred for transfecting the expression vectors into mammalian cells. For example, the expression vector pcDNA1 (Invitrogen, San Diego, Calif.), in which the expression control sequence comprises the CMV promoter, provides good rates of transfection and expression into such cells. See Sections 5.8 and 5.9, infra, for examples of other types of expression vectors.

The expression vectors can be introduced into the cell for expression of the carrier constructs by any method known to one of skill in the art without limitation. Such methods include, but are not limited to, e.g., direct uptake of the molecule by a cell from solution; facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. See Sections 5.8 and 5.9, infra, for examples of other methods of introducing expression vectors into cells and for methods of producing stable cells containing expression vectors.

The expression vectors can also contain a purification moiety that simplifies isolation of the carrier construct. For example, a polyhistidine moiety of, e.g., six histidine residues, can be incorporated at the amino terminal end of the protein. The polyhistidine moiety allows convenient isolation of the protein in a single step by nickel-chelate chromatography. In certain embodiments, the purification moiety can be cleaved from the remainder of the carrier construct following purification. In other embodiments, the moiety does not interfere with the function of the functional domains of the carrier construct and thus need not be cleaved.

5.10.3. Cell for Expressing a Carrier Construct

In yet another aspect, the invention provides a cell comprising an expression vector for expression of the carrier constructs, or portions thereof. The cell is preferably selected for its ability to express high concentrations of the carrier construct to facilitate purification of the protein. In certain embodiments, the cell is a prokaryotic cell, for example, *E. coli*. As described in the examples, the carrier constructs are properly folded and comprise the appropriate disulfide linkages when expressed in *E. coli*.

In other embodiments, the cell is a eukaryotic cell. Useful eukaryotic cells include yeast and mammalian cells. Any mammalian cell known by one of skill in the art to be useful for expressing a recombinant polypeptide, without limitation, can be used to express the delivery constructs. For example, Chinese hamster ovary (CHO) cells can be used to express the carrier constructs. See, e.g., Sections 5.8 and 5.9, infra, for additional examples of cell types that may be used to express a carrier construct.

5.11. Recombinant Expression of Antibodies

The antibodies of the invention can be produced by any method known in the art for the synthesis of antibodies, in particular, by chemical synthesis or preferably, by recombinant expression techniques.

The nucleotide sequence encoding an antibody may be obtained from any information available to those of skill in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties), to generate antibodies having a different amino acid sequence by, for example, introducing amino acid substitutions, deletions, and/or insertions into the epitope-binding domain regions of the antibodies and/or into the hinge-Fc regions of the antibodies.

Recombinant expression of an antibody requires construction of an expression vector containing a nucleotide sequence that encodes the antibody. Once a nucleotide sequence encoding an antibody molecule or a heavy or light chain of an antibody, or portion thereof (preferably, but not necessarily, containing the heavy or light chain variable region) has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression.

The expression vector is transferred to a host cell by conventional techniques and the transfected cells are then cultured by conventional techniques to produce an antibody. A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces* and *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; and tobacco mosaic virus, TMV) or transformed with recombinant plasmid expression vectors (e.g., Ti plasmid) containing antibody coding sequences; and mammalian cell systems (e.g., COS, CHO, BHK, 293, 3T3 and NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus are an effective expression system for antibodies (Foecking et al., 1986, *Gene*, 45:101; Cockett et al., 1990, *Bio/Technology*, 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO*, 12:1791), in which the antibody coding sequence may be ligated individually into the vector in frame with the lacZ coding region so that a fusion protein is produced; and pIN vectors (Inouye & Inouye, 1985, *Nucleic Acids Res.*, 13:3101-3109; Van Heeke & Schuster, 1989, *J. Biol. Chem.*, 24:5503-5509).

In an insect system, *Autographa californica* nuclear polyhedrosis virus (AcNPV) can be used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express an antibody molecule of the invention. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA*, 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bitter et al., 1987, *Methods Enzymol.*, 153:516-544).

In addition, a host cell strain may be chosen which modulates the expression of the antibody sequences, or modifies and processes the antibody in the specific fashion desired. Such modifications (e.g., glycosylation) and processing (e.g., cleavage) of protein products may be important for the function of the antibody. Different host cells have characteristic and specific mechanisms for the post-translational processing and modification of proteins and gene products. Appropriate cell lines or host systems can be chosen to ensure the correct modification and processing of the antibody expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, and in particular, myeloma cells such as NSO cells, and related cell lines, see, for example, Morrison et al., U.S. Pat. No. 5,807,715, which is hereby incorporated by reference in its entirety.

For long-term, high-yield production of recombinant antibodies, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, *Cell*, 11:223), hypoxanthineguanine phosphoribosyltransferase (Szybalska & Szybalski, 1992, *Proc. Natl. Acad. Sci. USA*, 48:202), and adenine phosphoribosyltransferase (Lowy et al., 1980, *Cell*, 22:8-17) genes can be employed in tk⁻, hgprt⁻ or aprt⁻ cells, respectively. Also, antimetabolite resistance can be used as the basis of selection for the following genes: dhfr, which confers resistance to methotrexate (Wigler et al., 1980, *Natl. Acad. Sci. USA*, 77:357; O'Hare et al., 1981, *Proc. Natl. Acad. Sci. USA*, 78:1527); gpt, which confers resistance to mycophenolic acid (Mulligan & Berg, 1981, *Proc. Natl. Acad. Sci. USA*, 78:2072); neo, which confers resistance to the aminoglycoside G-418 (Wu and Wu, 1991, *Biotherapy*, 3:87-95; Tolstoshev, 1993, *Ann. Rev. Pharmacol. Toxicol.*, 32:573-596; Mulligan, 1993, *Science*, 260:926-932; Morgan and Anderson, 1993, *Ann. Rev. Biochem.*, 62: 191-217; May, 1993, *TIB TECH*, 11(5):155-215); and hygro, which confers resistance to hygromycin (Santerre et al., 1984, Gene, 30:147). Methods commonly known in the art of recombinant DNA technology may be routinely applied to select the desired recombinant clone, and such methods are described, for example, in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; in Chapters 12 and 13, Dracopoli et al. (eds), 1994, *Current Protocols in Human Genetics*, John Wiley & Sons, NY; and Colberre-Garapin et al., 1981, *J. Mol. Biol.*, 150: 1, which are incorporated by reference herein in their entireties.

The expression levels of an antibody molecule can be increased by vector amplification (for a review, see Bebbington and Hentschel, 1987, *The use of vectors based ongene amplification for the expression of cloned genes in mammalian cells in DNA cloning*, Vol. 3. Academic Press, New York). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol., Cell. Biol.*, 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature*, 322:52; Kohler, 1980, *Proc. Natl. Acad. Sci. USA*, 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

5.12. Recombinant Expression of Fusion Proteins

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the constant domain or fragment thereof.

Methods for fusing or conjugating polypeptides to the constant regions of antibodies are known in the art. See, e.g., U.S. Pat. Nos. 5,336,603, 5,622,929, 5,359,046, 5,349,053, 5,447, 851, 5,723,125, 5,783,181, 5,908,626, 5,844,095, and 5,112, 946; EP 307,434; EP 367,166; EP 394,827; PCT publications WO 91/06570, WO 96/04388, WO 96/22024, WO 97/34631, and WO 99/04813; Ashkenazi et al., 1991, *Proc. Natl. Acad. Sci. USA*, 88: 10535-10539; Traunecker et al., 1988, *Nature*, 331:84-86; Zheng et al., 1995, *J. Immunol.*, 154:5590-5600; and Vil et al., 1992, *Proc. Natl. Acad. Sci. USA*, 89:11337-11341, which are incorporated herein by reference in their entireties.

The nucleotide sequence encoding a bioactive molecule may be obtained from any information available to those of skill in the art (e.g., from Genbank, the literature, or by routine cloning), and the nucleotide sequence encoding an antibody fragment (e.g., a constant domain of an antibody or a fragment thereof) may be determined by sequence analysis of mutants produced using techniques described herein, or may be obtained from Genbank or the literature. The nucleotide sequence coding for a fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a fusion protein may be controlled by any promoter or enhancer element known in the art. Promoters which may be used to control the expression of the gene encoding fusion protein include, but are not limited to, the SV40 early promoter region (Bemoist and Chambon, 1981, *Nature*, 290:304-310), the promoter contained in the 3' long terminal repeat of Rous sarcoma virus (Yamamoto, et al., 1980, *Cell*, 22:787-797), the herpes thymidine kinase promoter (Wagner et al., 1981, *Proc. Natl. Acad. Sci. U.S.A.*, 78:1441-1445), the regulatory sequences of the metallothionein gene (Brinster et al., 1982, *Nature*, 296:39-42), the tetracycline (Tet) promoter (Gossen et al., 1995, *Proc. Nat. Acad. Sci. USA*, 89:5547-5551); prokaryotic expression vectors such as the beta-lactamase promoter (Villa-Kamaroff, et al., 1978, *Proc. Natl. Acad. Sci. U.S.A.*, 75:3727-3731), or the tac promoter (DeBoer, et al., 1983, *Proc. Natl. Acad. Sci. U.S.A.*, 80:21-25; see also "Useful proteins from recombinant bacteria" in *Scientific American*, 242:74-94, 1980); plant expression vectors comprising the nopaline synthetase promoter region (Herrera-Estrella et al., 1983, *Nature*, 303:209-213) or the cauliflower mosaic virus 35S RNA promoter (Gardner, et al., 1981, *Nucl. Acids Res.*, 9:2871), and the promoter of the photosynthetic enzyme ribulose biphosphate carboxylase (Herrera-Estrella et al., 1984, *Nature,* 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, *Cell* 38:639-646; Omitz et al., 1986, *Cold Spring Harbor Symp. Quant. Biol.,* 50:399-409, MacDonald, 1987, *Hepatology* 7:425-515); insulin gene control region which is active in pancreatic beta cells (Hanahan, 1985, *Nature* 315:115-122), immunoglobulin gene control region which is active in lymphoid cells (Grosschedl et al., 1984, *Cell,* 38:647-658; Adames et al., 1985, *Nature* 318:533-538; Alexander et al., 1987, *Mol. Cell. Biol.,* 7:1436-1444), mouse mammary tumor virus control region which is active in testicular, breast, lymphoid and mast cells (Leder et al., 1986, *Cell,* 45:485-495), albumin gene control region which is active in liver (Pinkert et al., 1987, *Genes and Devel.,* 1:268-276), alpha-fetoprotein gene control region which is active in liver (Krumlauf et al., 1985, *Mol. Cell. Biol.,* 5:1639-1648; Hammer et al., 1987, *Science,* 235:53-58; alpha1-antitrypsin gene control region which is active in the liver (Kelsey et al., 1987, *Genes and Devel.,* 1:161-171), beta-globin gene control region which is active in myeloid cells (Mogram et al., 1985, *Nature,* 315: 338-340; Kollias et al., 1986, *Cell,* 46:89-94; myelin basic protein gene control region which is active in oligodendrocyte cells in the brain (Readhead et al., 1987, *Cell,* 48:703-712); myosin light chain-2 gene control region which is active in skeletal muscle (Sani, 1985, *Nature,* 314:283-286); neuronal-specific enolase (NSE) which is active in neuronal cells (Morelli et al., 1999, *Gen. Virol.,* 80:571-83); brain-derived neurotrophic factor (BDNF) gene control region which is active in neuronal cells (Tabuchi et al., 1998, *Biochem. Biophys. Res. Commun.,* 253:818-823); glial fibrillary acidic protein (GFAP) promoter which is active in astrocytes (Gomes et al., 1999, *Braz. J. Med. Biol. Res.,* 32(5):619-631; Morelli et al., 1999, *Gen. Virol.,* 80:571-83) and gonadotropic releasing hormone gene control region which is active in the hypothalamus (Mason et al., 1986, *Science,* 234:1372-1378).

In a specific embodiment, the expression of a fusion protein is regulated by a constitutive promoter. In another embodiment, the expression of a fusion protein is regulated by an inducible promoter. In accordance with these embodiments, the promoter may be a tissue-specific promoter.

In a specific embodiment, a vector is used that comprises a promoter operably linked to a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA,* 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, *Methods Enzymol.,* 153:516-544).

Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein) expressed by the recombinant. Such assays can be based, for example, on the physical or functional properties of the fusion protein in in vitro assay systems, e.g., binding with antibioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, neuronal cell lines such as, for example, SK-N-AS, SK-N-FI, SK-N-DZ human neuroblastomas (Sugimoto et al., *J. Natl. Cancer Inst.,* 73: 51-57, 1984), SK-N-SH human neuroblastoma (*Biochim. Biophys. Acta,* 704: 450-460, 1982), Daoy human cerebellar medulloblastoma (He et al., *Cancer Res.,* 52: 1144-1148, 1992) DBTRG-05MG glioblastoma cells (Kruse et al., 1992, *In Vitro Cell. Dev. Biol.,* 28A: 609-614, 1992), IMR-32 human neuroblastoma (*Cancer Res.,* 30: 2110-2118, 1970), 1321N1 human astrocytoma (*Proc. Natl Acad. Sci. USA,* 74: 4816, 1997), MOG-G-CCM human astrocytoma (Br. J. Cancer, 49: 269, 1984), U87MG human glioblastoma-astrocytoma (*Acta Pathol. Microbiol. Scand.,* 74: 465-486, 1968), A172 human glioblastoma (Olopade et al., *Cancer Res.,* 52: 2523-2529, 1992), C6 rat glioma cells (Benda et al., Science, 161: 370-371, 1968), Neuro-2a mouse neuroblastoma (*Proc. Natl. Acad. Sci. USA*, 65: 129-136, 1970), NB41A3 mouse neuroblastoma (*Proc. Natl. Acad. Sci. USA*, 48: 1184-1190, 1962), SCP sheep choroid plexus (Bolin et al., *J. Virol. Methods*, 48: 211-221, 1994), G355-5, PG-4 Cat normal astrocyte (Haapala et al., *J. Virol.*, 53: 827-833, 1985), Mpf ferret brain (Trowbridge et al., *In Vitro*, 18: 952-960, 1982), and normal cell lines such as, for example, CTX TNA2 rat normal cortex brain (Radany et al., *Proc. Natl. Acad. Sci. USA*, 89: 6467-6471, 1992) such as, for example, CRL7030 and Hs578Bst. Furthermore, different vector/host expression systems may effect processing reactions to different degrees.

For long-term, high-yield production of recombinant proteins, stable expression is preferred. For example, cell lines which stably express the fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1997, *Cell*, 11:223), hypoxanthine-guanine phosphoribosyltransferase (Szybalska & Szybalski, 1962, *Proc. Natl. Acad. Sci. USA*, 48:2026), and adenine phosphoribosyltransferase (Lowy, et al., 1980, *Cell*, 22:817, 1980) genes can be employed in tk-, hgprt- or aprt-cells, respectively. Also, anti-metabolite resistance can be used as the basis of selection for dhfr, which confers resistance to methotrexate (Wigler, et al., 1980, *Natl. Acad. Sci. USA*, 77:3567; O'Hare, et al., 1981, *Proc. Natl. Acad. Sci. USA*, 78:1527); gpt, which confers resistance to mycophenolic acid (Mulligan & Berg, 1981, *Proc. Natl. Acad. Sci. USA*, 78:2072); neo, which confers resistance to the aminoglycoside G-418 (Colberre-Garapin, et al., 1981, *J. Mol. Biol.*, 150:1); and hygro, which confers resistance to hygromycin (Santerre, et al., 1984, *Gene*, 30:147) genes.

Once a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.13. Biological Activity of Delivery Constructs

Having selected the domains of the carrier construct, the function of these domains, and of the delivery constructs as a whole, can be routinely tested to ensure that the constructs can deliver antibody or fusion protein across mucous membranes of a subject free from the remainder of the construct. For example, the carrier constructs and/or delivery constructs can be tested for cell recognition, transcytosis and cleavage using routine assays. The entire carrier construct can be tested, or, the function of various domains can be tested by substituting them for native domains of the wild-type toxin.

5.13.1.1. Receptor-binding/Cell Recognition

Receptor-binding domain function can be tested by monitoring the delivery construct's or carrier construct's ability to bind to the target receptor. Such testing can be accomplished using cell-based assays, with the target receptor present on a cell surface, or in cell-free assays. For example, delivery construct or carrier construct binding to a target can be assessed with affinity chromatography. The construct can be attached to a matrix in an affinity column, and binding of the receptor to the matrix detected, or vice versa. Alternatively, if antibodies have been identified that bind to either the receptor-binding domain or its cognate receptor, the antibodies can be used, for example, to detect the receptor-binding domain in the delivery construct or carrier construct by immunoassay, or in a competition assay for the cognate receptor. An exemplary cell-based assay that detects delivery construct or carrier construct binding to receptors on cells comprises labeling the construct and detecting its binding to cells by, e.g., fluorescent cell sorting, autoradiography, etc.

5.13.1.2. Transcytosis

The function of the transcytosis domain can be tested as a function of the delivery construct's or carrier construct's ability to pass through an epithelial membrane. Because transcytosis first requires binding to the cell, these assays can also be used to assess the function of the cell recognition domain.

The delivery construct's or carrier construct's transcytosis activity can be tested by any method known by one of skill in the art, without limitation. In certain embodiments, transcytosis activity can be tested by assessing the ability of a delivery construct or carrier construct to enter a non-polarized cell to which it binds. Without intending to be bound to any particular theory or mechanism of action, it is believed that the same property that allows a transcytosis domain to pass through a polarized epithelial cell also allows molecules bearing the transcytosis domain to enter non-polarized cells. Thus, the delivery construct's or carrier construct's ability to enter the cell can be assessed, for example, by detecting the physical presence of the construct in the interior of the cell. For example, the delivery construct or the carrier construct can be labeled with, for example, a fluorescent marker, and the delivery construct or carrier construct exposed to the cell. Then, the cells can be washed, removing any delivery construct or carrier construct that has not entered the cell, and the amount of label remaining determined. Detecting the label in this fraction indicates that the delivery construct or the carrier construct has entered the cell.

In other embodiments, the delivery construct's or carrier construct's transcytosis ability can be tested by assessing the delivery construct's or carrier construct's ability to pass through a polarized epithelial cell. For example, the delivery construct or carrier construct can be labeled with, for example, a fluorescent marker and contacted to the apical membranes of a layer of epithelial cells. Fluorescence detected on the basal-lateral side of the membrane formed by the epithelial cells indicates that the transcytosis domain is functioning properly.

5.13.1.3. Cleavable Linker Cleavage

The function of the cleavable linker can generally be tested in a cleavage assay. Any suitable cleavage assay known by one of skill in the art, without limitation, can be used to test the cleavable linkers. Both cell-based and cell-free assays can be used to test the ability of an enzyme to cleave the cleavable linkers.

An exemplary cell-free assay for testing cleavage of cleavable linkers comprises preparing extracts of polarized epithelial cells and exposing a labeled delivery construct or a labeled carrier construct bearing a cleavable linker to the fraction of the extract that corresponds to membrane-associated enzymes. In such assays, the label can be attached to either the antibody-binding domain or to the remainder of the carrier construct. Among these enzymes are cleavage enzymes found near the basal-lateral membrane of a polarized epithelial cell, as described above. Cleavage can be detected, for example, by binding the delivery construct with, for example, an antibody and washing off unbound molecules. If label is attached to the macromolecule to be delivered, then little or no label should be observed on the molecule bound to the antibodies. Alternatively, the binding agent used in the assay can be specific for the macromolecule, and the remainder of the construct can be labeled. In either case, cleavage can be assessed.

Cleavage can also be tested using cell-based assays that test cleavage by polarized epithelial cells assembled into membranes. For example, a labeled delivery construct, or portion of a delivery construct comprising the cleavable linker, can be contacted to either the apical or basolateral side of a monolayer of suitable epithelial cells, such as, for example, Coco-2 cells, under conditions that permit cleavage of the linker. Cleavage can be detected by detecting the presence or absence of the label using a reagent that specifically binds the delivery construct, or portion thereof. For example, an antibody specific for the delivery construct can be used to bind a delivery construct comprising a label distal to the cleavable linker in relation to the portion of the delivery construct bound by the antibody. Cleavage can then be assessed by detecting the presence of the label on molecules bound to the antibody. If cleavage has occurred, little or no label should be observed on the molecules bound to the antibody. By performing such experiments, enzymes that preferentially cleave at the basolateral membrane rather than the apical membrane can be identified, and further, the ability of such enzymes to cleave the cleavable linker in a delivery construct can be confirmed.

Further, cleavage can also be tested using a fluorescence reporter assay as described in U.S. Pat. No. 6,759,207. Briefly, in such assays, the fluorescence reporter is contacted to the basolateral side of a monolayer of suitable epithelial cells under conditions that allow the cleaving enzyme to cleave the reporter. Cleavage of the reporter changes the structure of the fluorescence reporter, changing it from a non-fluorescent configuration to a fluorescent configuration. The amount of fluorescence observed indicates the activity of the cleaving enzyme present at the basolateral membrane.

Further, cleavage can also be tested using an intra-molecularly quenched molecular probe, such as those described in U.S. Pat. No. 6,592,847. Such probes generally comprise a fluorescent moiety that emits photons when excited with light of appropriate wavelength and a quencher moiety that absorbs such photons when in close proximity to the fluorescent moiety. Cleavage of the probe separates the quenching moiety from the fluorescent moiety, such that fluorescence can be detected, thereby indicating that cleavage has occurred. Thus, such probes can be used to identify and assess cleavage by particular cleaving enzymes by contacting the basolateral side of a monolayer of suitable epithelial cells with the probe under conditions that allow the cleaving enzyme to cleave the probe. The amount of fluorescence observed indicates the activity of the cleaving enzyme being tested.

5.13.2. Proper Folding of the Carrier Construct

To determine that a carrier construct has properly folded and is able to bind to an antibody or an antibody fragment of a fusion protein, an immunoassay can be performed. For example, an ELISA can be performed. Such an ELISA may comprise: coating a 96 well plate with an antibody or fusion protein of interest, adding the carrier construct to the well and incubating for a period of time, and detecting the binding of the antibody or fusion protein to the carrier construct. To detect the binding, a second detectably labeled antibody that recognizes the carrier construct can be added to the well.

5.13.3. Binding Affinity of Antibody-Binding Domain

The binding affinity of an antibody-binding domain of a carrier construct for an antibody or antibody fragment of a fusion protein can be determined by competitive binding assays. One example of a competitive binding assay is a radioimmunoassay comprising the incubation of labeled antibody or labeled fusion protein (e.g., $^3$H or $^{125}$I) with the carrier construct of interest in the presence of increasing amounts of unlabeled antibody or unlabeled fusion protein, and the detection of the carrier construct bound to the labeled antibody or labeled fusion protein. The affinity of the antibody-binding domain of the carrier construct for the antibody or the antibody fragment of the fusion protein and the binding off-rates can be determined from the saturation data by scatchard analysis. Competition with a second antibody or second fusion protein can also be determined using radioimmunoassays.

In a preferred embodiment, BIAcore kinetic analysis is used to determine the binding on and off rates of antibodies or fusion proteins comprising an antibody fragment to a carrier construct. BIAcore kinetic analysis comprises analyzing the binding and dissociation of an antigen from chips with immobilized antibodies on their surface.

5.13.4. Activity of Delivery Construct

The delivery constructs and compositions of the invention are preferably tested in vitro, and then in vivo for the desired therapeutic or prophylactic activity, prior to use in humans. For example, in vitro assays which can be used to determine whether administration of a specific delivery construct or a composition of the present invention is indicated, include in vitro cell culture assays in which a subject tissue sample is grown in culture, and exposed to or otherwise administered the delivery construct or composition of the present invention, and the effect of such delivery construct or composition of the present invention upon the tissue sample is observed. In various specific embodiments, in vitro assays can be carried out with representative cells of cell types involved in a disorder, to determine if a delivery construct or composition of the present invention has a desired effect upon such cell types.

Delivery constructs or compositions of the present invention for use in preventing, treating, managing or ameliorating a disorder or a symptom thereof can be tested for their toxicity in suitable animal model systems, including but not limited to rats, mice, cows, monkeys, and rabbits. For in vivo testing for the toxicity of a delivery construct or a composition, any animal model system known in the art may be used.

5.13.5. Pharmacokinetic Assays

To assess the pharmacokinetics of an exemplary antibodies or fusion proteins delivered with a delivery construct, ELISA assays can used to measure serum concentrations of the antibody or the fusion protein at defined timepoints following administration. Serum concentration data obtained is used to compare the pharmacokinetics of the antibody or the fusion protein administered with the delivery construct to those observed with conventional methods administration (e.g., subcutaneous injection).

6. EXAMPLES

The following examples merely illustrate the invention, and are not intended to limit the invention in any way.

6.1. ntPE-Protein G Antibody Delivery Construct

This example describes delivery of an exemplary monoclonal antibody with an exemplary delivery construct comprising a Protein G antibody-binding domain.

6.1.1. Construction of ntPE-Protein G Antibody Delivery Construct ntPE-Protein G carrier constructs comprise sequences encoding Domains I and II of ntPE (amino acid residues 26-372 as shown in FIG. 1) and the Fc-binding domain of Protein G (SEQ ID NO: 24). The Fc-binding domain of Protein G is attached to the C-terminus of ntPE. BL21(DE3) pLysS competent cells transfected with ntPE-Protein G expression vector were grown in 2xLB broth containing 50 µg/ml ampicillin at 37° C. The expression of recombinant ntPE Protein G was induced at $OD_{600}$=0.8 with 1 mM isopropyl b-D-thiogalactoside. The cells were harvested 4 hrs after induction and the inclusion bodies was extracted and solubilized with 6 M Guanidine and 65 mM DTT. The protein was renaturized by dialysis and purified by sequential column chromatography using Q sepharose HP and Sephadex 200. Then, a final concentration of 0.4 mg/ml of ntPE Protein G was mixed with 0.8 mg/ml of human IgG (molar ratio: 2:1) in PBS for 2 hrs at room temperature.

6.1.2. Administration of ntPE-Protein G Antibody Delivery Construct to Mice 100 µg of the suspension of protein mixture was administered by oral gavage to BALB/c mice in 250 µl of PBS with 1 mg/ml of BSA as a carrier. Serum samples, prepared from blood collected at the time points identified in FIG. 2, were analyzed for the presence of human IgG by ELISA.

6.1.3. Measurement of Human IgG in Mouse Serum Using Monoclonal Antibodies

Human IgG in mouse serum samples were measured by ELISA. The employed Human IgG ELISA method was developed by Trinity Biosystems and was conducted in accordance with SOP-032. Costar 9018 E.I.A./R.I.A. 96-well plates were coated overnight with about 300 ng/well of mouse anti-human IgG (Abcam, Cat. No. ab7497) in 0.2M $NaHCO_3$—$Na_2CO_3$, pH 9.4. Each 96-well plate was washed four times with PBS containing 0.05% Tween 20-0.01% thimerosal (wash buffer); blocked for 1 h with 200 µl/well of PBS/Tween 20 containing 0.5% BSA-0.01% thimerosal (assay buffer). Purified Human IgG (Antibodies Inc., Cat. No. 43-636) diluted in assay buffer was used as the standard curve. Standard curve was prepared by adding 10 µl of the 1.0 mg/ml Human IgG to 990 µl assay buffer (1:100), mixing well and moving 10 µl to 990 µl assay buffer (1:100). This solution was used as the first point for the standard curve. For each plate, 0.5 ml was moved to 0.5 ml assay buffer, and did a 1:2 serial dilution. The 10 points are of the standard curve were: 100, 50, 25, 12.5, 6.25, 3.125, 1.56, 0.78, 0.39, and 0.195 ng/well. Serum samples were diluted at 1:10 in assay buffer. Each plate was washed again, and standard curve and samples were loaded in 100 µl/well triplicates onto a 96-well plate, and incubated for 3 h to detect Human IgG in serum samples. Each 96-well plate was then washed four times with wash buffer, and added 100 µl/well of mouse anti-human IgG-biotin (Zymed, Cat. No. 05-4240) at 1:1000 dilutions and incubated for 2 h. Each 96-well plate was then washed four times with wash buffer, and added 100 µl/well of horseradish peroxidase (HRP) conjugated ExtrAvidin (Sigma, Cat. No. E-2886) at 1:2000 dilutions and incubated for 1 h. All incubation and coating steps were performed at room temperature on a shaker at 6 RPM. Each 96-well plate was then washed four times with wash buffer, and the HRP substrate, TMB (3,3',5,5'tetramethylbenzidine), used to quantify bound antibody, was measured at 450 nm.

ELISA results are reported as the averages of the triplicate OD (450 mm) value of each sample. See FIG. 2. As shown in FIG. 2, the delivery construct comprising the Protein G antibody-binding domain was able to deliver a human monoclonal antibody to mouse serum, with highest tested serum concentration at 30 minutes following oral administration.

6.2. ntPE-Protein A Antibody Delivery Construct

6.2.1. Construction of ntPE-Protein A Antibody Delivery Construct ntPE-Protein A carrier constructs comprise sequences encoding Domains I and II of ntPE (amino acid residues 26-372 as shown in FIG. 1) and a Protein A antibody-binding fragment (SEQ ID NO:25). The Protein A antibody-binding fragment is attached to the C-terminus of ntPE. BL21 (DE3) pLysS competent cells are transfected with ntPE-Protein A expression vector. The transfected cells are grown in 2xLB broth containing 50 µg/ml ampicillin at 37° C. The expression of recombinant ntPE Protein A is induced at $OD_{600}$=0.8 with 1 mM isopropyl b-D-thiogalactoside. The cells are harvested 4 hrs after induction and the inclusion bodies is extracted and solubilized with 6 M Guanidine and 65 mM DTT. The protein is renaturized by dialysis and purified by sequential column chromatography using Q sepharose HP and Sephadex 200. Then, a final concentration of 0.4 mg/ml of ntPE-Protein A is mixed with 0.8 mg/ml of human IgG (molar ratio: 2:1) in PBS for 2 hrs at room temperature.

6.2.2. Administration of Protein A-Antibody Delivery Construct to Mice

100 µg of the suspension of protein mixture is administered by oral gavage to BALB/c mice in 250 µl of PBS with 1 mg/ml of BSA as a carrier. Serum samples, prepared from blood collected at various time points, are analyzed for the presence of human IgG by ELISA.

6.2.3. Measurement of Human IgG in Mouse Serum Using Monoclonal Antibodies

Human IgG in mouse serum samples are measured by the ELISA described in Section 6.1.3, supra.

6.3. ntPE-FcRn Antibody Delivery Construct

6.3.1. Construction of FcRn-Antibody Delivery Construct ntPE-FcRn carrier construct comprises sequences encoding Domains I and II of ntPE (amino acid residues 26-372 as shown in FIG. 1) and human FcRn (SEQ ID NO:26; Mikulska et al., 2000, *Eur. J. Immunogenet.* 27(4):231-240). The human FcRn is attached to the C-terminus of ntPE. Some of the carrier constructs comprise a cleavable linker between the ntPE sequences and the FcRn sequences. In particular, some of the constructs comprise one of the following cleavable linkers: RQPRGGL (SEQ ID NO.:30), GGLRQPR (SEQ ID NO.:31), RQPREGR (SEQ ID NO.:32), RQPRVGR (SEQ ID NO.:33), and RQPRARR (SEQ ID NO.:34). BL21 (DE3) pLysS competent cells are transfected with ntPE-FcRn expression vector. The transfected cells are grown in 2xLB broth containing 50 µg/ml ampicillin at 37° C. The expression of recombinant ntPE-FcRn is induced at $OD_{600}$=0.8 with 1 mM isopropyl b-D-thiogalactoside. The cells are harvested 4 hrs after induction and the inclusion bodies are extracted and solubilized with 6 M Guanidine and 65 mM DTT. The protein is renaturized by dialysis and purified by sequential column chromatography using Q sepharose HP and Sephadex 200. Alternately, this protein construct was purified from a mammalian cell culture system where the material was secreted as a folded structure. Then, a final concentration of 0.4 mg/ml of ntPE-FcRn is mixed with 0.8 mg/ml of human IgG (molar ratio: 2:1) in PBS for 2 hrs at room temperature. In particular, a final concentration of 0.4 mg/ml of ntPE-FcRn is mixed with 0.8 mg/ml of Avastin (molar ratio: 2:1) or 0.8 mg/ml of Rituxan in PBS for 2 hrs at room temperature.

6.3.2. Administration of ntPE-FcRn-Antibody Delivery Construct to Mice

100 μg of the suspension of protein mixture is administered by oral gavage to BALB/c mice in 250 μl of PBS with 1 mg/ml of BSA as a carrier. Serum samples, prepared from blood collected at various time points, are analyzed for the presence of human IgG by ELISA.

6.3.3. Measurement of Human IgG in Mouse Serum Using Monoclonal Antibodie

Human IgG in mouse serum samples are measured by the ELISA described in Section 6.1.3, supra.

6.4. ntPE-FcγRIII Antibody Delivery Construct 6.4.1. Construction of FcR-Antibody Delivery Construct ntPE-FcγRIII carrier construct comprises sequences encoding Domains I and II of ntPE (amino acid residues 26-372 as shown in FIG. 1) and human FcγRIII (SEQ ID NO:27; Radaev et al., 2001, *J. Biol. Chem.* 276: 16469) or human FcγRIII-beta (SEQ ID NO:28), or an antibody-binding domain of human FcγRIII-beta (SEQ ID NO:29). The human FcγRIII is attached to the C-terminus of ntPE. Some of the carrier constructs comprise a cleavable linker between the ntPE sequences and the FcγRIII sequences. In particular, some of the constructs comprise one of the following cleavable linkers: RQPRGGL (SEQ ID NO.:30), GGLRQPR (SEQ ID NO.:31), RQPREGR (SEQ ID NO.:32), RQPRVGR (SEQ ID NO.:33), and RQPRARR (SEQ ID NO.:34). BL21 (DE3)pLysS competent cells are transfected with ntPE-FcγRIII expression vector. The transfected cells are grown in 2xLB broth containing 50 μg/ml ampicillin at 37° C. The expression of recombinant ntPE-FcγRIII is induced at $OD_{600}$=0.8 with 1 mM isopropyl b-D-thiogalactoside. The cells are harvested 4 hrs after induction and the inclusion bodies are extracted and solubilized with 6 M Guanidine and 65 mM DTT. The protein is renaturized by dialysis and purified by sequential column chromatography using Q sepharose HP and Sephadex 200. Alternately, this protein construct was purified from a mammalian cell culture system where the material was secreted as a folded structure. Then, a final concentration of 0.4 mg/ml of ntPE-FcγRIII is mixed with 0.8 mg/ml of human IgG (molar ratio: 2:1) in PBS for 2 hrs at room temperature. In particular, a final concentration of 0.4 mg/ml of ntPE-FcγRIII is mixed with 0.8 mg/ml of Avastin (molar ratio: 2:1) or 0.8 mg/ml of Rituxan in PBS for 2 hrs at room temperature.

6.4.2. Administration of ntPE-FcγRIII Antibody Delivery Construct to Mice

100 μg of the suspension of protein mixture is administered by oral gavage to BALB/c mice in 250 μl of PBS with 1 mg/ml of BSA as a carrier. Serum samples, prepared from blood collected at various time points, are analyzed for the presence of human IgG by ELISA.

6.4.3. Measurement of Human IgG in Mouse Serum Using Monoclonal Antibodie

Human IgG in mouse serum samples are measured by the ELISA described in Section 6.1.3, supra.

The present invention provides, inter alia, delivery constructs and methods of preventing, treating, managing or ameliorating a disorder in a subject. While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. Citation of these documents is not an admission that any particular reference is "prior art" to this invention.

TABLE 3

| Human Peptidases by Class | | | | |
|---|---|---|---|---|
| Aspartic-type peptidases | Cysteine-type peptidases | Metallopeptidases | Serine-type peptidases | Threonine-type peptidases |
| BAE1_HUMAN (P56817) | BLMH_HUMAN (Q13867) | AMPB_HUMAN (Q9H4A4) | ACRL_HUMAN (P58840) | PS7L_HUMAN (Q8TAA3) |
| BAE2_HUMAN (Q9Y5Z0) | CATB_HUMAN (P07858) | AMPE_HUMAN (Q07075) | ACRO_HUMAN (P10323) | PSA1_HUMAN (P25786) |
| CATD_HUMAN (P07339) | CATC_HUMAN (P53634) | AMPN_HUMAN (P15144) | APOA_HUMAN (P08519) | PSA2_HUMAN (P25787) |
| CATE_HUMAN (P14091) | CATF_HUMAN (Q9UBX1) | ART1_HUMAN (Q9NZ08) | BSS4_HUMAN (Q9GZN4) | PSA3_HUMAN (P25788) |
| NAP1_HUMAN (O96009) | CATH_HUMAN (P09668) | LCAP_HUMAN (Q9UIQ6) | C1R_HUMAN (P00736) | PSA4_HUMAN (P25789) |
| PEPA_HUMAN (P00790) | CATK_HUMAN (P43235) | LKHA_HUMAN (P09960) | C1S_HUMAN (P09871) | PSA5_HUMAN (P28066) |
| PEPC_HUMAN (P20142) | CATL_HUMAN (P07711) | PSA_HUMAN (P55786) | CAP7_HUMAN (P20160) | PSA6_HUMAN (P60900) |
| RENI_HUMAN (P00797) | CATO_HUMAN (P43234) | RNPL_HUMAN (Q9HAU8) | CATG_HUMAN (P08311) | PSA7_HUMAN (O14818) |
| VPRT_HUMAN (P10265) | CATS_HUMAN (P25774) | THDE_HUMAN (Q9UKU6) | CFAB_HUMAN (P00751) | PSB1_HUMAN (P20618) |

TABLE 3-continued

Human Peptidases by Class

| Aspartic-type peptidases | Cysteine-type peptidases | Metallopeptidases | Serine-type peptidases | Threonine-type peptidases |
|---|---|---|---|---|
| Other Peptidases | CATW_HUMAN (P56202) | ACET_HUMAN (P22966) | CFAD_HUMAN (P00746) | PSB2_HUMAN (P49721) |
| FAC2_HUMAN | CATZ_HUMAN (Q9UBR2) | ACE_HUMAN (P12821) | CFAI_HUMAN (P05156) | PSB3_HUMAN (P49720) |
| (Q9Y256) | CSL2_HUMAN (O60911) | MEPD_HUMAN (P52888) | CLCR_HUMAN (Q99895) | PSB4_HUMAN (P28070) |
| | TNAG_HUMAN (Q9UJW2) | NEUL_HUMAN (Q9BYT8) | CO2_HUMAN (P06681) | PSB5_HUMAN (P28074) |
| | CAN1_HUMAN (P07384) | PMIP_HUMAN (Q99797) | CORI_HUMAN (Q9Y5Q5) | PSB6_HUMAN (P28072) |
| | CAN2_HUMAN (P17655) | MM01_HUMAN (P03956) | CRAR_HUMAN (P48740) | PSB7_HUMAN (Q99436) |
| | CAN3_HUMAN (P20807) | MM02_HUMAN (P08253) | CTRB_HUMAN (P17538) | PSB8_HUMAN (P28062) |
| | CAN5_HUMAN (O15484) | MM03_HUMAN (P08254) | CTRL_HUMAN (P40313) | PSB9_HUMAN (P28065) |
| | CAN6_HUMAN (Q9Y6Q1) | MM07_HUMAN (P09237) | DES1_HUMAN (Q9UL52) | PSBA_HUMAN (P40306) |
| | CAN7_HUMAN (Q9Y6W3) | MM08_HUMAN (P22894) | EL1_HUMAN (Q9UN11) | |
| | CAN9_HUMAN (O14815) | MM09_HUMAN (P14780) | EL2A_HUMAN (P08217) | |
| | CANA_HUMAN (Q9HC96) | MM10_HUMAN (P09238) | EL2B_HUMAN (P08218) | |
| | CANB_HUMAN (Q9UMQ6) | MM11_HUMAN (P24347) | EL3A_HUMAN (P09093) | |
| | UBL1_HUMAN (P09936) | MM12_HUMAN (P39900) | EL3B_HUMAN (P08861) | |
| | UBL3_HUMAN (P15374) | MM13_HUMAN (P45452) | ELNE_HUMAN (P08246) | |
| | UBL5_HUMAN (Q9Y5K5) | MM14_HUMAN (P50281) | ENTK_HUMAN (P98073) | |
| | GPI8_HUMAN (Q92643) | MM15_HUMAN (P51511) | FA10_HUMAN (P00742) | |
| | LGMN_HUMAN (Q99538) | MM16_HUMAN (P51512) | FA11_HUMAN (P03951) | |
| | CFLA_HUMAN (O15519) | MM17_HUMAN (Q9ULZ9) | FA12_HUMAN (P00748) | |
| | IIBC_HUMAN (P29466) | MM19_HUMAN (Q99542) | FA7_HUMAN (P08709) | |
| | ICE2_HUMAN (P42575) | MM20_HUMAN (O60882) | FA9_HUMAN (P00740) | |
| | ICE3_HUMAN (P42574) | MM21_HUMAN (Q8N119) | GRAA_HUMAN (P12544) | |
| | ICE4_HUMAN (P49662) | MM24_HUMAN (Q9Y5R2) | GRAB_HUMAN (P10144) | |
| | ICE5_HUMAN (P51878) | MM25_HUMAN (Q9NPA2) | GRAH_HUMAN (P20718) | |
| | ICE6_HUMAN (P55212) | MM26_HUMAN (Q9NRE1) | GRAK_HUMAN (P49863) | |
| | ICE7_HUMAN (P55210) | MM28_HUMAN (Q9H239) | GRAM_HUMAN (P51124) | |
| | ICE8_HUMAN (Q14790) | BMP1_HUMAN (P13497) | HATT_HUMAN (O60235) | |
| | ICE9_HUMAN (P55211) | MEPA_HUMAN (Q16819) | HEPS_HUMAN (P05981) | |
| | ICEA_HUMAN (Q92851) | MEPB_HUMAN (Q16820) | HGFA_HUMAN (Q04756) | |
| | ICEE_HUMAN (P31944) | AD02_HUMAN (Q99965) | HGFL_HUMAN (P26927) | |
| | MLT1_HUMAN (Q9UDY8) | AD07_HUMAN (Q9H2U9) | HGF_HUMAN (P14210) | |
| | PGPI_HUMAN (Q9NXJ5) | AD08_HUMAN (P78325) | HPTR_HUMAN (P00739) | |
| | FAFX_HUMAN (Q93008) | AD09_HUMAN (Q13443) | HPT_HUMAN (P00738) | |
| | FAFY_HUMAN (O00507) | AD10_HUMAN (O14672) | KAL_HUMAN (P03952) | |
| | UB10_HUMAN (Q14694) | AD11_HUMAN (O75078) | KLK1_HUMAN (P06870) | |
| | UB11_HUMAN (P51784) | AD12_HUMAN (O43184) | KLK2_HUMAN (P20151) | |
| | UB12_HUMAN (O75317) | AD15_HUMAN (Q13444) | KLK3_HUMAN (P07288) | |
| | UB13_HUMAN (Q92995) | AD17_HUMAN (P78536) | KLK4_HUMAN (Q9Y5K2) | |
| | UB14_HUMAN (P54578) | AD18_HUMAN (Q9Y3Q7) | KLK5_HUMAN (Q9Y337) | |
| | UB15_HUMAN (Q9Y4E8) | AD19_HUMAN (Q9H013) | KLK6_HUMAN (Q92876) | |
| | UB16_HUMAN (Q9Y5T5) | AD20_HUMAN (O43506) | KLK7_HUMAN (P49862) | |
| | UB18_HUMAN (Q9UMW8) | AD21_HUMAN (Q9UKJ8) | KLK8_HUMAN (O60259) | |
| | UB19_HUMAN (O94966) | AD22_HUMAN (Q9P0K1) | KLK9_HUMAN (Q9UKQ9) | |
| | UB20_HUMAN (Q9Y2K6) | AD28_HUMAN (Q9UKQ2) | KLKA_HUMAN (O43240) | |
| | UB21_HUMAN (Q9UK80) | AD29_HUMAN (Q9UKF5) | KLKB_HUMAN (Q9UBX7) | |
| | UB22_HUMAN (Q9UPT9) | AD30_HUMAN (Q9UKF2) | KLKC_HUMAN (Q9UKR0) | |
| | UB24_HUMAN (Q9UPU5) | AD33_HUMAN (Q9BZ11) | KLKD_HUMAN (Q9UKR3) | |
| | UB25_HUMAN (Q9UHP3) | AT10_HUMAN (Q9H324) | KLKE_HUMAN (Q9P0G3) | |
| | UB26_HUMAN (Q9BXU7) | AT12_HUMAN (P58397) | KLKF_HUMAN (Q9H2R5) | |
| | UB28_HUMAN (Q96RU2) | AT14_HUMAN (Q8WXS8) | LCLP_HUMAN (P34168) | |
| | UB29_HUMAN (Q9HBJ7) | AT15_HUMAN (Q8TE58) | MAS2_HUMAN (O00187) | |
| | UB32_HUMAN (Q8NFA0) | AT16_HUMAN (Q8TE57) | MCT1_HUMAN (P23946) | |
| | UB33_HUMAN (Q8TEY7) | AT17_HUMAN (Q8TE56) | NETR_HUMAN (P56730) | |
| | UB35_HUMAN (Q9P2H5) | AT18_HUMAN (Q8TE60) | PLMN_HUMAN (P00747) | |
| | UB36_HUMAN (Q9P275) | AT19_HUMAN (Q8TE59) | PR27_HUMAN (Q9BQR3) | |
| | UB37_HUMAN (Q86T82) | AT20_HUMAN (P59510) | PRN3_HUMAN (P24158) | |
| | UB38_HUMAN (Q8NB14) | ATS1_HUMAN (Q9UHI8) | PRTC_HUMAN (P04070) | |
| | UB40_HUMAN (Q9NVE5) | ATS2_HUMAN (Q95450) | PRTZ_HUMAN (P22891) | |
| | UB42_HUMAN (Q9H9J4) | ATS3_HUMAN (O15072) | PS23_HUMAN (O95084) | |
| | UB44_HUMAN (Q9H0E7) | ATS4_HUMAN (O75173) | PSS8_HUMAN (Q16651) | |
| | UB46_HUMAN (P62068) | ATS5_HUMAN (Q9UNA0) | ST14_HUMAN (Q9Y5Y6) | |
| | UBP1_HUMAN (O94782) | ATS6_HUMAN (Q9UKP5) | TEST_HUMAN (Q9Y6M0) | |
| | UBP2_HUMAN (O75604) | ATS7_HUMAN (Q9UKP4) | THRB_HUMAN (P00734) | |
| | UBP3_HUMAN (Q9Y6I4) | ATS8_HUMAN (Q9UP79) | TMS2_HUMAN (O15393) | |
| | UBP4_HUMAN (Q13107) | ATS9_HUMAN (Q9P2N4) | TMS3_HUMAN (P57727) | |
| | UBP5_HUMAN (P45974) | ECE1_HUMAN (P42892) | TMS4_HUMAN (Q9NRS4) | |
| | UBP6_HUMAN (P35125) | ECE2_HUMAN (O60344) | TMS5_HUMAN (Q9H3S3) | |
| | UBP7_HUMAN (Q93009) | ECEL_HUMAN (O95672) | TMS6_HUMAN (Q8IU80) | |
| | UBP8_HUMAN (P40818) | KELL_HUMAN (P23276) | TPA_HUMAN (P00750) | |
| | GGH_HUMAN (Q92820) | NEP_HUMAN (P08473) | TRB1_HUMAN (Q15661) | |
| | SEN1_HUMAN (Q9P0U3) | PEX_HUMAN (P78562) | TRB2_HUMAN (P20231) | |
| | SEN3_HUMAN (Q9H4L4) | CBP1_HUMAN (P15085) | TRY1_HUMAN (P07477) | |
| | SEN5_HUMAN (Q96HI0) | CBP2_HUMAN (P48052) | TRY2_HUMAN (P07478) | |
| | SEN6_HUMAN (Q9GZR1) | CBP4_HUMAN (Q9UI42) | TRY3_HUMAN (P35030) | |
| | SEN7_HUMAN (Q9BQF6) | CBP5_HUMAN (Q8WXQ8) | TRYA_HUMAN (P15157) | |

TABLE 3-continued

Human Peptidases by Class

| Aspartic-type peptidases | Cysteine-type peptidases | Metallopeptidases | Serine-type peptidases | Threonine-type peptidases |
|---|---|---|---|---|
| | SEN8_HUMAN (Q96LD8) | CBP6_HUMAN (Q8N4T0) | TRYD_HUMAN (Q9BZJ3) | |
| | SNP2_HUMAN (Q9HC62) | CBPB_HUMAN (P15086) | TRYG_HUMAN (Q9NRR2) | |
| | ESP1_HUMAN (Q14674) | CBPC_HUMAN (P15088) | TS50_HUMAN (Q9UI38) | |
| | | CBPD_HUMAN (O75976) | UROK_HUMAN (P00749) | |
| | | CBPE_HUMAN (P16870) | HRA1_HUMAN (Q92743) | |
| | | CBPM_HUMAN (P14384) | HRA2_HUMAN (O43464) | |
| | | CBPN_HUMAN (P15169) | HRA3_HUMAN (P83110) | |
| | | CPX2_HUMAN (Q8N436) | HRA4_HUMAN (P83105) | |
| | | CPXM_HUMAN (Q96SM3) | FURI_HUMAN (P09958) | |
| | | IDE_HUMAN (P14735) | MS1P_HUMAN (Q14703) | |
| | | MPPA_HUMAN (Q10713) | NEC1_HUMAN (P29120) | |
| | | MPPB_HUMAN (O75439) | NEC2_HUMAN (P16519) | |
| | | NRDC_HUMAN (O43847) | PCK5_HUMAN (Q92824) | |
| | | UCR1_HUMAN (P31930) | PCK6_HUMAN (P29122) | |
| | | UCR2_HUMAN (P22695) | PCK7_HUMAN (Q16549) | |
| | | AMPL_HUMAN (P28838) | PCK9_HUMAN (Q8NBP7) | |
| | | PEL1_HUMAN (Q8NDH3) | TPP2_HUMAN (P29144) | |
| | | DNPE_HUMAN (Q9ULA0) | PPCE_HUMAN (P48147) | |
| | | MDP1_HUMAN (P16444) | DPP4_HUMAN (P27487) | |
| | | CGL1_HUMAN (Q96KP4) | DPP6_HUMAN (P42658) | |
| | | CGL2_HUMAN (Q96KN2) | SEPR_HUMAN (Q12884) | |
| | | ACY1_HUMAN (Q03154) | ACPH_HUMAN (P13798) | |
| | | GCP_HUMAN (Q9NPF4) | CPVL_HUMAN (Q9H3G5) | |
| | | AMP1_HUMAN (P53582) | PRTP_HUMAN (P10619) | |
| | | PEPD_HUMAN (P12955) | RISC_HUMAN (Q9HB40) | |
| | | XPP2_HUMAN (O43895) | CLPP_HUMAN (Q16740) | |
| | | AMP2_HUMAN (P50579) | LONM_HUMAN (P36776) | |
| | | P2G4_HUMAN (Q9UQ80) | SPC3_HUMAN (Q9BY50) | |
| | | FOH1_HUMAN (Q04609) | SPC4_HUMAN (P21378) | |
| | | NLD2_HUMAN (Q9Y3Q0) | DPP2_HUMAN (Q9UHL4) | |
| | | NLDL_HUMAN (Q9UQQ1) | PCP_HUMAN (P42785) | |
| | | TFR1_HUMAN (P02786) | TSSP_HUMAN (Q9NQE7) | |
| | | TFR2_HUMAN (Q9UP52) | HYEP_HUMAN (P07099) | |
| | | AF31_HUMAN (O43931) | TPP1_HUMAN (O14773) | |
| | | AF32_HUMAN (Q9Y4W6) | RHB1_HUMAN (O75783) | |
| | | SPG7_HUMAN (Q9UQ90) | RHB2_HUMAN (Q9NX52) | |
| | | YME1_HUMAN (Q96TA2) | RHB4_HUMAN (P58872) | |
| | | PAPA_HUMAN (Q13219) | | |
| | | FAC1_HUMAN (O75844) | | |
| | | DPP3_HUMAN (Q9NY33) | | |
| | | MS2P_HUMAN (O43462) | | |

SEQUENCE LISTING

<160> NUMBER OF SEQ ID NOS: 34

<210> SEQ ID NO 1
<211> LENGTH: 266
<212> TYPE: PRT
<213> ORGANISM: Pseudomonas
<220> FEATURE:
<223> OTHER INFORMATION: receptor binding domain of Pseudomonas exotoxin
      A

<400> SEQUENCE: 1

```
Met His Leu Ile Pro His Trp Ile Pro Leu Val Ala Ser Leu Gly Leu
 1               5                  10                  15

Leu Ala Gly Gly Ser Ser Ala Ser Ala Ala Glu Glu Ala Phe Asp Leu
            20                  25                  30

Trp Asn Glu Cys Ala Lys Ala Cys Val Leu Asp Leu Lys Asp Gly Val
        35                  40                  45

Arg Ser Ser Arg Met Ser Val Asp Pro Ala Ile Ala Asp Thr Asn Gly
    50                  55                  60
```

-continued

```
Gln Gly Val Leu His Tyr Ser Met Val Leu Glu Gly Gly Asn Asp Ala
65                  70                  75                  80

Leu Lys Leu Ala Ile Asp Asn Ala Leu Ser Ile Thr Ser Asp Gly Leu
                85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro
            260                 265

<210> SEQ ID NO 2
<211> LENGTH: 153
<212> TYPE: PRT
<213> ORGANISM: Pseudomonas
<220> FEATURE:
<223> OTHER INFORMATION: Pseudomonas exotoxin A transcytosis domain

<400> SEQUENCE: 2

Thr Val Ile Ser His Arg Leu His Phe Pro Glu Gly Gly Ser Leu Ala
 1               5                  10                  15

Ala Leu Thr Ala His Gln Ala Cys His Leu Pro Leu Glu Thr Phe Thr
            20                  25                  30

Arg His Arg Gln Pro Arg Gly Trp Glu Gln Leu Glu Gln Cys Gly Tyr
        35                  40                  45

Pro Val Gln Arg Leu Val Ala Leu Tyr Leu Ala Ala Arg Leu Ser Trp
    50                  55                  60

Asn Gln Val Asp Gln Val Ile Arg Asn Ala Leu Ala Ser Pro Gly Ser
65                  70                  75                  80

Gly Gly Asp Leu Gly Glu Ala Ile Arg Glu Gln Pro Glu Gln Ala Arg
                85                  90                  95

Leu Ala Leu Thr Leu Ala Ala Ala Glu Ser Glu Arg Phe Val Arg Gln
            100                 105                 110

Gly Thr Gly Asn Asp Glu Ala Gly Ala Ala Asn Ala Asp Val Val Ser
        115                 120                 125

Leu Thr Cys Pro Val Ala Ala Gly Glu Cys Ala Gly Pro Ala Asp Ser
    130                 135                 140

Gly Asp Ala Leu Leu Glu Arg Asn Tyr
145                 150
```

<210> SEQ ID NO 3
<211> LENGTH: 1839
<212> TYPE: DNA
<213> ORGANISM: Artificial Sequence
<220> FEATURE:
<223> OTHER INFORMATION: Nucleotide sequence encoding PE

<400> SEQUENCE: 3

```
gccgaagaag ctttcgacct ctggaacgaa tgcgccaaag cctgcgtgct cgacctcaag      60
gacggcgtgc gttccagccg catgagcgtc gacccggcca tcgccgacac caacggccag     120
ggcgtgctgc actactccat ggtcctggag gcggcaacg acgcgctcaa gctggccatc      180
gacaacgccc tcagcatcac cagcgacggc ctgaccatcc gcctcgaagg cggcgtcgag     240
ccgaacaagc cggtgcgcta cagctacacg cgccaggcgc gcggcagttg gtcgctgaac     300
tggctggtac cgatcggcca cgagaagccc tcgaacatca aggtgttcat ccacgaactg     360
aacgccggca accagctcag ccacatgtcg ccgatctaca ccatcgagat gggcgacgag     420
ttgctggcga gctggcgcg cgatgccacc ttcttcgtca gggcgcacga gagcaacgag      480
atgcagccga cgctcgccat cagccatgcc ggggtcagcg tggtcatggc ccagacccag     540
ccgcgccggg aaaagcgctg gagcgaatgg gccagcggca aggtgttgtg cctgctcgac     600
ccgctggacg gggtctacaa ctacctcgcc cagcaacgct gcaacctcga cgatacctgg     660
gaaggcaaga tctaccgggt gctcgccggc aacccggcga agcatgacct ggacatcaaa     720
cccacggtca tcagtcatcg cctgcacttt cccgagggcg gcagcctggc cgcgctgacc     780
gcgcaccagg cttgccacct gccgctggag actttcaccc gtcatcgcca gccgcgcggc     840
tgggaacaac tggagcagtg cggctatccg gtgcagcggc tggtcgccct ctacctggcg     900
gcgcggctgt cgtggaacca ggtcgaccag gtgatccgca acgccctggc cagccccggc     960
agcggcggcg acctgggcga agcgatccgc gagcagccgg agcaggcccg tctggcctg     1020
accctggccc cgccgagag cgagcgcttc gtccggcagg gcaccggcaa cgacgaggcc     1080
ggcgcggcca acgccgacgt ggtgagcctg acctgcccgg tcgccgccgg tgaatgcgcg     1140
ggcccggcg acagcggcga cgccctgctg agcgcaact atcccactgg cgcggagttc      1200
ctcggcgacg gcggcgacgt cagcttcagc acccgcggca cgcagaactg gacggtggag     1260
cggctgctcc aggcgcaccg ccaactggag gagcgcggct atgtgttcgt cggctaccac     1320
ggcaccttcc tcgaagcggc gcaaagcatc gtcttcggcg gggtgcgcgc gcgcagccag     1380
gacctcgacg cgatctggcg cggttttctat atcgccggcg atccggcgct ggcctacggc     1440
tacgcccagg accaggaacc cgacgcacgc ggccggatcc gcaacggtgc cctgctgcgg     1500
gtctatgtgc cgcgctcgag cctgccgggc ttctaccgca ccagcctgac cctggccgcg     1560
ccggaggcgg cgggcgaggt cgaacggctg atcggccatc cgctgccgct gcgcctggac     1620
gccatcaccg gccccgagga ggaaggcggg cgcctggaga ccattctcgg ctggccgctg     1680
gccgagcgca ccgtggtgat tccctcggcg atccccaccg accgcgcaa cgtcggcggc     1740
gacctcgacc cgtccagcat ccccgacaag gaacaggcga tcagcgccct gccggactac     1800
gccagccagc ccggcaaacc gccgcgcgag gacctgaag                           1839
```

<210> SEQ ID NO 4
<211> LENGTH: 4
<212> TYPE: PRT
<213> ORGANISM: Artificial Sequence
<220> FEATURE:
<223> OTHER INFORMATION: Peptide recognized by Cathepsin GI

```
<400> SEQUENCE: 4

Ala Ala Pro Phe
1

<210> SEQ ID NO 5
<211> LENGTH: 3
<212> TYPE: PRT
<213> ORGANISM: Artificial Sequence
<220> FEATURE:
<223> OTHER INFORMATION: Peptide recognized by Chymotrypsin I

<400> SEQUENCE: 5

Gly Gly Phe
1

<210> SEQ ID NO 6
<211> LENGTH: 4
<212> TYPE: PRT
<213> ORGANISM: Artificial Sequence
<220> FEATURE:
<223> OTHER INFORMATION: Peptide recognized by Elastase I

<400> SEQUENCE: 6

Ala Ala Pro Val
1

<210> SEQ ID NO 7
<211> LENGTH: 3
<212> TYPE: PRT
<213> ORGANISM: Artificial Sequence
<220> FEATURE:
<223> OTHER INFORMATION: Peptide recognized by Subtilisin AI

<400> SEQUENCE: 7

Gly Gly Leu
1

<210> SEQ ID NO 8
<211> LENGTH: 3
<212> TYPE: PRT
<213> ORGANISM: Artificial Sequence
<220> FEATURE:
<223> OTHER INFORMATION: Peptide recognized by SubtilisIn AII

<400> SEQUENCE: 8

Ala Ala Leu
1

<210> SEQ ID NO 9
<211> LENGTH: 3
<212> TYPE: PRT
<213> ORGANISM: Artificial Sequence
<220> FEATURE:
<223> OTHER INFORMATION: Peptide recognized by Thrombin I

<400> SEQUENCE: 9

Phe Val Arg
1

<210> SEQ ID NO 10
<211> LENGTH: 3
<212> TYPE: PRT
<213> ORGANISM: Artificial Sequence
<220> FEATURE:
<223> OTHER INFORMATION: Peptide recognized by Urokinase I
```

```
<400> SEQUENCE: 10

Val Gly Arg
  1

<210> SEQ ID NO 11
<211> LENGTH: 5
<212> TYPE: PRT
<213> ORGANISM: Artificial Sequence
<220> FEATURE:
<221> NAME/KEY: VARIANT
<222> LOCATION: 5
<223> OTHER INFORMATION: Xaa = Any Amino Acid
<220> FEATURE:
<223> OTHER INFORMATION: Peptide(s) recognized by Caspase-1

<400> SEQUENCE: 11

Tyr Val Ala Asp Xaa
  1               5

<210> SEQ ID NO 12
<211> LENGTH: 5
<212> TYPE: PRT
<213> ORGANISM: Artificial Sequence
<220> FEATURE:
<221> NAME/KEY: VARIANT
<222> LOCATION: 2,3,5
<223> OTHER INFORMATION: Xaa = Any Amino Acid
<220> FEATURE:
<223> OTHER INFORMATION: Peptide(s) recognized by Caspase-3

<400> SEQUENCE: 12

Asp Xaa Xaa Asp Xaa
  1               5

<210> SEQ ID NO 13
<211> LENGTH: 4
<212> TYPE: PRT
<213> ORGANISM: Artificial Sequence
<220> FEATURE:
<221> NAME/KEY: VARIANT
<222> LOCATION: 2,4
<223> OTHER INFORMATION: Xaa = Any Amino Acid
<220> FEATURE:
<221> NAME/KEY: VARIANT
<222> LOCATION: 2
<223> OTHER INFORMATION: Xaa can be repeated 0, 2, 4 or 6 times
<220> FEATURE:
<223> OTHER INFORMATION: Peptide(s) recognized by Proprotein convertase
      1

<400> SEQUENCE: 13

Arg Xaa Arg Xaa
  1

<210> SEQ ID NO 14
<211> LENGTH: 4
<212> TYPE: PRT
<213> ORGANISM: Artificial Sequence
<220> FEATURE:
<221> NAME/KEY: VARIANT
<222> LOCATION: 2,4
<223> OTHER INFORMATION: Xaa = Any Amino Acid
<220> FEATURE:
<221> NAME/KEY: VARIANT
<222> LOCATION: 2
<223> OTHER INFORMATION: Xaa can be repeated 0, 2, 4 or 6 times
<220> FEATURE:
<223> OTHER INFORMATION: Peptide(s) recognized by Proprotein convertase
      2
```

```
-continued

<400> SEQUENCE: 14

Lys Xaa Arg Xaa
 1

<210> SEQ ID NO 15
<211> LENGTH: 6
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = Any Amino Acid
<220> FEATURE:
<223> OTHER INFORMATION: Peptide(s) recognized by Proprotein convertase
      4

<400> SEQUENCE: 15

Gly Arg Thr Lys Arg Xaa
 1               5

<210> SEQ ID NO 16
<211> LENGTH: 5
<212> TYPE: PRT
<213> ORGANISM: Artificial Sequence
<220> FEATURE:
<221> NAME/KEY: VARIANT
<222> LOCATION: 5
<223> OTHER INFORMATION: Xaa = Any Amino Acid
<220> FEATURE:
<223> OTHER INFORMATION: Peptide(s) recognized by Proprotein convertase
      4 (PACE 4)

<400> SEQUENCE: 16

Arg Val Arg Arg Xaa
 1               5

<210> SEQ ID NO 17
<211> LENGTH: 6
<212> TYPE: PRT
<213> ORGANISM: Artificial Sequence
<220> FEATURE:
<221> NAME/KEY: VARIANT
<222> LOCATION: 6
<223> OTHER INFORMATION: Xaa = Any Amino Acid
<220> FEATURE:
<223> OTHER INFORMATION: Peptide(s) recognized by Proprotein convertase
      4 PACE 4

<400> SEQUENCE: 17

Asp Arg Val Arg Arg Xaa
 1               5

<210> SEQ ID NO 18
<211> LENGTH: 6
<212> TYPE: PRT
<213> ORGANISM: Artificial Sequence
<220> FEATURE:
<221> NAME/KEY: VARIANT
<222> LOCATION: 2,6
<223> OTHER INFORMATION: Xaa = Any Amino Acid
<220> FEATURE:
<223> OTHER INFORMATION: Peptide(s) recognized by Prolyloligopeptidase
      Endothelin cleaving enzyme with
      dipeptidyl-peptidase IV

<400> SEQUENCE: 18

Pro Xaa Trp Val Pro Xaa
 1               5
```

```
<210> SEQ ID NO 19
<211> LENGTH: 4
<212> TYPE: PRT
<213> ORGANISM: Artificial Sequence
<220> FEATURE:
<221> NAME/KEY: VARIANT
<222> LOCATION: 4
<223> OTHER INFORMATION: Xaa = Any Amino Acid
<220> FEATURE:
<223> OTHER INFORMATION: Peptide(s) recognized by Signal Peptidase

<400> SEQUENCE: 19

Trp Val Ala Xaa
 1

<210> SEQ ID NO 20
<211> LENGTH: 4
<212> TYPE: PRT
<213> ORGANISM: Artificial Sequence
<220> FEATURE:
<221> NAME/KEY: VARIANT
<222> LOCATION: 1,3,4
<223> OTHER INFORMATION: Xaa = Any Amino Acid
<220> FEATURE:
<223> OTHER INFORMATION: Peptide(s) recognized by Neprilysin in
      combination with dipeptidyl-peptidase IV

<400> SEQUENCE: 20

Xaa Phe Xaa Xaa
 1

<210> SEQ ID NO 21
<211> LENGTH: 4
<212> TYPE: PRT
<213> ORGANISM: Artificial Sequence
<220> FEATURE:
<221> NAME/KEY: VARIANT
<222> LOCATION: 1,3,4
<223> OTHER INFORMATION: Xaa = Any Amino Acid
<220> FEATURE:
<223> OTHER INFORMATION: Peptide(s) recognized by Neprilysin in
      combination with dipeptidyl-peptidase IV

<400> SEQUENCE: 21

Xaa Tyr Xaa Xaa
 1

<210> SEQ ID NO 22
<211> LENGTH: 4
<212> TYPE: PRT
<213> ORGANISM: Artificial Sequence
<220> FEATURE:
<221> NAME/KEY: VARIANT
<222> LOCATION: 1,3,4
<223> OTHER INFORMATION: Xaa = Any Amino Acid
<220> FEATURE:
<223> OTHER INFORMATION: Peptide(s) recognized by Neprilysin in
      combination with dipeptidyl-peptidase IV

<400> SEQUENCE: 22

Xaa Trp Xaa Xaa
 1

<210> SEQ ID NO 23
<211> LENGTH: 12
<212> TYPE: PRT
<213> ORGANISM: Artificial Sequence
<220> FEATURE:
<221> NAME/KEY: VARIANT
<222> LOCATION: 10
<223> OTHER INFORMATION: Xaa = Val, Ala or Pro
```

```
<220> FEATURE:
<221> NAME/KEY: VARIANT
<222> LOCATION: 12
<223> OTHER INFORMATION: Xaa = Ser, Pro or Ala
<220> FEATURE:
<223> OTHER INFORMATION: Peptide(s) recognized by Renin in combination
      with dipeptidyl-peptidase IV

<400> SEQUENCE: 23

Asp Arg Tyr Ile Pro Phe His Leu Leu Xaa Tyr Xaa
1               5                   10

<210> SEQ ID NO 24
<211> LENGTH: 63
<212> TYPE: PRT
<213> ORGANISM: homo sapiens
<220> FEATURE:
<223> OTHER INFORMATION: Fc-binder domain of Protein G

<400> SEQUENCE: 24

Val Arg Gln Gly Thr Gly Asn Thr Thr Tyr Lys Leu Val Ile Asn Gly
1               5                   10                  15

Lys Thr Leu Lys Gly Glu Thr Thr Thr Glu Ala Val Asp Ala Ala Thr
            20                  25                  30

Ala Glu Lys Val Phe Lys Gln Tyr Ala Asn Asp Asn Gly Val Asp Gly
        35                  40                  45

Glu Trp Thr Tyr Asp Asp Ala Thr Lys Thr Phe Thr Val Thr Glu
    50                  55                  60

<210> SEQ ID NO 25
<211> LENGTH: 68
<212> TYPE: PRT
<213> ORGANISM: homo sapiens
<220> FEATURE:
<223> OTHER INFORMATION: Protein A antibody-binding fragment

<400> SEQUENCE: 25

Val Arg Gln Gly Thr Gly Asn Thr Ala Asp Asn Lys Phe Asn Lys Glu
1               5                   10                  15

Gln Gln Asn Ala Phe Tyr Glu Ile Leu His Leu Pro Asn Leu Asn Trp
            20                  25                  30

Trp Gln Arg Asn Gly Phe Ile Gln Ser Leu Lys Asp Asp Pro Ser Gln
        35                  40                  45

Ser Ala Asn Asn Leu Leu Ala Glu Ala Lys Lys Leu Asn Asp Ala Gln
    50                  55                  60

Ala Pro Lys Ala
65

<210> SEQ ID NO 26
<211> LENGTH: 365
<212> TYPE: PRT
<213> ORGANISM: homo sapiens
<220> FEATURE:
<223> OTHER INFORMATION: human FcRn

<400> SEQUENCE: 26

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45
```

```
Val Ser Gly Trp Leu Gly Pro Gln Gln Tyr Leu Ser Tyr Asn Ser Leu
 50                  55                  60

Arg Gly Glu Ala Glu Pro Cys Gly Ala Trp Val Trp Glu Asn Gln Val
 65                  70                  75                  80

Ser Trp Tyr Trp Glu Lys Glu Thr Thr Asp Leu Arg Ile Lys Glu Lys
                 85                  90                  95

Leu Phe Leu Glu Ala Phe Lys Ala Leu Gly Lys Gly Pro Tyr Thr
                100                 105                 110

Leu Gln Gly Leu Leu Gly Cys Glu Leu Gly Pro Asp Asn Thr Ser Val
                115                 120                 125

Pro Thr Ala Lys Phe Ala Leu Asn Gly Glu Glu Phe Met Asn Phe Asp
     130                 135                 140

Leu Lys Gln Gly Thr Trp Gly Gly Asp Trp Pro Glu Ala Leu Ala Ile
 145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
                180                 185                 190

Gly Arg Gly Asn Leu Glu Trp Lys Glu Pro Pro Ser Met Arg Leu Lys
                195                 200                 205

Ala Arg Pro Ser Ser Pro Gly Phe Ser Val Leu Thr Cys Ser Ala Phe
     210                 215                 220

Ser Phe Tyr Pro Pro Glu Leu Gln Leu Arg Phe Leu Arg Asn Gly Leu
 225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
                260                 265                 270

Tyr Cys Cys Ile Val Gln His Ala Gly Leu Ala Gln Pro Leu Arg Val
     275                 280                 285

Glu Leu Glu Ser Pro Ala Lys Ser Ser Val Leu Val Val Gly Ile Val
 290                 295                 300

Ile Gly Val Leu Leu Leu Thr Ala Ala Ala Val Gly Gly Ala Leu Leu
 305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
                340                 345                 350

Ala Asp Leu Lys Asp Val Asn Val Ile Pro Ala Thr Ala
     355                 360                 365

<210> SEQ ID NO 27
<211> LENGTH: 224
<212> TYPE: PRT
<213> ORGANISM: homo sapiens
<220> FEATURE:
<223> OTHER INFORMATION: human Fc gamma RIII

<400> SEQUENCE: 27

His Thr Cys Pro Pro Cys Pro Ala Pro Glu Leu Leu Gly Gly Pro Ser
  1               5                  10                  15

Val Phe Leu Phe Pro Pro Lys Pro Lys Asp Thr Leu Met Ile Ser Arg
                 20                  25                  30

Thr Pro Glu Val Thr Cys Val Val Val Asp Val Ser His Glu Asp Pro
                 35                  40                  45
```

```
Gln Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asn Trp Leu Asp Gly Lys Glu Tyr
                 85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
            115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro Gly Lys
210                 215                 220

<210> SEQ ID NO 28
<211> LENGTH: 233
<212> TYPE: PRT
<213> ORGANISM: homo sapiens
<220> FEATURE:
<223> OTHER INFORMATION: human Fc gamma RIII - beta

<400> SEQUENCE: 28

Met Trp Gln Leu Leu Leu Pro Thr Ala Leu Leu Leu Leu Val Ser Ala
 1               5                  10                  15

Gly Met Arg Thr Glu Asp Leu Pro Lys Ala Val Val Phe Leu Glu Pro
             20                  25                  30

Gln Trp Tyr Ser Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
 65                  70                  75                  80

Val Asn Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190
```

-continued

```
Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 29
<211> LENGTH: 143
<212> TYPE: PRT
<213> ORGANISM: homo sapiens
<220> FEATURE:
<223> OTHER INFORMATION: antibody-binding domain of human Fc gamma
      RIII - beta

<400> SEQUENCE: 29

Asn Leu Ser Thr Leu Ser Asp Pro Val Gln Leu Glu Val His Ile Gly
 1               5                  10                  15

Trp Leu Leu Leu Gln Ala Pro Arg Trp Val Phe Lys Glu Glu Asp Pro
            20                  25                  30

Ile His Leu Arg Cys His Ser Trp Lys Asn Thr Ala Leu His Lys Val
        35                  40                  45

Thr Tyr Leu Gln Asn Gly Lys Asp Arg Lys Tyr Phe His His Asn Ser
    50                  55                  60

Asp Phe His Ile Pro Lys Ala Thr Leu Lys Asp Ser Gly Ser Tyr Phe
65                  70                  75                  80

Cys Arg Gly Leu Val Gly Ser Lys Asn Ile Val Ser Ser Glu Thr Val
                85                  90                  95

Asn Ile Thr Ile Thr Gln Gly Leu Ala Val Ser Thr Ile Ser Ser Phe
            100                 105                 110

Ser Pro Pro Gly Tyr Gln Val Ser Phe Cys Ile Val Met Val Leu Leu
        115                 120                 125

Phe Ala Val Asp Thr Tyr Leu Tyr Phe Ser Val Lys Thr Asn Ile
    130                 135                 140

<210> SEQ ID NO 30
<211> LENGTH: 7
<212> TYPE: PRT
<213> ORGANISM: Artificial Sequence
<220> FEATURE:
<223> OTHER INFORMATION: cleavable linker for ntPE-Fc gamma RIII carrier
      construct

<400> SEQUENCE: 30

Arg Gln Pro Arg Gly Gly Leu
 1               5

<210> SEQ ID NO 31
<211> LENGTH: 7
<212> TYPE: PRT
<213> ORGANISM: Artificial Sequence
<220> FEATURE:
<223> OTHER INFORMATION: cleavable linker for ntPE-Fc gamma RIII carrier
      construct

<400> SEQUENCE: 31

Gly Gly Leu Arg Gln Pro Arg
 1               5
```

```
<210> SEQ ID NO 32
<211> LENGTH: 7
<212> TYPE: PRT
<213> ORGANISM: Artificial Sequence
<220> FEATURE:
<223> OTHER INFORMATION: cleavable linker for ntPE-Fc gamma RIII carrier
      construct

<400> SEQUENCE: 32

Arg Gln Pro Arg Glu Gly Arg
 1               5

<210> SEQ ID NO 33
<211> LENGTH: 7
<212> TYPE: PRT
<213> ORGANISM: Artificial Sequence
<220> FEATURE:
<223> OTHER INFORMATION: cleavable linker for ntPE-Fc gamma RIII carrier
      construct

<400> SEQUENCE: 33

Arg Gln Pro Arg Val Gly Arg
 1               5

<210> SEQ ID NO 34
<211> LENGTH: 7
<212> TYPE: PRT
<213> ORGANISM: Artificial Sequence
<220> FEATURE:
<223> OTHER INFORMATION: cleavable linker for ntPE-Fc gamma RIII carrier
      construct

<400> SEQUENCE: 34

Arg Gln Pro Arg Ala Arg Arg
 1               5
```

What is claimed is:

1. A delivery construct, comprising an isolated carrier construct non-covalently bound to an isolated antibody, wherein said carrier construct comprises:
   a) a receptor-binding domain, wherein said receptor-binding domain (i) binds to a cell-surface receptor that is selected from the group consisting of α2-macroglobulin receptor, epidermal growth factor receptor, transferrin receptor, chemokine receptor, CD25, CD11B, CD11C, CD80, CD86, TNFα receptor, TOLL receptor, M-CSF receptor, GM-CSF receptor, scavenger receptor, and VEGF receptor, or (ii) is selected from the group consisting of a receptor-binding domain from *Pseudomonas* exotoxin A; cholera toxin; botulinum toxin; diptheria toxin; shiga toxin; shiga-like toxin; TGF α; EGF; IGF-I; IGF-II; IGF-III; IL-1; IL-2; IL-3; IL-6; MIP-1a; MIP-1b; MCAF; and IL-8, b) a transcytosis domain, and c) an antibody-binding domain to which the antibody non-covalently binds, wherein said antibody-binding domain is an Fc binding domain.

2. The delivery construct of claim 1, wherein said Fc binding domain is a Protein G, Protein A, an Fc receptor, or an antibody-binding fragment thereof.

3. The delivery construct of claim 2, wherein said Fc receptor is Fc receptor γ or neonatal Fc receptor.

4. The delivery construct of claim 1, wherein the antibody is selected from the group consisting of a monoclonal antibody, a human antibody, a humanized antibody, a chimeric antibody, a single chain antibody, a single domain antibody, an antigen-binding antibody fragment, a Fab fragment and a F(ab')2 fragment.

5. The delivery construct of claim 1, wherein the antibody is selected from rituximab, bevacizumab, trastuzumab, cetuximab, natalizumab, infliximab, etanercept, adalimumab, omalizumab, and efalizumab.

6. The delivery construct of claim 1, wherein the carrier construct further comprises a cleavable linker, wherein cleavage at said cleavable linker separates said antibody-binding domain from the remainder of said carrier construct, and wherein said cleavable linker is cleavable by an enzyme that i) exhibits greater activity at a basal-lateral membrane of a polarized epithelial cell than at an apical membrane of the polarized epithelial cell, or ii) exhibits greater activity in the plasma of a subject than at an apical membrane of the polarized epithelial cell of the subject.

7. The delivery construct of claim 6, wherein said cleavable linker comprises an amino acid sequence that is selected from the group consisting of Ala-Ala-Pro-Phe (SEQ ID NO.:4), Gly-Gly-Phe (SEQ ID NO.:5), Ala-Ala-Pro-Val (SEQ ID NO.:6), Gly-Gly-Leu (SEQ ID NO.:7), Ala-Ala-Leu (SEQ ID NO.:8), Phe-Val-Arg (SEQ ID NO.:9), Val-Gly-Arg (SEQ ID NO.:10).

8. The delivery construct of claim 6, wherein the epithelial cell is selected from the group consisting of nasal epithelial cells, oral epithelial cells, intestinal epithelial cells, rectal epithelial cells, vaginal epithelial cells, and pulmonary epithelial cells.

9. The delivery construct of claim 6, wherein said enzyme that is present at a basal-lateral membrane of a polarized epithelial cell is selected from the group consisting of Cathepsin GI, Chymotrypsin I, Elastase I, Subtilisin AI, Subtilisin AII, Thrombin I, and Urokinase I.

10. The delivery construct of claim 1, wherein said receptor-binding domain is selected from the group consisting of a receptor-binding domain from *Pseudomonas* exotoxin A; cholera toxin; botulinum toxin; diptheria toxin; shiga toxin; shiga-like toxin; TGF α; EGF; IGF-I; IGF-II; IGF-III; IL-1; IL-2; IL-3; IL-6; MIP-1a; MIP-1b; MCAF; and IL-8.

11. The delivery construct of claim 1, wherein said receptor-binding domain binds to an α2-macroglobulin receptor.

12. The delivery construct of claim 10, wherein said receptor-binding domain of *Pseudomonas* exotoxin A is Domain Ia of *Pseudomonas* exotoxin A.

13. The delivery construct of claim 10, wherein said receptor-binding domain of *Pseudomonas* exotoxin A has an amino acid sequence that is SEQ ID NO.:1.

14. The delivery construct of claim 1, wherein said transcytosis domain is selected from the group consisting of a transcytosis domain from *Pseudomonas* exotoxin A, botulinum toxin, diptheria toxin, pertussis toxin, cholera toxin, heat-labile *E. coli* enterotoxin, shiga toxin, and shiga-like toxin.

15. The delivery construct of claim 14, wherein said transcytosis domain is a *Pseudomonas* exotoxin A transcytosis domain.

16. The delivery construct of claim 15, wherein said *Pseudomonas* exotoxin A transcytosis domain has an amino acid sequence that is SEQ ID NO.:2.

17. A composition comprising a delivery construct of claim 1.

18. The composition of claim 17, wherein said composition further comprises a pharmaceutically acceptable diluent, excipient, vehicle, or carrier.

19. The composition of claim 17, wherein said composition is formulated for nasal or oral administration.

20. The delivery construct of claim 12, wherein said transcytosis domain is a *Pseudomonas* exotoxin A transcytosis domain.

21. The delivery construct of claim 20, wherein said *Pseudomonas* exotoxin A transcytosis domain has an amino acid sequence that is SEQ ID NO.:2.

22. The delivery construct of claim 13, wherein said *Pseudomonas* exotoxin A transcytosis domain has an amino acid sequence that is SEQ ID NO.:2.

* * * * *